(12) United States Patent
Mendel et al.

(10) Patent No.: US 11,945,875 B2
(45) Date of Patent: Apr. 2, 2024

(54) MOTILE SPERM DOMAIN CONTAINING PROTEIN 2 AND CANCER

(71) Applicant: ImmuneWalk Therapeutics, Inc., Pearl River, NY (US)

(72) Inventors: Itzhak Mendel, Rehovot (IL); Oshrat Propheta-Meiran, Petah Tikva (IL); Yaniv Salem, Kyriat Ono (IL); Anat Shoham, Hod Hasharon (IL); Niva Yacov, Tel Aviv (IL); Eyal Breitbart, Hashmonaim (IL)

(73) Assignee: ImmuneWalk Therapeutics, Inc., Pearl River, NY (US)

( * ) Notice: Subject to any disclaimer, the term of this patent is extended or adjusted under 35 U.S.C. 154(b) by 577 days.

(21) Appl. No.: 17/068,959

(22) Filed: Oct. 13, 2020

(65) Prior Publication Data

US 2021/0095044 A1 Apr. 1, 2021

Related U.S. Application Data

(63) Continuation of application No. 15/747,920, filed as application No. PCT/IB2016/054584 on Jul. 29, 2016, now abandoned.

(60) Provisional application No. 62/199,571, filed on Jul. 31, 2015.

(51) Int. Cl.
| | |
|---|---|
| *C07K 16/30* | (2006.01) |
| *A61K 45/06* | (2006.01) |
| *A61P 35/00* | (2006.01) |
| *C07K 16/18* | (2006.01) |
| *C12Q 1/6886* | (2018.01) |
| *G01N 33/50* | (2006.01) |
| *G01N 33/574* | (2006.01) |
| *G01N 33/68* | (2006.01) |
| *A61K 38/00* | (2006.01) |
| *A61K 39/00* | (2006.01) |
| *C07K 14/00* | (2006.01) |

(52) U.S. Cl.
CPC .............. *C07K 16/30* (2013.01); *A61K 45/06* (2013.01); *A61P 35/00* (2018.01); *C07K 16/18* (2013.01); *C12Q 1/6886* (2013.01); *G01N 33/5017* (2013.01); *G01N 33/5029* (2013.01); *G01N 33/574* (2013.01); *G01N 33/57492* (2013.01); *G01N 33/689* (2013.01); *A61K 38/00* (2013.01); *A61K 2039/505* (2013.01); *C07K 14/00* (2013.01); *C07K 2317/21* (2013.01); *C07K 2317/54* (2013.01); *C07K 2317/76* (2013.01); *C07K 2317/92* (2013.01); *C12Q 2600/158* (2013.01); *G01N 2333/435* (2013.01)

(58) Field of Classification Search
CPC ........ C07K 16/30; C07K 16/18; C07K 14/00; C07K 2317/21; C07K 2317/54; A61K 45/06; A61K 38/00; A61K 2039/505; A61P 35/00; C12Q 1/6886; G01N 33/5017; G01N 33/5029; G01N 33/574; G01N 33/57492; G01N 33/689
See application file for complete search history.

(56) References Cited

U.S. PATENT DOCUMENTS

| | | | |
|---|---|---|---|
| 11,697,682 | B2 | 7/2023 | Mendel et al. |
| 2004/0171009 | A1 | 9/2004 | Tang et al. |
| 2009/0137687 | A1 | 5/2009 | Chaplin |
| 2011/0015865 | A1 | 1/2011 | Rosenberg et al. |
| 2011/0257034 | A1 | 10/2011 | Barany et al. |
| 2012/0020954 | A1 | 1/2012 | Achiron et al. |
| 2014/0128277 | A1 | 5/2014 | Moller et al. |
| 2021/0077622 | A1 | 3/2021 | Mendel et al. |

FOREIGN PATENT DOCUMENTS

| | | |
|---|---|---|
| JP | 2005526705 A | 9/2005 |
| JP | 2006-151902 A | 6/2006 |
| WO | WO-0187981 A2 | 11/2001 |
| WO | WO-03053407 A1 | 7/2003 |
| WO | WO-2010052718 A1 | 5/2010 |
| WO | WO-2012016706 A1 | 2/2012 |
| WO | WO-2012121679 A1 | 9/2012 |
| WO | WO-2013088245 A1 | 6/2013 |
| WO | WO-2017/021857 A1 | 2/2017 |
| WO | WO-2017021855 A1 | 2/2017 |
| WO | WO-2022/208320 A1 | 10/2022 |

OTHER PUBLICATIONS

Thaler, R., et al., "Mospd1, a New Player in Mesenchymal Versus Epidermal Cell Differentiation," *J. Cell. Physiol.* 226:2505-2515, 2011, Wiley-Liss, Inc., United States.

Salem, Y., et al., "Newly characterized motile sperm domain-containing protein 2 promotes human breast cancer metastasis," *Intl. J. Cancer* 144:125-135, Wiley, United States (2019).

(Continued)

*Primary Examiner* — Nelson B Moseley, II

(74) *Attorney, Agent, or Firm* — STERNE, KESSLER, GOLDSTEIN & FOX P.L.L.C.

(57) ABSTRACT

Disclosed herein are methods of treating, reducing the incidence of, or preventing one or more activities in or of a cancer cell, methods of treating, reducing the incidence of, or preventing migration or metastasis of a cancer cell, methods of treating, reducing the incidence of, or preventing a cancer by reducing tumor associated macrophages (TAMs) or their migration, and methods of treating, reducing the incidence of, or preventing a cancer (including metastatic cancer), for example, with an inhibitor of Motile Sperm Domain containing Protein 2 (MOSPD2). Also disclosed are inhibitors of MOSPD2 (e.g., anti-MOSPD2 antibodies or antigen binding fragments thereof) and pharmaceutical compositions containing MOSPD2 inhibitors. Also disclosed are methods for the prediction, diagnosis, or prognosis of cancer, cancer metastasis, tumor progression, or tumor invasiveness in a subject.

17 Claims, 48 Drawing Sheets

Specification includes a Sequence Listing.

(56) References Cited

OTHER PUBLICATIONS

Kurreck, J., "RNA Interference: From Basic Research to Therapeutic Applications," *Angnew. Chem. Int. Ed.* 48(8):1378-1398, Wiley, United States (2009).

Mendel, I., et al., "Identification of Motile Sperm Domain-Containing Protein 2 as Regulator of Human Monocyte Migration," *J. Immunol.* 198(5):2125-2132, American Society of Immunologists, United States (2017).

Plagens, A., et al., "DNA and RNA interference mechanisms by CRISPR-Cas surveillance complexes," *FEMS Microbiol. Rev.* 39(3):442-463, Oxford Academic Press, United Kingdom (2015).

Kole, R., et al., "RNA therapeutics: beyond RNA interference and antisense oligonucleotides," *Nature Rev. Drug Discov.* 11(2):125-140, Nature Publishing Group, United States (2012).

Gavrilov, K., et al., "Therapeutic siRNA: principles, challenges, and strategies," *Yale J. Biol. Med.* 85:187-200, Yale University, United States (2012).

Chames, P., et al., "Bispecific antibodies for cancer therapy. The light at the end of the tunnel?" *mAbs*, 1(6):539-547, 2009, Landes Bioscience, United States (2009).

Unpublished co-pending U.S. Appl. No. 18/330,544, filed Jun. 7, 2023, Inventors: Mendel et al.

Beurger, K., "Functional Analysis of the MOSPD Gene Family," Thesis Presented for the Degree of Doctor of Philosophy, University of Edinburgh, 2010.

Han, S.M., et al., "Sperm and Oocyte Communication Mechanisms Controlling C. elegans Fertility," *Dev. Dynamics* 239:1265-1281, 2010, Wiley-Liss, Inc.

Ru, Y., et al., "Transient receptor potential-canonical 3 modulates sperm motility and capacitation-associated protein tyrosine phosphorylation via [Ca2+]i mobilization," *Acta Biochim. Biophys. Sin. (Shanghai)* 47(6):404-413, 2015, Oxford Press.

International Search Report and Written Opinion of the International Searching Authority for Int'l Appl. No. PCT/IB2016/054584, Filed: Jul. 29, 2016, dated Dec. 13, 2016.

Stephenson, S.-A., et al., "Anti-tumour effects of antibodies targeting the extracellular cysteine-rich region of the receptor tyrosine kinase EphB4," *Oncotarget* 6(10):7554-7569, 2015, Impact Journals, Orchard Park.

Khotskaya, Y.B., et al., "S6K1 promotes invasiveness of breast cancer cells in a model of metastasis of triple-negative breast cancer," *Am. J. Transl. Res.* 6(4):361-376, 2014, e-Century Publishing Corporation, Madison.

Bonatti, F., et al., "Genetic susceptibility to ANCA-associated vasculitis: state of the art," *Frontiers in Immunology*, 5:1-14; 2014, International Union of Immunological Societies, Berlin, Germany.

Stancovski, I., et al., "Mechanistic aspects of the opposing effects of monoclonal antibodies to the ERBB2 receptor on tumor growth," *Proc. Natl. Acad. Sci. USA*, 88:8691-8695 (1991), United States National Academy of Science, District of Columbia, United States.

Jiang, B., et al., "A Novel Peptide Isolated from a Phage Display Peptide Library with Trastuzumab Can Mimic Antigen Epitope HER-2," *J. Biol. Chem.*, 280:4656-4662 (2005), American Society for Biochemistry and Molecular Biology, Maryland, United States.

English translation of Document FP8, JP-2006-151902-A.

Unpublished co-pending U.S. Appl. No. 17/019,893, filed Sep. 14, 2020, Inventors: Mendel et al.

Unpublished co-pending U.S. Appl. No. 16/980,659, filed Mar. 13, 2019, Inventors: Mendel et al.

Unpublished co-pending U.S. Appl. No. 18/552,952, filed Sep. 28, 2023; U.S. National Phase of Int'l Appl. No. PCT/IB2022/052854; Int'l Filing Date: Mar. 28, 2022; Inventors: Mendel et al.

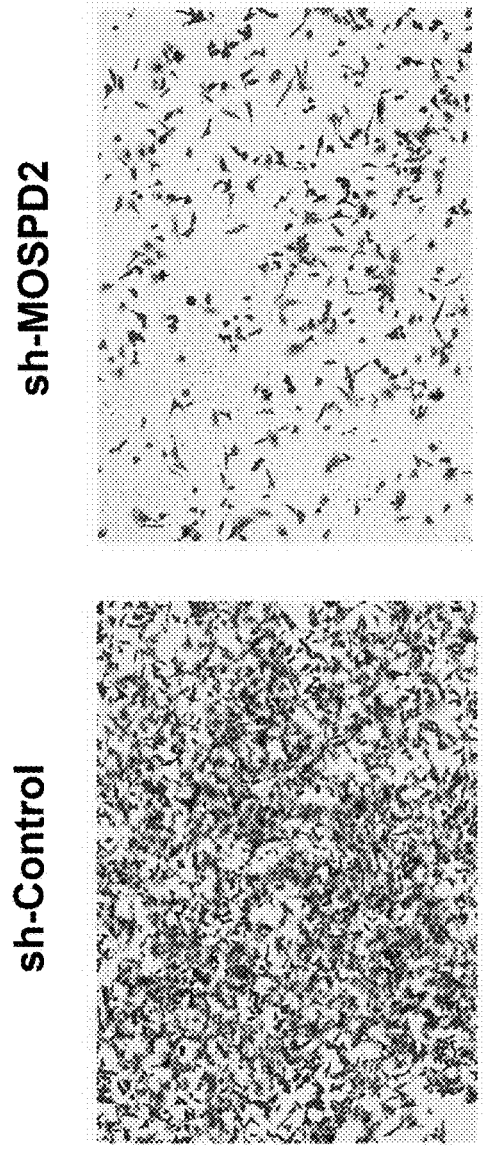
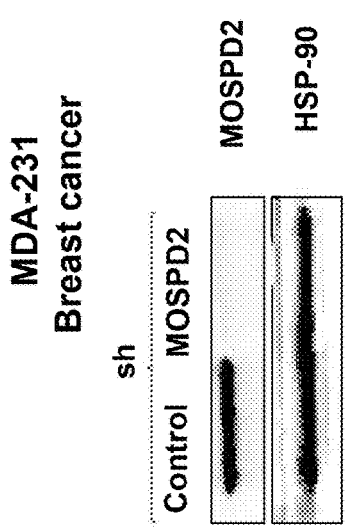

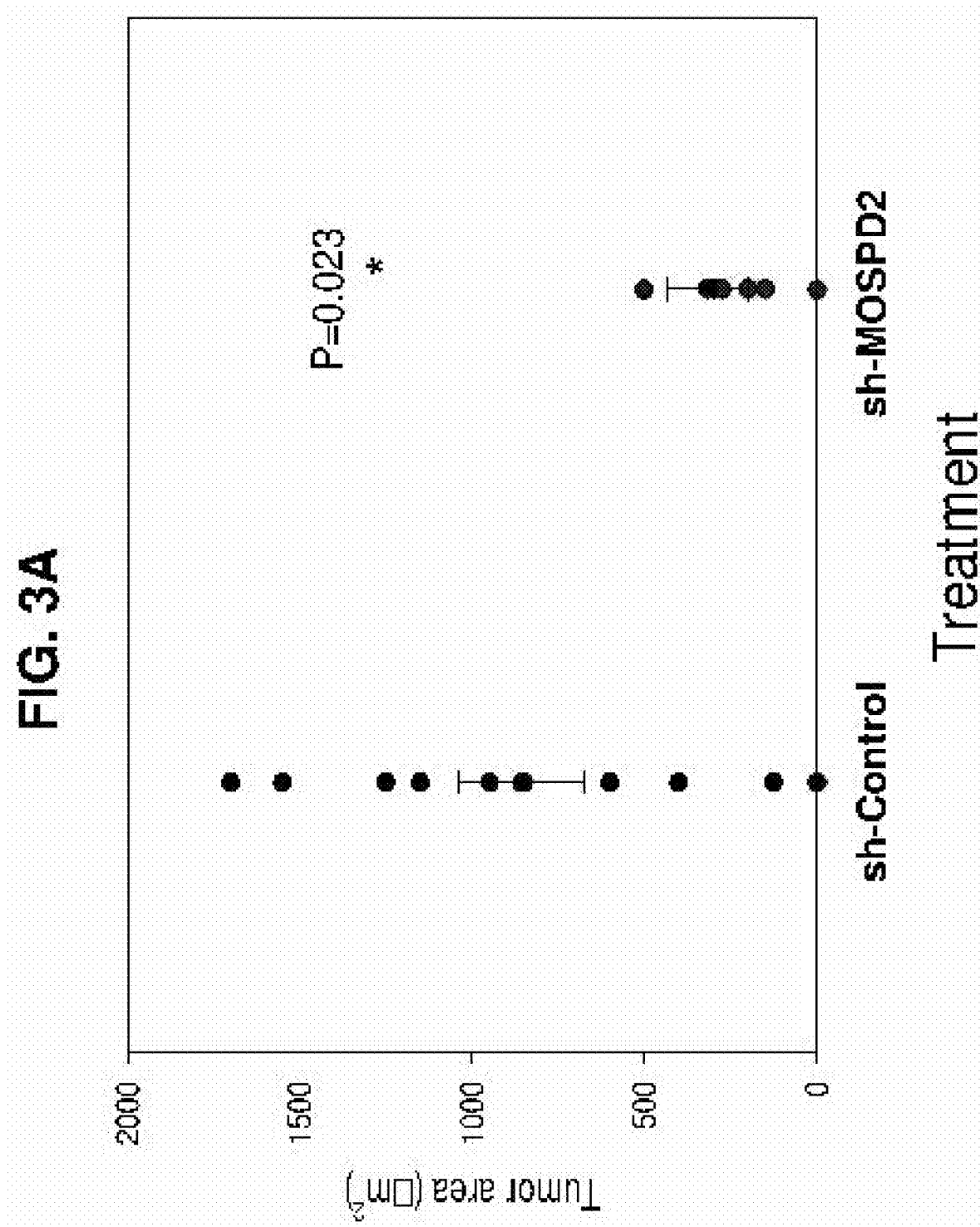

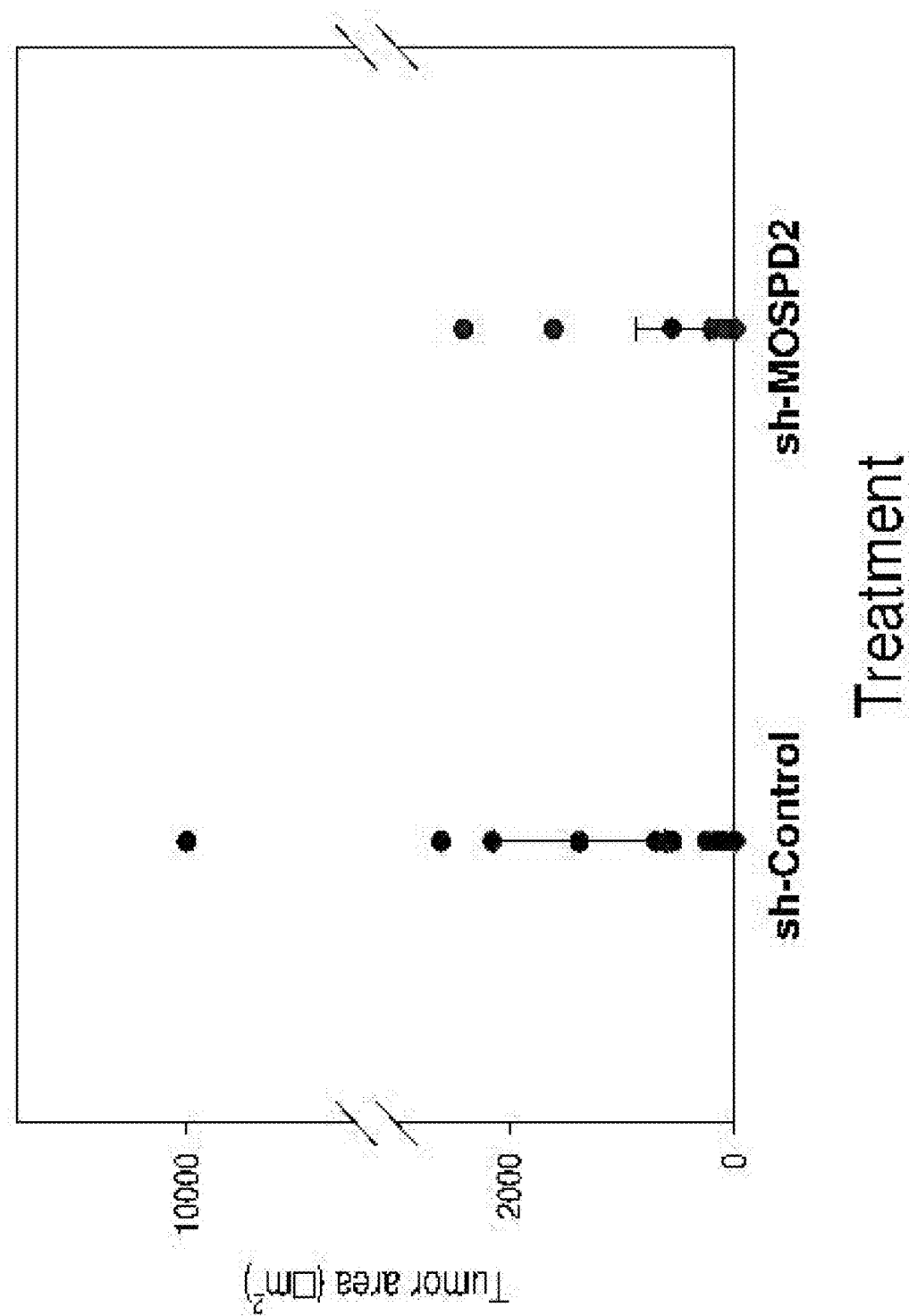

Anti-MOSPD2

Normal Hepatic Tissue

Hepatocellular Carcinoma

CRISPR-MOSPD2

CRISPR-Control

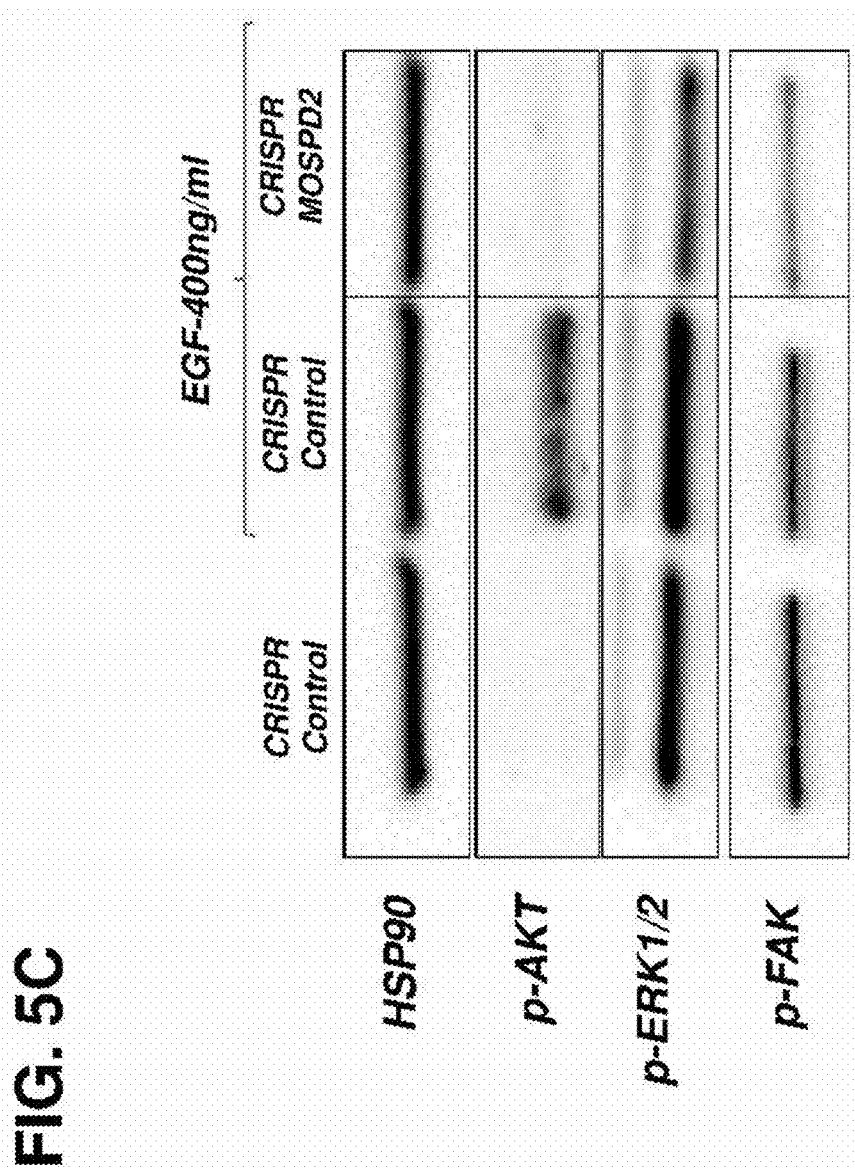

FIG. 7

MOSPD2 →

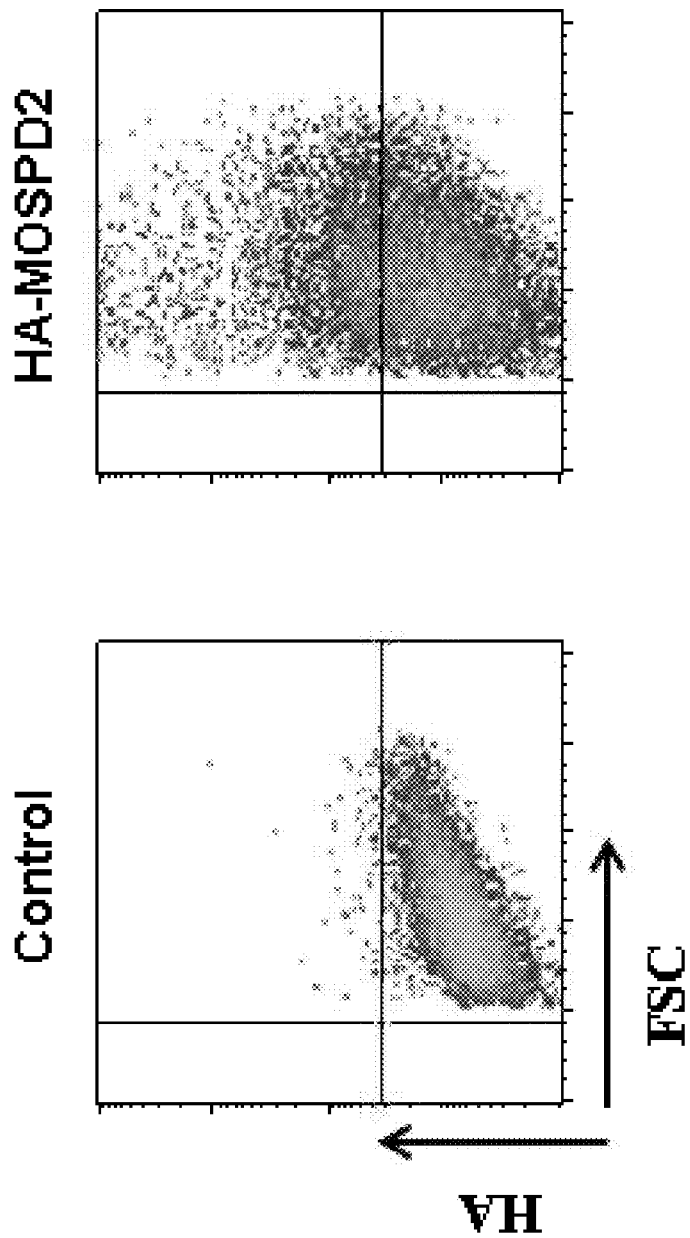

FIG. 16E

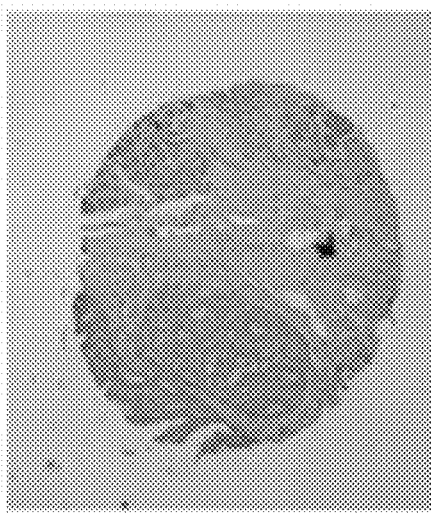
FIG. 18C Intraductal carcinoma in situ
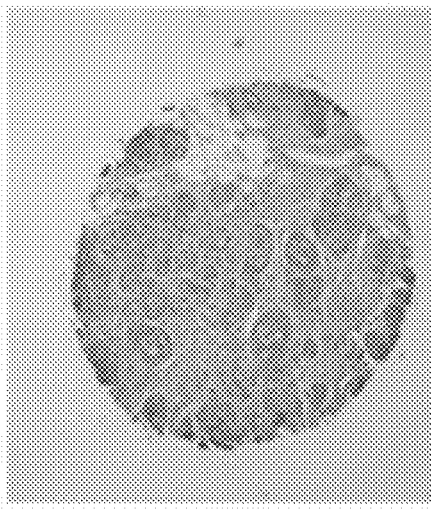
FIG. 18B Lobular carcinoma in situ
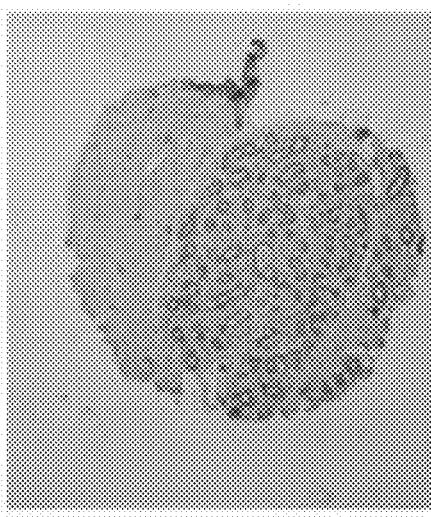
FIG. 18A NAT Invasive ductal carcinoma Invasive lobular carcinoma Metastatic invasive ductal carcinoma
(Lymph node)

Normal Colon tissue  Colon adenocarcinoma
0/7  8/12 (67%)
# of samples stained positive for MOSPD2

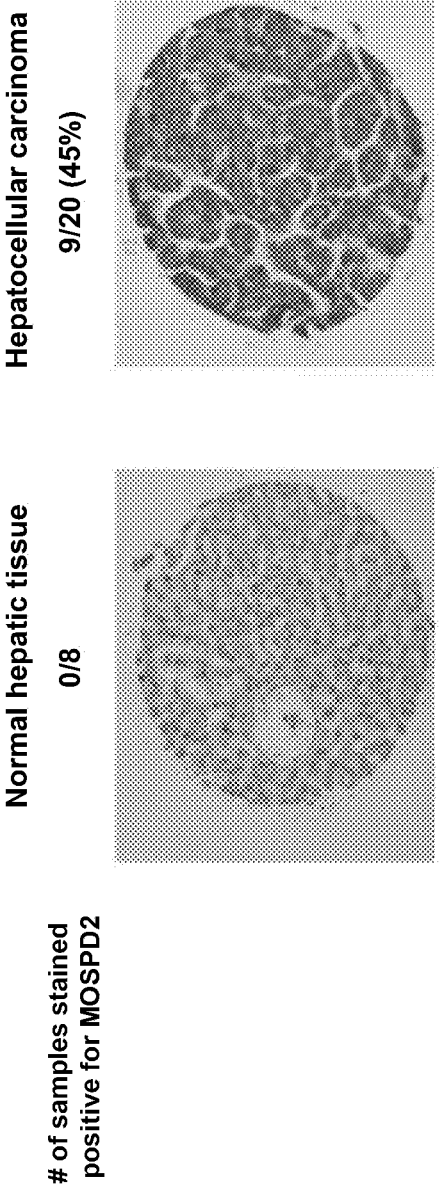

Grade I

NAT

Normal

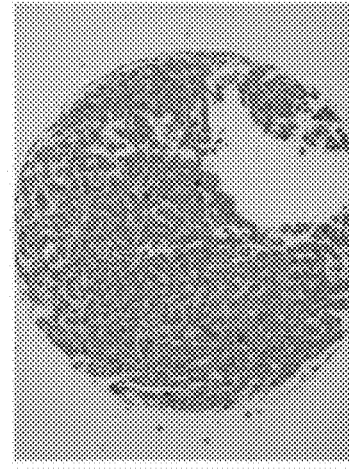
FIG. 21E Grade III
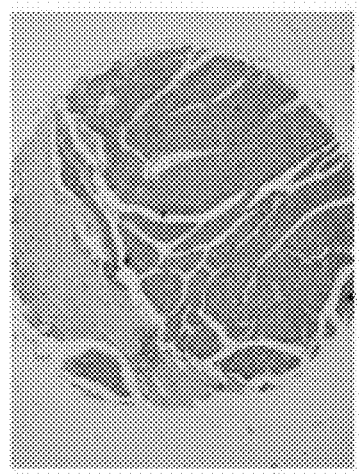
FIG. 21D Grade II

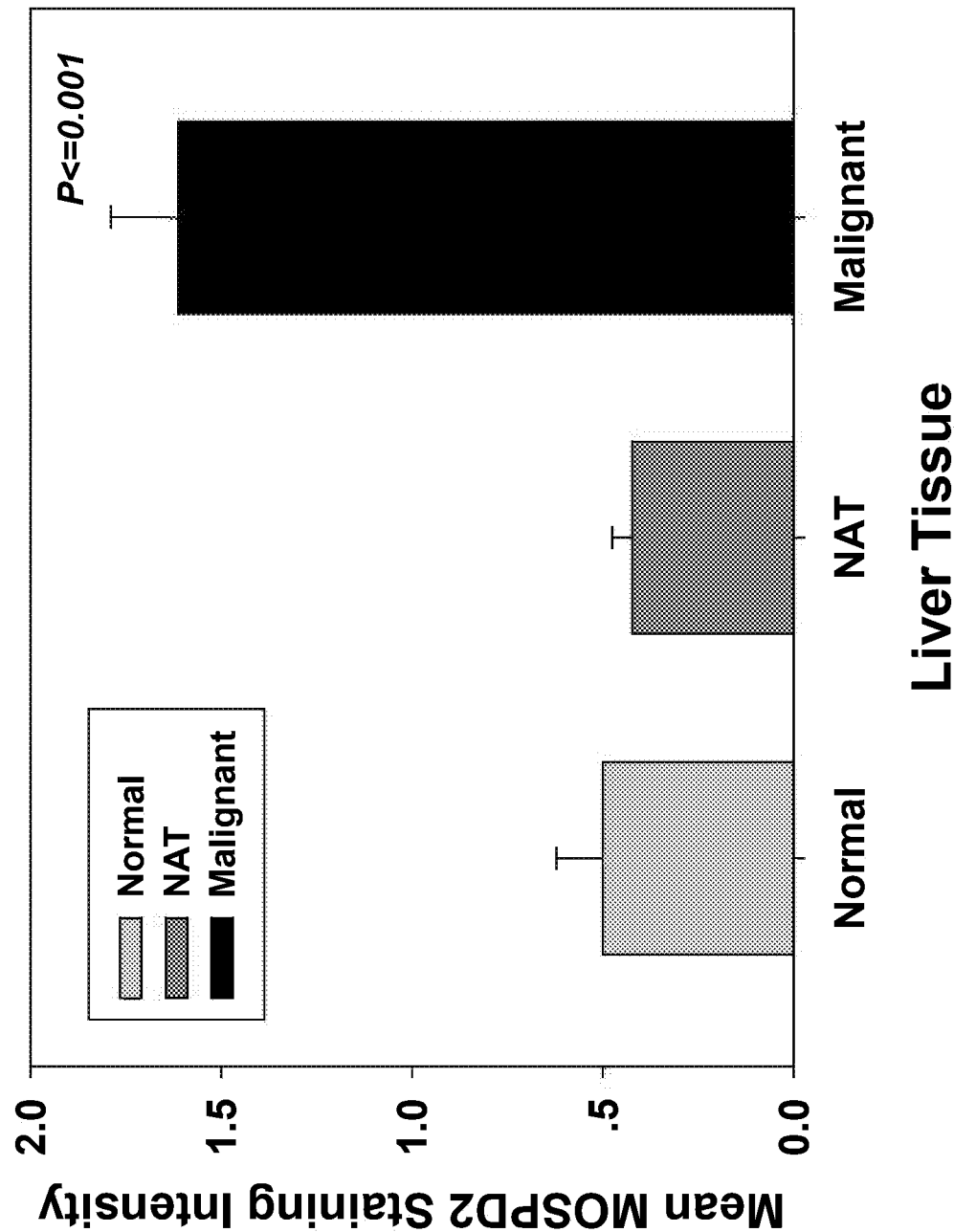

SEQUENCE LISTING

<160> NUMBER OF SEQ ID NOS: 15

<210> SEQ ID NO 1
<211> LENGTH: 518
<212> TYPE: PRT
<213> ORGANISM: Homo sapiens
<220> FEATURE:
<223> OTHER INFORMATION: motile sperm domain containing 2, protein
      variant 1

<400> SEQUENCE: 1

Met Ala Glu Asn His Ala Gln Asn Lys Ala Lys Leu Ile Ser Glu Thr
1               5                   10                  15

Arg Arg Arg Phe Glu Ala Glu Tyr Val Thr Asp Lys Ser Asp Lys Tyr
            20                  25                  30

-continued

```
Asp Ala Arg Asp Val Glu Arg Leu Gln Gln Asp Asp Asn Trp Val Glu
         35                  40                  45
Ser Tyr Leu Ser Trp Arg His Asn Ile Val Asp Glu Thr Leu Lys Met
 50                  55                  60
Leu Asp Glu Ser Phe Gln Trp Arg Lys Glu Ile Ser Val Asn Asp Leu
 65                  70                  75                  80
Asn Glu Ser Ser Ile Pro Arg Trp Leu Leu Glu Ile Gly Val Ile Tyr
                 85                  90                  95
Leu His Gly Tyr Asp Lys Glu Gly Asn Lys Leu Phe Trp Ile Arg Val
                100                 105                 110
Lys Tyr His Val Lys Asp Gln Lys Thr Ile Leu Asp Lys Lys Lys Leu
            115                 120                 125
Ile Ala Phe Trp Leu Glu Arg Tyr Ala Lys Arg Glu Asn Gly Lys Pro
130                 135                 140
Val Thr Val Met Phe Asp Leu Ser Glu Thr Gly Ile Asn Ser Ile Asp
145                 150                 155                 160
Met Asp Phe Val Arg Phe Ile Ile Asn Cys Phe Lys Val Tyr Tyr Pro
                165                 170                 175
Lys Tyr Leu Ser Lys Ile Val Ile Phe Asp Met Pro Trp Leu Met Asn
            180                 185                 190
Ala Ala Phe Lys Ile Val Lys Thr Trp Leu Gly Pro Glu Ala Val Ser
        195                 200                 205
Leu Leu Lys Phe Thr Ser Lys Asn Glu Val Gln Asp Tyr Val Ser Val
    210                 215                 220
Glu Tyr Leu Pro Pro His Met Gly Gly Thr Asp Pro Phe Lys Tyr Ser
225                 230                 235                 240
Tyr Pro Pro Leu Val Asp Asp Phe Gln Thr Pro Leu Cys Glu Asn
                245                 250                 255
Gly Pro Ile Thr Ser Glu Asp Glu Thr Ser Ser Lys Glu Asp Ile Glu
            260                 265                 270
Ser Asp Gly Lys Glu Thr Leu Glu Thr Ile Ser Asn Glu Glu Gln Thr
        275                 280                 285
Pro Leu Leu Lys Lys Ile Asn Pro Thr Glu Ser Thr Lys Ala Glu
    290                 295                 300
Glu Asn Glu Lys Val Asp Ser Lys Val Lys Ala Phe Lys Lys Pro Leu
305                 310                 315                 320
Ser Val Phe Lys Gly Pro Leu Leu His Ile Ser Pro Ala Glu Glu Leu
                325                 330                 335
Tyr Phe Gly Ser Thr Glu Ser Gly Glu Lys Lys Thr Leu Ile Val Leu
            340                 345                 350
Thr Asn Val Thr Lys Asn Ile Val Ala Phe Lys Val Arg Thr Thr Ala
        355                 360                 365
Pro Glu Lys Tyr Arg Val Lys Pro Ser Asn Ser Ser Cys Asp Pro Gly
    370                 375                 380
Ala Ser Val Asp Ile Val Ser Pro His Gly Gly Leu Thr Val Ser
385                 390                 395                 400
Ala Gln Asp Arg Phe Leu Ile Met Ala Ala Glu Met Glu Gln Ser Ser
                405                 410                 415
Gly Thr Gly Pro Ala Glu Leu Thr Gln Phe Trp Lys Glu Val Pro Arg
            420                 425                 430
Asn Lys Val Met Glu His Arg Leu Arg Cys His Thr Val Glu Ser Ser
        435                 440                 445
```

```
Lys Pro Asn Thr Leu Thr Leu Lys Asp Asn Ala Phe Asn Met Ser Asp
    450                 455                 460

Lys Thr Ser Glu Asp Ile Cys Leu Gln Leu Ser Arg Leu Leu Glu Ser
465                 470                 475                 480

Asn Arg Lys Leu Glu Asp Gln Val Gln Arg Cys Ile Trp Phe Gln Gln
                485                 490                 495

Leu Leu Leu Ser Leu Thr Met Leu Leu Leu Ala Phe Val Thr Ser Phe
            500                 505                 510

Phe Tyr Leu Leu Tyr Ser
        515

<210> SEQ ID NO 2
<211> LENGTH: 455
<212> TYPE: PRT
<213> ORGANISM: Homo sapiens
<220> FEATURE:
<223> OTHER INFORMATION: motile sperm domain containing 2, protein
      variant 2

<400> SEQUENCE: 2

Met Leu Asp Glu Ser Phe Gln Trp Arg Lys Glu Ile Ser Val Asn Asp
1               5                   10                  15

Leu Asn Glu Ser Ser Ile Pro Arg Trp Leu Leu Glu Ile Gly Val Ile
            20                  25                  30

Tyr Leu His Gly Tyr Asp Lys Glu Gly Asn Lys Leu Phe Trp Ile Arg
        35                  40                  45

Val Lys Tyr His Val Lys Asp Gln Lys Thr Ile Leu Asp Lys Lys Lys
    50                  55                  60

Leu Ile Ala Phe Trp Leu Glu Arg Tyr Ala Lys Arg Glu Asn Gly Lys
65                  70                  75                  80

Pro Val Thr Val Met Phe Asp Leu Ser Glu Thr Gly Ile Asn Ser Ile
                85                  90                  95

Asp Met Asp Phe Val Arg Phe Ile Ile Asn Cys Phe Lys Val Tyr Tyr
            100                 105                 110

Pro Lys Tyr Leu Ser Lys Ile Val Ile Phe Asp Met Pro Trp Leu Met
        115                 120                 125

Asn Ala Ala Phe Lys Ile Val Lys Thr Trp Leu Gly Pro Glu Ala Val
    130                 135                 140

Ser Leu Leu Lys Phe Thr Ser Lys Asn Glu Val Gln Asp Tyr Val Ser
145                 150                 155                 160

Val Glu Tyr Leu Pro Pro His Met Gly Gly Thr Asp Pro Phe Lys Tyr
                165                 170                 175

Ser Tyr Pro Pro Leu Val Asp Asp Phe Gln Thr Pro Leu Cys Glu
            180                 185                 190

Asn Gly Pro Ile Thr Ser Glu Asp Glu Thr Ser Ser Lys Glu Asp Ile
        195                 200                 205

Glu Ser Asp Gly Lys Glu Thr Leu Glu Thr Ile Ser Asn Glu Glu Gln
    210                 215                 220

Thr Pro Leu Leu Lys Lys Ile Asn Pro Thr Glu Ser Thr Ser Lys Ala
225                 230                 235                 240

Glu Glu Asn Glu Lys Val Asp Ser Lys Val Lys Ala Phe Lys Lys Pro
                245                 250                 255

Leu Ser Val Phe Lys Gly Pro Leu Leu His Ile Ser Pro Ala Glu Glu
            260                 265                 270

Leu Tyr Phe Gly Ser Thr Glu Ser Gly Glu Lys Lys Thr Leu Ile Val
        275                 280                 285
```

```
Leu Thr Asn Val Thr Lys Asn Ile Val Ala Phe Lys Val Arg Thr Thr
    290                 295                 300

Ala Pro Glu Lys Tyr Arg Val Lys Pro Ser Asn Ser Ser Cys Asp Pro
305                 310                 315                 320

Gly Ala Ser Val Asp Ile Val Val Ser Pro His Gly Gly Leu Thr Val
                325                 330                 335

Ser Ala Gln Asp Arg Phe Leu Ile Met Ala Ala Glu Met Glu Gln Ser
                340                 345                 350

Ser Gly Thr Gly Pro Ala Glu Leu Thr Gln Phe Trp Lys Glu Val Pro
            355                 360                 365

Arg Asn Lys Val Met Glu His Arg Leu Arg Cys His Thr Val Glu Ser
370                 375                 380

Ser Lys Pro Asn Thr Leu Thr Leu Lys Asp Asn Ala Phe Asn Met Ser
385                 390                 395                 400

Asp Lys Thr Ser Glu Asp Ile Cys Leu Gln Leu Ser Arg Leu Leu Glu
                405                 410                 415

Ser Asn Arg Lys Leu Glu Asp Gln Val Gln Arg Cys Ile Trp Phe Gln
            420                 425                 430

Gln Leu Leu Leu Ser Leu Thr Met Leu Leu Leu Ala Phe Val Thr Ser
        435                 440                 445

Phe Phe Tyr Leu Leu Tyr Ser
450                 455
```

<210> SEQ ID NO 3
<211> LENGTH: 486
<212> TYPE: PRT
<213> ORGANISM: Homo sapiens
<220> FEATURE:
<223> OTHER INFORMATION: motile sperm domain containing 2, protein variant X1

<400> SEQUENCE: 3

```
Met Ala Glu Asn His Ala Gln Asn Lys Ala Lys Leu Ile Ser Glu Thr
1               5                   10                  15

Arg Arg Arg Phe Glu Ala Glu Tyr Val Thr Asp Lys Ser Asp Lys Tyr
            20                  25                  30

Asp Ala Arg Asp Val Glu Arg Leu Gln Gln Asp Asp Asn Trp Val Glu
        35                  40                  45

Ser Tyr Leu Ser Trp Arg His Asn Ile Val Asp Glu Thr Leu Lys Met
    50                  55                  60

Leu Asp Glu Ser Phe Gln Trp Arg Lys Glu Ile Ser Val Asn Asp Leu
65                  70                  75                  80

Asn Glu Ser Ser Ile Pro Arg Trp Leu Leu Glu Ile Gly Val Ile Tyr
                85                  90                  95

Leu His Gly Tyr Asp Lys Glu Gly Asn Lys Leu Phe Trp Ile Arg Val
            100                 105                 110

Lys Tyr His Val Lys Asp Gln Lys Thr Ile Leu Asp Lys Lys Lys Leu
        115                 120                 125

Ile Ala Phe Trp Leu Glu Arg Tyr Ala Lys Arg Glu Asn Gly Lys Pro
    130                 135                 140

Val Thr Val Met Phe Asp Leu Ser Glu Thr Gly Ile Asn Ser Ile Asp
145                 150                 155                 160

Met Asp Phe Val Arg Phe Ile Ile Asn Cys Phe Lys Val Tyr Tyr Pro
                165                 170                 175

Lys Tyr Leu Ser Lys Ile Val Ile Phe Asp Met Pro Trp Leu Met Asn
            180                 185                 190
```

-continued

```
Ala Ala Phe Lys Ile Val Lys Thr Trp Leu Gly Pro Glu Ala Val Ser
            195                 200                 205
Leu Leu Lys Phe Thr Ser Lys Asn Glu Val Gln Asp Tyr Val Ser Val
210                 215                 220
Glu Tyr Leu Pro Pro His Met Gly Gly Thr Asp Pro Phe Lys Tyr Ser
225                 230                 235                 240
Tyr Pro Pro Leu Val Asp Asp Phe Gln Thr Pro Leu Cys Glu Asn
                245                 250                 255
Gly Pro Ile Thr Ser Glu Asp Glu Thr Ser Ser Lys Glu Asp Ile Glu
                260                 265                 270
Ser Asp Gly Lys Glu Thr Leu Glu Thr Ile Ser Asn Glu Glu Gln Thr
            275                 280                 285
Pro Leu Leu Lys Lys Ile Asn Pro Thr Glu Ser Thr Ser Lys Ala Glu
290                 295                 300
Glu Asn Glu Lys Val Asp Ser Lys Val Lys Ala Phe Lys Lys Pro Leu
305                 310                 315                 320
Ser Val Phe Lys Gly Pro Leu Leu His Ile Ser Pro Ala Glu Glu Leu
                325                 330                 335
Tyr Phe Gly Ser Thr Glu Ser Gly Glu Lys Lys Thr Leu Ile Val Leu
                340                 345                 350
Thr Asn Val Thr Lys Asn Ile Val Ala Phe Lys Val Arg Thr Thr Ala
            355                 360                 365
Pro Glu Lys Tyr Arg Val Lys Pro Ser Asn Ser Ser Cys Asp Pro Gly
370                 375                 380
Ala Ser Val Asp Ile Val Val Ser Pro His Gly Gly Leu Thr Val Ser
385                 390                 395                 400
Ala Gln Asp Arg Phe Leu Ile Met Ala Ala Glu Met Glu Gln Ser Ser
                405                 410                 415
Gly Thr Gly Pro Ala Glu Leu Thr Gln Phe Trp Lys Glu Val Pro Arg
                420                 425                 430
Asn Lys Val Met Glu His Arg Leu Arg Cys His Thr Val Glu Ser Ser
            435                 440                 445
Lys Pro Asn Thr Leu Thr Leu Lys Asp Asn Ala Phe Asn Met Ser Asp
450                 455                 460
Lys Thr Ser Glu Asp Ile Cys Leu Gln Phe Ala Thr Ser Ser Cys Glu
465                 470                 475                 480
Met Asp Cys Ser Pro Pro
                485

<210> SEQ ID NO 4
<211> LENGTH: 475
<212> TYPE: PRT
<213> ORGANISM: Homo sapiens
<220> FEATURE:
<223> OTHER INFORMATION: motile sperm domain containing 2, protein
      variant X2

<400> SEQUENCE: 4

Met Ala Glu Asn His Ala Gln Asn Lys Ala Lys Leu Ile Ser Glu Thr
1               5                   10                  15
Arg Arg Arg Phe Glu Ala Glu Tyr Val Thr Asp Lys Ser Asp Lys Tyr
                20                  25                  30
Asp Ala Arg Asp Val Glu Arg Leu Gln Gln Asp Asp Asn Trp Val Glu
            35                  40                  45
Ser Tyr Leu Ser Trp Arg His Asn Ile Val Asp Glu Thr Leu Lys Met
50                  55                  60
```

```
Leu Asp Glu Ser Phe Gln Trp Arg Lys Glu Ile Ser Val Asn Asp Leu
 65                  70                  75                  80

Asn Glu Ser Ser Ile Pro Arg Trp Leu Leu Glu Ile Gly Val Ile Tyr
                 85                  90                  95

Leu His Gly Tyr Asp Lys Glu Gly Asn Lys Leu Phe Trp Ile Arg Val
            100                 105                 110

Lys Tyr His Val Lys Asp Gln Lys Thr Ile Leu Asp Lys Lys Lys Leu
        115                 120                 125

Ile Ala Phe Trp Leu Glu Arg Tyr Ala Lys Arg Glu Asn Gly Lys Pro
130                 135                 140

Val Thr Val Met Phe Asp Leu Ser Glu Thr Gly Ile Asn Ser Ile Asp
145                 150                 155                 160

Met Asp Phe Val Arg Phe Ile Ile Asn Cys Phe Lys Val Tyr Tyr Pro
                165                 170                 175

Lys Tyr Leu Ser Lys Ile Val Ile Phe Asp Met Pro Trp Leu Met Asn
            180                 185                 190

Ala Ala Phe Lys Ile Val Lys Thr Trp Leu Gly Pro Glu Ala Val Ser
        195                 200                 205

Leu Leu Lys Phe Thr Ser Lys Asn Glu Val Gln Asp Tyr Val Ser Val
210                 215                 220

Glu Tyr Leu Pro Pro His Met Gly Gly Thr Asp Pro Phe Lys Tyr Ser
225                 230                 235                 240

Tyr Pro Pro Leu Val Asp Asp Phe Gln Thr Pro Leu Cys Glu Asn
                245                 250                 255

Gly Pro Ile Thr Ser Glu Asp Glu Thr Ser Ser Lys Glu Asp Ile Glu
            260                 265                 270

Ser Asp Gly Lys Glu Thr Leu Glu Thr Ile Ser Asn Glu Glu Gln Thr
        275                 280                 285

Pro Leu Leu Lys Lys Ile Asn Pro Thr Glu Ser Thr Lys Ala Glu
290                 295                 300

Glu Asn Glu Lys Val Asp Ser Lys Val Lys Ala Phe Lys Lys Pro Leu
305                 310                 315                 320

Ser Val Phe Lys Gly Pro Leu Leu His Ile Ser Pro Ala Glu Glu Leu
                325                 330                 335

Tyr Phe Gly Ser Thr Glu Ser Gly Glu Lys Lys Thr Leu Ile Val Leu
            340                 345                 350

Thr Asn Val Thr Lys Asn Ile Val Ala Phe Lys Val Arg Thr Thr Ala
        355                 360                 365

Pro Glu Lys Tyr Arg Val Lys Pro Ser Asn Ser Ser Cys Asp Pro Gly
370                 375                 380

Ala Ser Val Asp Ile Val Val Ser Pro His Gly Gly Leu Thr Val Ser
385                 390                 395                 400

Ala Gln Asp Arg Phe Leu Ile Met Ala Ala Glu Met Glu Gln Ser Ser
                405                 410                 415

Gly Thr Gly Pro Ala Glu Leu Thr Gln Phe Trp Lys Glu Val Pro Arg
            420                 425                 430

Asn Lys Val Met Glu His Arg Leu Arg Cys His Thr Val Glu Ser Ser
        435                 440                 445

Lys Pro Asn Thr Leu Thr Leu Lys Asp Asn Ala Phe Asn Met Ser Asp
450                 455                 460

Lys Thr Ser Glu Asp Ile Cys Leu Gln Tyr Ser
465                 470                 475
```

<210> SEQ ID NO 5
<211> LENGTH: 3219
<212> TYPE: DNA
<213> ORGANISM: Homo sapiens
<220> FEATURE:
<223> OTHER INFORMATION: motile sperm domain containing 2, transcript
      variant 1, mRNA, coding region 125-1678

<400> SEQUENCE: 5

| | | | | | | |
|---|---|---|---|---|---|---|
| accgcctccc | cctcccaccc | ttctctgtct | acctctgggc | gggactgccg | ggtgatgaga | 60 |
| tactcggtcg | gcgacggtag | aacgggcgac | ggcgacaacc | gcaatcacat | ccacgacggt | 120 |
| gatcatggca | gagaatcacg | cccagaataa | agccaagctc | atctctgaga | cccggaggag | 180 |
| gttcgaagct | gagtatgtga | cagataagtc | agataaatat | gatgcacgtg | atgttgaaag | 240 |
| gctacaacaa | gatgataact | gggttgaaag | ttacttatct | tggagacata | atattgtaga | 300 |
| tgaaacactg | aagatgctcg | atgagagttt | tcagtggagg | aaagaaattt | ctgtcaatga | 360 |
| ccttaatgaa | tcctccattc | ccagatggtt | attggaaatt | ggtgttattt | atctccatgg | 420 |
| ttatgacaaa | gaaggtaaca | aattgttctg | gatcagggtg | aagtatcatg | taaaagacca | 480 |
| gaaaaccata | ttggacaaaa | agaagctcat | agcattctgg | ttgaacgtt | atgctaagag | 540 |
| ggaaaatggg | aaacctgtaa | cagtgatgtt | tgacctgtca | gaaactggaa | taaatagcat | 600 |
| tgacatggac | tttgtacgct | ttatcatcaa | ctgctttaag | gtttattacc | ctaaatacct | 660 |
| ctcaaaaata | gtgatctttg | atatgccttg | gttaatgaat | gctgctttca | aaattgtgaa | 720 |
| aacctggctt | ggtccagaag | cagtgagctt | gttgaagttt | acaagcaaaa | atgaagtcca | 780 |
| ggactatgtc | agtgtagaat | acctgcctcc | ccacatgggt | ggaactgatc | ctttcaagta | 840 |
| tagctatcca | ccactagtag | atgatgactt | ccagacccca | ctgtgtgaga | atgggcctat | 900 |
| taccagtgag | gatgaaactt | caagtaaaga | agacatagaa | agtgatggca | agaaacatt | 960 |
| ggaaacaatt | tctaatgaag | aacaaacacc | tcttcttaaa | aagattaacc | caaccgaatc | 1020 |
| tacttccaaa | gcagaagaaa | atgaaaaagt | tgattcaaaa | gtgaaagctt | tcaagaaacc | 1080 |
| attgagtgta | tttaaaggcc | ccttactaca | catcagccca | gcagaagaac | tgtactttgg | 1140 |
| aagtacagaa | tccggagaga | agaaaaacctt | aatagtgttg | acaaatgtaa | ctaaaaaatat | 1200 |
| agtggcattt | aaggtgagaa | caacagctcc | agaaaaatac | agagtcaagc | caagcaatag | 1260 |
| cagctgtgac | ccggggtgcat | cagtggatat | agttgtgtct | ccccatgggg | gtttaacagt | 1320 |
| ctctgcccaa | gaccgttttc | tgataatggc | tgcagaaatg | gaacagtcat | ctggcacagg | 1380 |
| cccagcagaa | ttaactcagt | tttggaaaga | agttcccaga | aacaaagtga | tggaacatag | 1440 |
| gttaagatgc | catactgttg | aaagcagtaa | accaaacact | cttacgttaa | aagacaatgc | 1500 |
| tttcaatatg | tcagataaaa | ccagtgaaga | tatatgtcta | caactcagtc | gtttactaga | 1560 |
| aagcaatagg | aagcttgaag | accaagttca | gcgttgtatc | tggttccagc | agctgctgct | 1620 |
| ttccttaaca | atgctcttgc | ttgcttttgt | cacctctttc | ttctatttat | tgtacagtta | 1680 |
| aagaagtggt | gccgggtagg | aaccacggtt | ccttcgtcca | ttagttggaa | aaagtaacag | 1740 |
| acctaaaact | ctaccaagct | actaaaaaca | ttgcacatct | gtgcttccta | aaggaaaata | 1800 |
| tgcagcacgt | ggaggggaac | acatacatgt | cttgaaaata | aactgctaga | ataaagaaat | 1860 |
| gctggagaaa | ttgattataa | gagactatag | ctatttagta | aagtaagtaa | aggcatatcc | 1920 |
| attgtgtaaa | ttaatagttt | aaatataatt | tatttttcc | ttttgatctg | aatacttta | 1980 |
| aagcttaagt | tttatcgtgt | aaatacatta | gctaaactga | aaagtataag | taacatgctt | 2040 |
| tgttgcagcc | aaaaaatgta | atctgctttt | ttatgacaga | attattatag | ctgagctgac | 2100 |

```
ttactagctt ttctatacta tgtatataga agaacatgta tattgagaaa gaaaacatac    2160
ttatatagag gaatttatgt aaccatgact ttgtaatttt gagaattcct cccagtgatg    2220
gtcagtattc ttttggaatg taaaccgatt taatgccaaa ccaccttaac ctttgtttct    2280
cagtgttcct taacagcctg ccttttatta atctcaggct ttttatgaa cactctcatt    2340 tcagtagaat ttggaaaact aagcgtggtt ggaatttctt tgaattctgt tagtaatgcc    2400
caaaagaaaa gtctcaagca gtcccctat ccagtcattt ttatggagtt tcatgttgtc     2460
cactatagct ggacactgaa ccttttgcct aatttattat aaaggcctga ccctctattg    2520
tcccatcttc accccattc cagagcagag gagtctctgt ggaccatgaa ttgcactgtc     2580
tccctcctca tttctaaatg aaaggtatta gatataaatt ttttgaaag gttagttgtt     2640 tgagatgcta agcaggataa taaatttaga ttttaaaatg ttccctgtaa aagtcagccc    2700
atgacaagga aatttacaaa atactagagt atctagaagg gtgaaaacaa aaaaaaataa    2760
aaagaaacac agacgcccag gtgtcagctc tccgtttaaa gaatgaaaaa tgtaactcat    2820
gatgatctgt gaaaccttca aactaggacc aattgactta cttgatattc tgcctttgat    2880
atggtagtac ccacccggta ttcctaaaat cctaaaaaga tacaccttgc agtagcagag    2940
gcaatgacat gagtttgttt tctcattaat atgaccagtt tgggtctatg ttggttcaca    3000
tgtacatcta ctttatatga aagaaaaaac agttgtctgc ctgtaaaatg ttgagtttcg    3060
attgagccat gtttggagat tttattacta ttctgaaggg tagtgttgtt ggttttcatc    3120
ttcaagaagt tgattccaaa actgagttat gaagaatgat ataacagttc cttcaaaatt    3180
ggcctaggaa ataaaacctt aaaaggacaa aaaaaaaaa                          3219

<210> SEQ ID NO 6
<211> LENGTH: 3183
<212> TYPE: DNA
<213> ORGANISM: Homo sapiens
<220> FEATURE:
<223> OTHER INFORMATION: motile sperm domain containing 2, transcript
      variant 2, mRNA, coding region 278-1642

<400> SEQUENCE: 6
agtcacaata ataggtactt aaaaacatgt catatgatag gaaactagaa taacacacct      60
ctaaataatc catggattac caacttctca gcaatggtgt aaattcttct gctaaataac     120
ccgtgggtta aagaggacat cacattggaa attccagagt acttaaaata agtcagataa     180
atatgatgca cgtgatgttg aaaggctaca acaagatgat aactgggttg aaagttactt     240
atcttggaga cataatattg tagatgaaac actgaagatg ctcgatgaga gttttcagtg     300
gaggaaagaa atttctgtca atgaccttaa tgaatcctcc attccagat ggttattgga      360 aattggtgtt atttatctcc atggttatga caaagaaggt aacaaattgt tctggatcag    420
ggtgaagtat catgtaaaag accagaaaac catattggac aaaaagaagc tcatagcatt    480
ctggttggaa cgttatgcta agagggaaaa tgggaaacct gtaacagtga tgtttgacct    540
gtcagaaact ggaataaata gcattgacat ggactttgta cgctttatca tcaactgctt    600
taaggtttat taccctaaat acctctcaaa aatagtgatc tttgatatgc cttggttaat    660
gaatgctgct ttcaaaattg tgaaaacctg gcttggtcca aagcagtga gcttgttgaa     720 gtttacaagc aaaaatgaag tccaggacta tgtcagtgta gaataccctgc ctccccacat    780 gggtggaact gatccttca gtatagcta tccaccacta gtagatgatg acttccagac      840
cccactgtgt gagaatgggc ctattaccag tgaggatgaa acttcaagta aagaagacat    900
```

```
agaaagtgat ggcaaagaaa cattggaaac aatttctaat gaagaacaaa cacctcttct    960
taaaaagatt aacccaaccg aatctacttc caaagcagaa gaaaatgaaa aagttgattc   1020
aaaagtgaaa gctttcaaga aaccattgag tgtatttaaa ggccccttac tacacatcag   1080
cccagcagaa gaactgtact ttggaagtac agaatccgga gagaagaaaa ccttaatagt   1140
gttgacaaat gtaactaaaa atatagtggc atttaaggtg agaacaacag ctccagaaaa   1200
atacagagtc aagccaagca atagcagctg tgacccgggt gcatcagtgg atatagttgt   1260
gtctccccat gggggtttaa cagtctctgc ccaagaccgt tttctgataa tggctgcaga   1320
aatggaacag tcatctggca caggcccagc agaattaact cagttttgga agaagttcc    1380 cagaaacaaa gtgatggaac ataggttaag atgccatact gttgaaagca gtaaaccaaa   1440
cactcttacg ttaaaagaca atgctttcaa tatgtcagat aaaaccagtg aagatatatg   1500
tctacaactc agtcgtttac tagaaagcaa taggaagctt gaagaccaag ttcagcgttg   1560
tatctggttc cagcagctgc tgctttcctt aacaatgctc ttgcttgctt ttgtcacctc   1620
tttcttctat ttattgtaca gttaaagaag tggtgccggg taggaaccac ggttccttcg   1680
tccattagtt ggaaaagta acagacctaa aactctacca agctactaaa aacattgcac    1740
atctgtgctt cctaaaagga aatatgcagc acgtggaggg gaacacatac atgtcttgaa   1800
aataaactgc tagaataaag aaatgctgga gaaattgatt ataagagact atagctattt   1860
agtaaagtaa gtaaaggcat atccattgtg taaattaata gtttaaatat aatttatttt   1920
ttccttttga tctgaatact tttaaagctt aagttttatc gtgtaaatac attagctaaa   1980
ctgaaaagta taagtaacat gctttgttgc agccaaaaaa tgtaatctgc ttttttatga   2040
cagaattatt atagctgagc tgacttacta gcttttctat actatgtata tagaagaaca   2100
tgtatattga gaaagaaaac atacttatat agaggaattt atgtaaccat gactttgtaa   2160
ttttgagaat tcctcccagt gatggtcagt attcttttgg aatgtaaacc gatttaatgc   2220
caaaccacct taacctttgt ttctcagtgt tccttaacag cctgcctttt attaatctca   2280 ggcttttta tgaacactct catttcagta gaatttggaa aactaagcgt ggttggaatt    2340
tctttgaatt ctgttagtaa tgcccaaaag aaaagtctca agcagtcccc ctatccagtc   2400 attttatgg agtttcatgt tgtccactat agctggacac tgaacctttt gcctaattta    2460
ttataaaggc ctgacctct attgtcccat cttcaccccc attccagagc agaggagtct    2520
ctgtggacca tgaattgcac tgtctccctc ctcatttcta aatgaaaggt attagatata   2580
aatttttttg aaaggttagt tgtttgagat gctaagcagg ataataaatt tagattttaa   2640
aatgttccct gtaaaagtca gcccatgaca aggaaattta caaaatacta gagtatctag   2700
aagggtgaaa acaaaaaaaa ataaaaagaa acacagacgc ccaggtgtca gctctccgtt   2760
taaagaatga aaaatgtaac tcatgatgat ctgtgaaacc ttcaaactag gaccaattga   2820
cttacttgat attctgcctt tgatatggta gtacccaccc ggtattccta aaatcctaaa   2880
aagatacacc ttgcagtagc agaggcaatg acatgagttt gttttctcat taatatgacc   2940
agtttgggtc tatgttggtt cacatgtaca tctactttat atgaaagaaa aaacagttgt   3000
ctgcctgtaa aatgttgagt ttcgattgag ccatgtttgg agattttatt actattctga   3060
agggtagtgt tgttggtttt catcttcaag aagttgattc caaaactgag ttatgaagaa   3120
tgatataaca gttccttcaa aattggccta ggaaataaaa ccttaaaagg acaaaaaaaa   3180
aaa                                                                 3183
```

<210> SEQ ID NO 7
<211> LENGTH: 2330
<212> TYPE: DNA
<213> ORGANISM: Homo sapiens
<220> FEATURE:
<223> OTHER INFORMATION: motile sperm domain containing 2, transcript
      variant X1, mRNA, coding region 125-1582

<400> SEQUENCE: 7

| | | | | | |
|---|---|---|---|---|---|
| accgcctccc | cctcccaccc | ttctctgtct | acctctgggc | gggactgccg | ggtgatgaga | 60 |
| tactcggtcg | gcgacggtag | aacgggcgac | ggcgacaacc | gcaatcacat | ccacgacggt | 120 |
| gatcatggca | gagaatcacg | cccagaataa | agccaagctc | atctctgaga | cccggaggag | 180 |
| gttcgaagct | gagtatgtga | cagataagtc | agataaatat | gatgcacgtg | atgttgaaag | 240 |
| gctacaacaa | gatgataact | gggttgaaag | ttacttatct | tggagacata | atattgtaga | 300 |
| tgaaacactg | aagatgctcg | atgagagttt | tcagtggagg | aaagaaattt | ctgtcaatga | 360 |
| ccttaatgaa | tcctccattc | ccagatggtt | attggaaatt | ggtgttattt | atctccatgg | 420 |
| ttatgacaaa | gaaggtaaca | aattgttctg | gatcagggtg | aagtatcatg | taaaagacca | 480 |
| gaaaaccata | ttggacaaaa | agaagctcat | agcattctgg | ttgaacgtt | atgctaagag | 540 |
| ggaaaatggg | aaacctgtaa | cagtgatgtt | tgacctgtca | gaaactggaa | taaatagcat | 600 |
| tgacatggac | tttgtacgct | ttatcatcaa | ctgctttaag | gtttattacc | ctaaatacct | 660 |
| ctcaaaaata | gtgatctttg | atatgccttg | gttaatgaat | gctgctttca | aaattgtgaa | 720 |
| aacctggctt | ggtccagaag | cagtgagctt | gttgaagttt | acaagcaaaa | atgaagtcca | 780 |
| ggactatgtc | agtgtagaat | acctgcctcc | ccacatgggt | ggaactgatc | ctttcaagta | 840 |
| tagctatcca | ccactagtag | atgatgactt | ccagacccca | ctgtgtgaga | atgggcctat | 900 |
| taccagtgag | gatgaaactt | caagtaaaga | agacatagaa | agtgatggca | agaaacatt | 960 |
| ggaaacaatt | tctaatgaag | aacaaacacc | tcttcttaaa | aagattaacc | caaccgaatc | 1020 |
| tacttccaaa | gcagaagaaa | atgaaaaagt | tgattcaaaa | gtgaaagctt | tcaagaaacc | 1080 |
| attgagtgta | tttaaaggcc | ccttactaca | catcagccca | gcagaagaac | tgtactttgg | 1140 |
| aagtacagaa | tccggagaga | agaaaacctt | aatagtgttg | acaaatgtaa | ctaaaaatat | 1200 |
| agtggcattt | aaggtgagaa | caacagctcc | agaaaaatac | agagtcaagc | caagcaatag | 1260 |
| cagctgtgac | ccggggtgcat | cagtggatat | agttgtgtct | ccccatgggg | gtttaacagt | 1320 |
| ctctgcccaa | gaccgttttc | tgataatggc | tgcagaaatg | gaacagtcat | ctggcacagg | 1380 |
| cccagcagaa | ttaactcagt | tttggaaaga | agttcccaga | aacaaagtga | tggaacatag | 1440 |
| gttaagatgc | catactgttg | aaagcagtaa | accaaacact | cttacgttaa | aagacaatgc | 1500 |
| tttcaatatg | tcagataaaa | ccagtgaaga | tatatgtcta | caatttgcca | cctccagctg | 1560 |
| tgaaatggac | tgcagtccac | cctaagtact | gtgcacagta | tctccctgtg | tgtgtgcaca | 1620 |
| gtggcttccc | cttacatggt | agatttttgg | ccttaatata | atctaatccc | aaagtagttg | 1680 |
| tgtatgtttt | ctgttccttg | gcaaataaat | gaagaaataa | ttagccaaga | ttgaaaatgt | 1740 |
| attgtcctaa | cggtgtccct | ttaatgtttc | atatgaaaaa | ttatgttgac | ccactaaaat | 1800 |
| atccttgctc | aatgtctggt | cagttgaatt | taataacata | tcttgttaat | gtttgtgtgt | 1860 |
| ctattaaatg | tgactaagca | ggattactga | aaattcacta | taaaatcaaa | ggcatctaaa | 1920 |
| cgtttgtact | tgtcttgatt | aatcatatat | ttacacttga | ttttttttctg | tcttcatttg | 1980 |
| ttttatttta | atcataattg | catgattttt | ttggtactct | aatcagtaat | tttatttta | 2040 |
| atcatgtcat | tacctattca | tgaccaaatt | accaaggaac | caacatttag | atttagatat | 2100 |

-continued

| | |
|---|---|
| ttgttttcac ttaggaatgg aaattaatag attttccatg aaagcattag tgaaatatca | 2160 |
| ttaccttgat ctgcaagtag cctaaaaatg cgattgctgg taaacctggc ctcaaatttc | 2220 |
| atactaccat aactgttttt atatattgcc actaattttg actggattta atagcacttt | 2280 |
| attgtacaac tacaaaaaaa aatatattcc tagaattgtt gccagtgtaa | 2330 |

<210> SEQ ID NO 8
<211> LENGTH: 3909
<212> TYPE: DNA
<213> ORGANISM: Homo sapiens
<220> FEATURE:
<223> OTHER INFORMATION: motile sperm domain containing 2, transcript
      variant X2, mRNA, coding region 125-1549

<400> SEQUENCE: 8

| | |
|---|---|
| accgcctccc cctcccaccc ttctctgtct acctctgggc gggactgccg ggtgatgaga | 60 |
| tactcggtcg gcgacggtag aacgggcgac ggcgacaacc gcaatcacat ccacgacggt | 120 |
| gatcatggca gagaatcacg cccagaataa agccaagctc atctctgaga cccggaggag | 180 |
| gttcgaagct gagtatgtga cagataagtc agataaatat gatgcacgtg atgttgaaag | 240 |
| gctacaacaa gatgataact gggttgaaag ttacttatct tggagacata atattgtaga | 300 |
| tgaaacactg aagatgctcg atgagagttt tcagtggagg aaagaaattt ctgtcaatga | 360 |
| ccttaatgaa tcctccattc ccagatggtt attggaaatt ggtgttattt atctccatgg | 420 |
| ttatgacaaa gaaggtaaca aattgttctg gatcagggtg aagtatcatg taaaagacca | 480 |
| gaaaaccata ttggacaaaa agaagctcat agcattctgg ttggaacgtt atgctaagag | 540 |
| ggaaaatggg aaacctgtaa cagtgatgtt tgacctgtca gaaactggaa taaatagcat | 600 |
| tgacatggac tttgtacgct ttatcatcaa ctgctttaag gtttattacc ctaaatacct | 660 |
| ctcaaaaata gtgatctttg atatgccttg gttaatgaat gctgctttca aaattgtgaa | 720 |
| aacctggctt ggtccagaag cagtgagctt gttgaagttt acaagcaaaa atgaagtcca | 780 |
| ggactatgtc agtgtagaat acctgcctcc ccacatgggt ggaactgatc cttttcaagta | 840 |
| tagctatcca ccactagtag atgatgactt ccagacccca ctgtgtgaga atgggcctat | 900 |
| taccagtgag gatgaaactt caagtaaaga agacatagaa agtgatggca agaaacatt | 960 |
| ggaaacaatt tctaatgaag aacaaacacc tcttcttaaa aagattaacc caaccgaatc | 1020 |
| tacttccaaa gcagaagaaa atgaaaaagt tgattcaaaa gtgaaagctt tcaagaaacc | 1080 |
| attgagtgta tttaaaggcc ccttactaca catcagccca gcagaagaac tgtactttgg | 1140 |
| aagtacagaa tccggagaga agaaaaccctt aatagtgttg acaaatgtaa ctaaaaatat | 1200 |
| agtggcatt aaggtgagaa caacagctcc agaaaaatac agagtcaagc caagcaatag | 1260 |
| cagctgtgac ccgggtgcat cagtggatat agttgtgtct ccccatgggg gtttaacagt | 1320 |
| ctctgcccaa gaccgttttc tgataatggc tgcagaaatg gaacagtcat ctggcacagg | 1380 |
| cccagcagaa ttaactcagt tttggaaaga agttcccaga acaaagtga tggaacatag | 1440 |
| gttaagatgc catactgttg aaagcagtaa accaaacact cttacgttaa agacaatgc | 1500 |
| tttcaatatg tcagataaaa ccagtgaaga tatatgtcta caatacagtt aaagaagtgg | 1560 |
| tgccgggtag gaaccacggt tccttcgtcc attagttgga aaagtaaca gacctaaaac | 1620 |
| tctaccaagc tactaaaaac attgcacatc tgtgcttcct aaaaggaaat atgcagcacg | 1680 |
| tggaggggaa cacatacatg tcttgaaaat aaactgctag aataaagaaa tgctggaaa | 1740 |
| attgattata agagactata gctatttagt aaagtaagta aaggcatatc cattgtgtaa | 1800 |

| | |
|---|---|
| attaatagtt taaatataat ttattttttc cttttgatct gaatactttt aaagcttaag | 1860 |
| ttttatcgtg taaatacatt agctaaactg aaaagtataa gtaacatgct ttgttgcagc | 1920 |
| caaaaaatgt aatctgcttt tttatgacag aattattata gctgagctga cttactagct | 1980 |
| tttctatact atgtatatag aagaacatgt atattgagaa agaaaacata cttatataga | 2040 |
| ggaatttatg taaccatgac tttgtaattt tgagaattcc tcccagtgat ggtcagtatt | 2100 |
| cttttggaat gtaaaccgat ttaatgccaa accaccttaa cctttgtttc tcagtgttcc | 2160 |
| ttaacagcct gccttttatt aatctcaggc ttttttatga acactctcat ttcagtagaa | 2220 |
| tttgaaaaac taagcgtggt tggaatttct ttgaattctg ttagtaatgc ccaaaagaaa | 2280 |
| agtctcaagc agtcccccta tccagtcatt tttatggagt ttcatgttgt ccactatagc | 2340 |
| tggacactga accttttgcc taatttatta taaaggcctg accctctatt gtcccatctt | 2400 |
| caccccatt ccagagcaga ggagtctctg tggaccatga attgcactgt ctccctcctc | 2460 |
| atttctaaat gaaaggtatt agatataaat ttttttgaaa ggttagttgt ttgagatgct | 2520 |
| aagcaggata ataaatttag attttaaaat gttccctgta aaagtcagcc catgacaagg | 2580 |
| aaatttacaa aatactagag tatctagaag ggtgaaaaca aaaaaaaata aaaagaaaca | 2640 |
| cagacgccca ggtgtcagct ctccgtttaa agaatgaaaa atgtaactca tgatgatctg | 2700 |
| tgaaaccttc aaactaggac caattgactt acttgatatt ctgcctttga tatggtagta | 2760 |
| cccacccggt attcctaaaa tcctaaaaag atacaccttg cagtagcaga ggcaatgaca | 2820 |
| tgagtttgtt ttctcattaa tatgaccagt ttgggtctat gttggttcac atgtacatct | 2880 |
| actttatatg aaagaaaaaa cagttgtctg cctgtaaaat gttgagtttc gattgagcca | 2940 |
| tgtttggaga ttttattact attctgaagg gtagtgttgt tggttttcat cttcaagaag | 3000 |
| ttgattccaa aactgagtta tgaagaatga tataacagtt ccttcaaaat tggcctagga | 3060 |
| aataaaacct taaaggaca ctggtgtgct actttgtctt aatttgggct tttctgtttc | 3120 |
| agtttgccac ctccagctgt gaaatggact gcagtccacc ctaagtactg tgcacagtat | 3180 |
| ctccctgtgt gtgtgcacag tggcttcccc ttacatggta gattttggc cttaatataa | 3240 |
| tctaatccca aagtagttgt gtatgttttc tgttccttgg caaataaatg aagaaataat | 3300 |
| tagccaagat tgaaaatgta ttgtcctaac ggtgtccctt taatgtttca tatgaaaaat | 3360 |
| tatgttgacc cactaaaata tccttgctca atgtctggtc agttgaattt aataacatat | 3420 |
| cttgttaatg tttgtgtgtc tattaaatgt gactaagcag gattactgaa aattcactat | 3480 |
| aaaatcaaag gcatctaaac gtttgtactt gtcttgatta atcatatatt tacacttgat | 3540 |
| tttttctgt cttcatttgt ttttatttaa tcataattgc atgatttttt tggtactcta | 3600 |
| atcagtaatt ttattttaa tcatgtcatt acctattcat gaccaaatta ccaaggaacc | 3660 |
| aacatttaga tttagatatt tgttttcact taggaatgga aattaataga ttttccatga | 3720 |
| aagcattagt gaaatatcat taccttgatc tgcaagtagc ctaaaaatgc gattgctggt | 3780 |
| aaacctggcc tcaaatttca tactaccata actgttttta tatattgcca ctaatttga | 3840 |
| ctggatttaa tagcactttta ttgtacaact acaaaaaaaa atatattcct agaattgttg | 3900 |
| ccagtgtaa | 3909 |

<210> SEQ ID NO 9
<211> LENGTH: 58
<212> TYPE: DNA
<213> ORGANISM: Artificial Sequence
<220> FEATURE:
<223> OTHER INFORMATION: shRNA hairpin sequence #1 for MOSPD2

<400> SEQUENCE: 9
ccggcccaga tggttattgg aaattctcga gatttccaat aaccatctgg gttttttg    58

<210> SEQ ID NO 10
<211> LENGTH: 21
<212> TYPE: DNA
<213> ORGANISM: Artificial Sequence
<220> FEATURE:
<223> OTHER INFORMATION: target sequence on MOSPD2 for shRNA hairpin
      sequence #1

<400> SEQUENCE: 10
cccagatggt tattggaaat t                                             21

<210> SEQ ID NO 11
<211> LENGTH: 59
<212> TYPE: DNA
<213> ORGANISM: Artificial Sequence
<220> FEATURE:
<223> OTHER INFORMATION: shRNA hairpin sequence #2 for MOSPD2

<400> SEQUENCE: 11
ccgggccata ctgttgaaag cagtactcga gtactgcttt caacagtatg gctttttg    59

<210> SEQ ID NO 12
<211> LENGTH: 21
<212> TYPE: DNA
<213> ORGANISM: Artificial Sequence
<220> FEATURE:
<223> OTHER INFORMATION: MOSPD2 target sequence for shRNA hairpin
      sequence #2

<400> SEQUENCE: 12
gccatactgt tgaaagcagt a                                             21

<210> SEQ ID NO 13
<211> LENGTH: 59
<212> TYPE: DNA
<213> ORGANISM: Artificial Sequence
<220> FEATURE:
<223> OTHER INFORMATION: shRNA hairpin sequence #3 for MOSPD2

<400> SEQUENCE: 13
ccggccctcc tcatttctaa atgaactcga gttcatttag aaatgaggag ggtttttg    59

<210> SEQ ID NO 14
<211> LENGTH: 21
<212> TYPE: DNA
<213> ORGANISM: Artificial Sequence
<220> FEATURE:
<223> OTHER INFORMATION: MOSPD2 target sequence for shRNA hairpin
      sequence #3

<400> SEQUENCE: 14
ccctcctcat ttctaaatga a                                             21

<210> SEQ ID NO 15
<211> LENGTH: 9
<212> TYPE: PRT
<213> ORGANISM: Artificial Sequence
<220> FEATURE:
<223> OTHER INFORMATION: Hemagglutinin tag for MOSPD2

```
<400> SEQUENCE: 15

Tyr Pro Tyr Asp Val Pro Asp Tyr Ala
1               5
```

MOTILE SPERM DOMAIN CONTAINING PROTEIN 2 AND CANCER

RELATED APPLICATIONS

This application is a continuation of U.S. application Ser. No. 15/747,920, § 371(c) date Jan. 26, 2018, which is the U.S. national phase entry of Int'l Appl. No. PCT/IB16/54584, filed Jul. 29, 2016, which claims priority to U.S. Provisional Appl. No. 62/199,571, filed Jul. 31, 2015. These applications are incorporated herein by reference in their entireties.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Sep. 22, 2020, is named "3182.0680002_SequenceListing.txt", and is 36,152 bytes in size.

FIELD OF THE INVENTION

This invention relates to the treatment, prevention, or reduction of incidence of cancer and metastasis, for example, methods of treating, preventing, or reducing the incidence of one or more activities in or of a cancer cell, methods of treating, preventing, or reducing the incidence of migration or metastasis of a cancer cell, methods of treating, preventing, or reducing the incidence of cancer by regulating migration of tumor associated macrophages (TAMs), and methods of treating, preventing, or reducing the incidence of cancer (including metastatic cancer), with an inhibitor of a Motile Sperm Domain containing Protein 2 (MOSPD2). The invention also relates to pharmaceutical compositions comprising one or more inhibitors of MOSPD2, and to polypeptide inhibitors of MOSPD2 such as antibodies or antigen binding fragments thereof. The invention also relates to methods for the prediction, diagnosis, or prognosis of cancer, cancer metastasis, tumor progression, or tumor invasiveness in a subject.

BACKGROUND OF THE INVENTION

Metastasis, the spread of cancer cells from their tissue of origin to other organs, is a result of a multi-step process that involves a number of molecules. Evidence suggests that chemokines and chemokine receptors play an important role in tumor metastasis. Chemokines are small molecules that induce directional cell migration through interaction with their cognate receptors. Binding of chemokines to chemokine receptors activates signaling pathways such as the MAPK/ERK and PI3K/AKT pathways, resulting in phosphorylation of ERK and AKT, respectively.

Motile Sperm Domain containing Protein 2 (MOSPD2) is a 518-amino acid long, highly conserved protein with 90% homology between human and mouse. Bioinformatic analyses indicate that MOSPD2 contains a CRAL-TRIO region, named after the cellular retinaldehyde-binding protein (CRALBP) and the TRIO protein. MOSPD2 also contains a structurally related region to the nematode major sperm protein and one transmembrane region. A biological function for MOSPD2 has not yet been described. As detailed herein, the inventors found that MOSPD2 is essential for the migration of certain cells (e.g., monocytes and various cancer cells) towards different chemokines (e.g., Epidermal Growth Factor (EGF)).

SUMMARY OF THE INVENTION

The invention, in some embodiments, relates to methods of treating, preventing, or reducing the incidence of metastasis of a cancer cell with an inhibitor of a Motile Sperm Domain containing Protein 2 (MOSPD2). In some embodiments, the methods include administering to a subject in need thereof an effective amount of an inhibitor of MOSPD2. In some embodiments, the methods include contacting the cancer cell with an effective amount of an inhibitor of MOSPD2. In other embodiments, the MOSPD2 is expressed by the cancer cell.

In other embodiments, the invention relates to methods of inhibiting or preventing one or more activities in or of a cancer cell with an inhibitor of MOSPD2. In some embodiments, the methods include administering to a subject in need thereof an effective amount of an inhibitor of MOSPD2. In some embodiments, the methods include contacting the cancer cell with an effective amount of an inhibitor of MOSPD2. In some embodiments, the MOSPD2 is expressed by the cancer cell. In other embodiments, the one or more activities is one or more of: MOSPD2 expression, cancer cell migration, monocyte migration associated with tumor growth, a chemokine signaling pathway, a growth factor signaling pathway, epidermal growth factor (EGF) receptor phosphorylation, extracellular-signal-regulated kinase (ERK) phosphorylation, Protein kinase B (AKT) phosphorylation, and Focal Adhesion Kinase (FAK) phosphorylation.

In other embodiments, the invention relates to methods of treating, preventing, or reducing the incidence of a cancer with an inhibitor of MOSPD2. In some embodiments, the methods include administering to a subject in need thereof an effective amount of an inhibitor of MOSPD2. In some embodiments, the methods include contacting circulating monocytes or tumor associated macrophages with an effective amount of an inhibitor of MOSPD2 to reduce the number of tumor associated macrophages near or within the cancer mass and/or to regulate migration of tumor associated macrophages. In some embodiments, the MOSPD2 is expressed by circulating monocytes or tumor associated macrophages. In some embodiments, administering the inhibitor of MOSPD2 reduces the number of tumor associated macrophages near or within a cancer mass and/or regulates migration of tumor associated macrophages. In other embodiments, administering the inhibitor of MOSPD2 reduces the number or migration of tumor associated macrophages by at least 10% or more. In some embodiments, the methods include contacting the cancer cells with an effective amount of an inhibitor of MOSPD2. In some embodiments, the MOSPD2 is expressed by the cancer cells.

In other embodiments, the invention relates to methods of treating, preventing, or reducing the incidence of a metastatic cancer with an inhibitor of MOSPD2. In some embodiments, the methods include administering to a subject in need thereof a therapeutically effective amount of an inhibitor of MOSPD2. In some embodiments, the methods include contacting the metastatic cancer cells with an effective amount of an inhibitor of MOSPD2. In some embodiments, the MOSPD2 is expressed by the metastatic cancer cells.

In other embodiments, the methods of treating, preventing, or reducing the incidence described herein include administering a therapeutically effective amount of another anticancer drug along with the inhibitor of MOSPD2.

In other embodiments, the inhibitor of MOSPD2 is an antibody or antigen binding fragment thereof. In some embodiments, the antibody is a polyclonal, monoclonal, murine, human, humanized, or chimeric antibody. In some embodiments, the inhibitor of MOSPD2 is a small molecule, such as an oxidized phospholipid. In one preferred embodiment, the inhibitor of MOSPD2 is VB-201. In some embodiments, the inhibitor of MOSPD2 is an inhibitor of MOSPD2 that is not an oxidized phospholipid. In some embodiments, the inhibitor of MOSPD2 is an inhibitor of MOSPD2 that is not VB-201. In some embodiments, the inhibitor of MOSPD2 binds to MOSPD2 expressed on a cell surface (e.g., a cancer cell surface).

In other embodiments, the invention also relates to polypeptides that inhibit MOSPD2 expressed by a cancer cell and pharmaceutical compositions containing a polypeptide that inhibits MOSPD2 expressed by a cancer cell. In other embodiments, the polypeptide is an antibody or antigen binding fragment thereof.

In some embodiments, the invention relates to an isolated antibody or antigen binding fragment thereof that specifically binds to MOSPD2. In other embodiments, the antibody or antigen binding fragment thereof binds to MOSPD2 with an equilibrium dissociation constant ($K_D$) of from about $10^{-6}$ M to about $10^{-12}$ M. In other embodiments, the MOSPD2 is human MOSPD2. In other embodiments, the antibody or antigen binding fragment thereof specifically binds to one or more of the following amino acid regions of human MOSPD2, numbered according to SEQ ID NO:1: about 508 to about 517, about 501 to about 514, about 233 to about 241, about 509 to about 517, about 212 to about 221, about 13 to about 24, about 505 to about 517, about 505 to about 514, about 89 to about 100, about 506 to about 517, about 233 to about 245, about 504 to about 514, about 128 to about 136, about 218 to about 226, about 15 to about 24, about 83 to about 96, about 42 to about 50, about 462 to 474, about 340 to about 351, about 504 to about 517, about 462 to about 470, about 327 to about 337, about 21 to about 32, about 217 to about 226, about 510 to about 517, about 178 to about 190, about 497 to about 509, about 504 to about 516, about 64 to about 77, about 504 to about 515, about 147 to about 159, about 503 to about 515, about 88 to about 97, about 208 to about 218, about 178 to about 191, about 502 to about 515, about 503 to about 516, about 497 to about 505, about 500 to about 509, about 189 to about 202, about 189 to about 197, about 505 to about 516, about 1 to about 63, about 82 to about 239, about 93 to about 234, about 327 to about 445, about 327 to about 431, and about 497 to about 517.

In some embodiments, the antibody or antigen binding fragment thereof specifically binds to one or more of the following amino acid regions of human MOSPD2, numbered according to SEQ ID NO:1: about 505 to about 515, about 500 to about 515, about 230 to about 240, about 510 to about 520, about 210 to about 220, about 15 to about 25, about 505 to about 520, about 505 to about 515, about 90 to about 100, about 505 to about 525, about 230 to about 245, about 505 to about 510, about 130 to about 140, about 220 to about 230, about 15 to about 30, about 80 to about 95, about 40 to about 50, about 460 to about 475, about 340 to about 350, about 500 to about 515, about 460 to about 470, about 325 to about 335, about 20 to about 35, about 215 to about 225, about 510 to about 520, about 175 to about 190, about 500 to about 510, about 505 to about 530, about 60 to about 75, about 500 to about 520, about 145 to about 160, about 502 to about 515, about 85 to about 100, about 205 to about 220, about 175 to about 190, about 500 to about 505, about 500 to about 525, about 495 to about 505, about 495 to about 510, about 190 to about 200, about 190 to about 198, about 502 to about 515, about 1 to about 60, about 80 to about 240, about 90 to about 235, about 330 to about 445, about 330 to about 430, and about 495 to about 515.

In other embodiments, the invention relates to a pharmaceutical composition comprising the antibody or antigen binding fragment, and a pharmaceutically acceptable carrier.

In other embodiments, the invention relates to a method of treating, preventing, or reducing the incidence of metastasis of a cancer cell, comprising administering to a subject in need thereof a therapeutically effective amount of the antibody or antigen binding fragment thereof or the pharmaceutical composition. In other embodiments, the invention relates to a method of inhibiting or preventing one or more activities in or of a cancer cell, comprising administering to a subject in need thereof a therapeutically effective amount of the antibody or antigen binding fragment thereof or the pharmaceutical composition, wherein the one or more activities is one or more of: MOSPD2 expression, cancer cell migration, monocyte migration associated with tumor growth, a chemokine signaling pathway, a growth factor signaling pathway, EGF receptor phosphorylation, ERK phosphorylation, AKT phosphorylation, and FAK phosphorylation. In other embodiments, the invention relates to a method of treating, preventing, or reducing the incidence of a cancer, comprising administering to a subject in need thereof a therapeutically effective amount of the antibody or antigen binding fragment thereof or the pharmaceutical composition. In other embodiments, the invention relates to a method of treating, preventing, or reducing the incidence of a metastatic cancer, comprising administering to a subject in need thereof a therapeutically effective amount of the antibody or antigen binding fragment thereof or the pharmaceutical composition.

In other embodiments, the invention relates to methods for the prediction, diagnosis, or prognosis of cancer, cancer metastasis, tumor progression, or tumor invasiveness in a subject.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention.

FIG. 1A and FIG. 1C present images showing test results of cancer cells transduced with sh-control or sh-MOSPD2 lenti-virus particles in a trans-well migration assay towards 10% fetal calf serum (FCS) and EGF (200 ng/ml). MOSPD2 expression by human MDA-231 breast cancer (FIG. 1A) and A2058 melanoma (FIG. 1C) cell lines was silenced using sh-MOSPD2 lenti-virus particles. Western blots in FIG. 1B and FIG. 1D show decreased MOSPD2 protein expression in cancer cell lines transduced with sh-MOSPD2. FIGS. 1A-1D show that MOSPD2 promotes migration of metastatic breast cancer and melanoma cell lines.

FIGS. 3A-3C show in vivo test results of metastasis of MDA-231 breast cancer cells with or without MOSPD2 being silenced. In FIG. 3A, MDA-231 breast cancer cells transduced with sh-control or sh-MOSPD2 lenti-virus particles were injected ($10^6$) in the tail vein of SCID mice (n=10/group). Mice were sacrificed on day 28, their lungs harvested for H&E staining, and tumor area was determined. The results shown in FIG. 3A are expressed as mean±standard error of measured metastasis size (* p<0.05).

In FIGS. 3B and 3C, MDA-231 breast cancer cells transduced with sh-control or sh-MOSPD2 lenti-virus particles (n=13 and n=8 respectively) were injected ($5\times10^6$) in the mammary fat pad of SCID mice. Mice were sacrificed on day 56. The ipsilateral inguinal lymph node was excised (FIG. 3B), the lungs were harvested for H&E staining and the tumor area was determined (FIG. 3C). The results shown in FIG. 3C are expressed as mean±standard error of measured metastasis size: the tumor area for sh-control transduced cells is 1376.9±752.6 (n=13), compared to 550.0±326.2 (n=8) for sh-MOSPD2 transduced cells.

FIGS. 3A-3C show that MOSPD2 promotes metastasis of MDA-231 breast cancer cells in vivo.

FIGS. 4A-4E show that MOSPD2 is expressed in various human cancer tissues.

In FIGS. 5A and 5B, MDA-231 breast cancer cells were transduced with lenti-viral particles with plasmids containing control or MOSPD2 CRISPR-CAS9 system. Western blots show decreased MOSPD2 protein expression (inset). FIGS. 5A and 5B show that CRISPR-CAS9 driven MOSPD2 gene editing inhibits breast cancer cell migration.

FIG. 5C presents Western blots showing the effect of MOSPD2 silencing by CRISPR-CAS9 driven gene editing on phosphorylation events associated with cell migration. MDA-231 breast cancer cells transduced with control or MOSPD2 CRISPR-CAS9 lenti-virus particles were incubated with 10% FCS and EGF (400 ng/ml) for 10 minutes. Phosphorylation of ERK, AKT and FAK was determined by Western blotting. HSP90 was used for loading control. FIG. 5C shows that MOSPD2 silencing by CRISPR-CAS9 driven gene editing inhibits phosphorylation events associated with cell migration.

In FIG. 5D, $10^6$ CRISPR-control or CRISPR-MOSPD2 lenti-virus transduced MDA-231 cells were injected into the tail vein of 8 weeks old female SCID mice (C.B-17/IcrHsd-Prkdc$^{scid}$, Harlan Israel). Mice were sacrificed after 3 weeks and their lungs were excised for histopathologic examination. FIG. 5D shows that silencing MOSPD2 by the CRISPR-CAS9 system significantly inhibits the presence of metastatic breast cancer cells in the lungs by more than 95% (metastasis area), with a p-value of 0.002.

As shown in FIG. 6, VB-201 at 10 μg/ml nearly completely inhibits EGF induced phosphorylation of AKT, with significant inhibition observed at 5 μg/ml. HSP90 was used for loading control.

FIG. 7 lists 17 anti-MOSPD2 F(ab')2 monoclonal antibody clones that were identified following a primary screen for binding to cells over-expressing MOSPD2. Further analysis of the clones for MOSPD2 binding with enzyme-linked immunosorbent assay (ELISA) identified 12 clones having optical density (O.D.) values greater than 5 times over background (* in FIG. 7).

FIGS. 14A-14D show the cellular expression specificity and localization of MOSPD2.

FIGS. 16A-16E show MOSPD2 promotes monocyte migration. FIG. 16A shows mRNA and protein expression of MOSPD2 in U937 cells transduced with sh-control or sh-MOSPD2 lentivirus particles. One of at least three experiments is shown. FIG. 16B shows three-hour trans-well migration of U937 cells transduced with sh-control or sh-MOSPD2 lentivirus particles towards RANTES (100 ng/ml). The percent of sh-MOSPD2 transduced cells relative to sh-control transduced migrating cells is presented. One of three experiments is shown. FIG. 16C shows U937 cells transduced with sh-control or sh-MOSPD2 lentivirus particles were incubated for the indicated time (min) with RANTES, and the phosphorylation of ERK1/2 (p-ERK1/2) and AKT (p-AKT) was evaluated. HSP90 was used as loading control. FIG. 16D shows three-hour trans-well migration of U937 cells transduced with sh-control (sh-cont) or sh-MOSPD2 lentivirus particles towards MCP-3 (100 ng/ml), MCP-1 (100 ng/ml), RANTES (100 ng/ml) and SDF-1 (25 ng/ml). The percent of sh-MOSPD2 relative to sh-control transduced migrating cells is presented. One of three experiments is shown. FIG. 16E shows U937 cells transduced with sh-control (sh-cont) or sh-MOSPD2 lentivirus particles were incubated for 5 min with MCP-3 (100 ng/ml), MCP-1 (100 ng/ml), RANTES (100 ng/ml) and SDF-1 (25 ng/ml), and the phosphorylation of ERK1/2 (p-ERK1/2) and AKT (p-AKT) was evaluated. Tubulin was used as loading control.

FIGS. 18A-18F show histological images of human breast cancer samples from different pathological stages or from normal tissue adjacent to a tumor (normal adjacent tissue; NAT). The slides were stained with anti-MOSPD2 antibody. FIGS. 18A-18F show that MOSPD2 expression was associated with the transition of breast cancer cells from locally-restricted tumor to invasive and metastatic tumor.

FIGS. 20A-20D show images comparing MOSPD2 expression level in various normal and cancerous human tissues collected from the colon (FIGS. 20A-20B) or the liver (FIGS. 20C-20D). MOSPD2 was expressed in 67% of colon adenocarcinoma and in 45% of hepatocellular carcinoma samples, while no expression was detected in normal colon and liver tissues.

FIGS. 21A-21E show images comparing MOSPD2 expression level of normal tissue, NAT and cancerous tissue at different grades collected from human liver. FIGS. 21C-21E show that MOSPD2 staining intensity was increased along with the increase in the tumor grade of hepatocellular carcinoma.

FIGS. 22A-22B show MOSPD2 scoring of MOSPD2 expression intensity in samples collected from hepatocellular carcinoma. FIG. 22A shows that MOSPD2 expression was significantly increased ($p<0.001$) in samples collected from malignant hepatocellular carcinoma, compared to normal and NAT samples. FIG. 22B shows that MOSPD2 staining intensity increased significantly in correlation with the progression of hepatocellular carcinoma.

DETAILED DESCRIPTION OF THE INVENTION

Figure 1C:
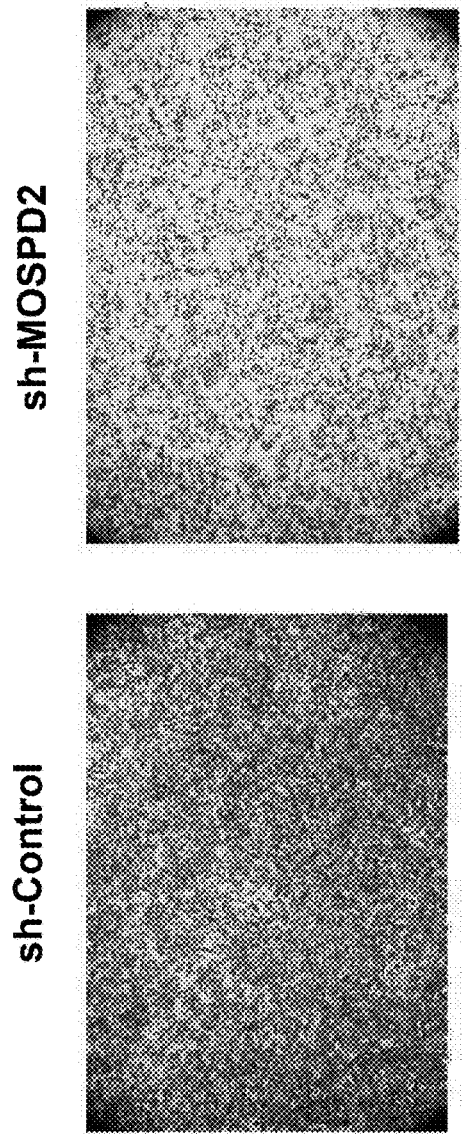
Figure 1D:
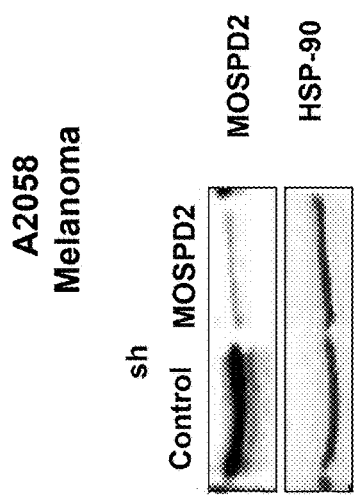

Before explaining embodiments of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

General Definitions

The terms "comprises", "comprising", "includes", "including", "having", and their conjugates mean "including but not limited to."

The term "consisting of" means "including and limited to."

The term "consisting essentially of" means the specified material of a composition, or the specified steps of a method, and those additional materials or steps that do not materially affect the basic characteristics of the material or method.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention can include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. Whether or not modified by the term "about", the claims include equivalents of the recited quantities. In one embodiment, the term "about" means within 10% of the reported numerical value. In another embodiment, the term "about" means within 5% of the reported numerical value.

Throughout this application, various embodiments of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range, such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, "MOSPD2" refers to any polypeptide classified as a Motile Sperm Domain containing Protein 2. Examples of MOSPD2 include, but are not limited to, the polypeptides of SEQ ID NOs:1-4, or any variant thereof (e.g., having a sequence at least 75%, at least 80%, at least 85%, at least 90%, at least 95%, at least 96%, at least 97%, at least 98%, or at least 99% identical to any one of SEQ ID NOs:1-4). Other examples of MOSPD2 include, but are not limited to, a polypeptide encoded by a polynucleotide of any one of SEQ ID NOs:5-8, or any variant thereof (e.g., a polynucleotide having at least 75%, at least 80%, at least 85%, at least 90%, at least 95%, at least 96%, at least 97%, at least 98%, or at least 99% identical to any one of SEQ ID NOs:5-8). Polynucleotide sequences encoding MOSPD2 can be codon optimized for expression in a particular organism by methods known in the art. Other examples of MOSPD2 can be identified by searching public databases (e.g., BLAST), as well known to one skilled in the art.

In any of the embodiments described herein, the MOSPD2 can be MOSPD2 expressed by a cancer cell, e.g., a human cancer cell. Also, in any of the embodiments described herein, the MOSPD2 can be a mammalian MOSPD2 or a human MOSPD2. Non-exclusive listing of types of cancer cells include cells of bladder cancer, breast cancer, colon cancer, rectal cancer, kidney cancer, liver cancer, lung cancer, esophageal cancer, gall-bladder cancer, ovarian cancer, pancreatic cancer, stomach cancer, cervical cancer, thyroid cancer, prostate cancer, skin cancer, hematopoietic cancer, cancer of mesenchymal origin, cancer of central or peripheral nervous system, endometrial cancer, head and neck cancer, glioblastoma, and malignant ascites. In some embodiments, the cancer is a small cell lung cancer or a non-small-cell lung cancer. In some embodiments, the cancer is skin cancer, e.g., squamous cell carcinoma, basal cell cancer, melanoma, dermatofibrosarcoma protuberans, Merkel cell carcinoma, Kaposi's sarcoma, keratoacanthoma, spindle cell tumors, sebaceous carcinomas, microcystic adnexal carcinoma, Paget's disease of the breast, atypical fibroxanthoma, leiomyosarcoma, or angiosarcoma. In some embodiments, the cancer is a hematopoietic cancer of lymphoid lineage, e.g., leukemia, acute lymphocytic leukemia, chronic lymphocytic leukemia, acute lymphoblastic leukemia, B-cell lymphoma, T-cell-lymphoma, Hodgkin's lymphoma, non-Hodgkin's lymphoma, hairy cell lymphoma or Burkitt's lymphoma. In some embodiments, the cancer is a hematopoietic cancer of myeloid lineage, e.g., fibrosarcoma, rhabdomyosarcoma, soft tissue sarcoma, or bone sarcoma. In some embodiments, the cancer is a cancer of the central or peripheral nervous system, e.g., astrocytoma, neuroblastoma, glioma, or schwannomas. In some embodiments, the cancer is anal cancer, bone cancer, gastrointestinal stomal cancer, gestational trophoblastic disease, Hodgkin's lymphoma, Kaposi sarcoma, keratoacanthoma, malignant mesothelioma, multicentric castleman disease, multiple myeloma and other plasma cell neoplasms, myeloproliferative neoplasms, neuroblastoma, non-Hodgkin's lymphoma, osteosarcoma, ovarian, fallopian tube, or primary peritoneal cancer, penile cancer, retinoblastoma, rhabdomyosarcoma, seminoma, soft tissue sarcoma, stomach (gastric) cancer, testicular cancer, teratocarcinoma, thyroid follicular cancer, vaginal cancer, vulvar cancer, Wilms tumor and other childhood kidney cancers, and xeroderma pigmentosum. In some embodiments, the cancer is bladder cancer, brain cancer (e.g., cerebrum astrocytoma), breast cancer, colon cancer (e.g., colon adenocarcinoma), esophageal cancer (e.g., esophageal adenocarcinoma), lung cancer, skin cancer (e.g., melanoma), tongue cancer (e.g., head and neck (tongue) cell carcinoma), kidney cancer (e.g., kidney clear cell carcinoma), or hepatic cancer (e.g., hepatocellular carcinoma).

As used herein, "an activity of MOSPD2" or "a MOSPD2 activity" includes any known or herein described function of a Motile Sperm Domain containing Protein 2. Such activities include, for example, regulation of cell migration (e.g., leukocyte, monocyte or cancer cell migration), presence of tumor associated macrophages, chemotaxis, chemokine-induced leukocyte migration, chemokine receptor signaling pathways, growth factor signaling pathways, EGF receptor phosphorylation, ERK phosphorylation, AKT phosphorylation, FAK phosphorylation, or inflammation.

As used herein, "chemotaxis" refers to the movement of a cell in response to a chemical stimulus. Chemotaxis includes, but is not limited to, the movement of a cancer cell to a chemokine (e.g., an EGF).

As used herein, "an inhibitor of MOSPD2" and "a MOSPD2 inhibitor" refer to any compound which downregulates an activity of MOSPD2. The inhibitor can be, for example, a polypeptide, DNA, or RNA. Inhibition of MOSPD2 can also occur, for example, by ectopic overexpression of MOSPD2 by infection, and it is intended that an inhibitor of MOSPD2 or a MOSPD2 inhibitor encompasses this type of inhibition. The inhibitor can also be, for example, a molecule that specifically binds to a MOSPD2 polypeptide, a molecule that specifically binds to a ligand of a MOSPD2 polypeptide, an antisera raised against a MOSPD2 polypeptide, a soluble MOSPD2 polypeptide, or a soluble MOSPD2 polypeptide comprising, consisting essentially of, or consisting of an extracellular domain of a MOSPD2 polypeptide. The inhibitor can also be, for example, an antibody that specifically binds to a MOSPD2 polypeptide or an antigen binding fragment of an antibody that specifically binds to a MOSPD2 polypeptide. The inhibitor can also be, for example, an RNAi, miRNA, siRNA, shRNA, antisense RNA, antisense DNA, decoy molecule, decoy DNA, double-stranded DNA, single-stranded DNA, complexed DNA, encapsulated DNA, viral DNA, plasmid DNA, naked RNA, encapsulated RNA, viral RNA, double-stranded RNA, molecule capable of generating RNA interference, or combinations thereof, that hybridizes to a nucleotide sequence encoding a MOSPD2 polypeptide. The inhibitor can also be, for example, a clustered regularly interspaced short palindromic repeats CRISPR-CAS9 system. CRISPR-CAS9 systems have been described in the literature and can include, for example, CAS9 and a guide RNA. Other gene editing techniques have also been described in the literature and can also be used. The inhibitor can also be a small molecule chemical compound which downregulates an activity of MOSPD2.

An "antibody" or an "antigen binding fragment" of an antibody include, but are not limited to, polyclonal, monoclonal, murine, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), a light chain variable region (VL) or a heavy chain variable region (VH) domain, fragments comprising either a VL or VH domain, and fragments produced by a Fab expression library. An antibody or antigen binding fragment of an antibody can be of any type (e.g., IgG, IgE, IgM, IgD, IgA, and IgY), class (e.g., IgG1, IgG2, IgG3, IgG4, IgA1 and IgA2) or subclass of immunoglobulin molecule. Methods for making an antigen binding fragment of an antibody are known and include, for example, chemical or protease digestion of an antibody.

A "constant region" of an antibody refers to the constant region of the antibody light chain or the constant region of the antibody heavy chain, either alone or in combination.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3.

By "specifically binds," it is generally meant that an antibody or fragment, variant, or derivative thereof binds to an epitope by its antigen-binding domain, and that the binding entails some complementarity between the antigen binding domain and the epitope. According to this definition, an antibody or fragment, variant, or derivative thereof is said to "specifically bind" to an epitope when it binds to that epitope via its antigen-binding domain more readily than it would bind to a random, unrelated epitope.

As used herein, an "epitope" refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by methods described in the literature and herein, e.g., NMR spectroscopy, X-ray diffraction crystallography studies, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping).

The term "percent identity," as known in the art, is a relationship between two or more polypeptide sequences or two or more polynucleotide sequences, as determined by comparing the sequences. In the art, "identity" and "sequence identity" also mean the degree of sequence relatedness between polypeptide or polynucleotide sequences, as the case may be, as determined by the match between strings of such sequences. "Identity" and "similarity" can be readily calculated by known methods and publicly available resources, including but not limited to those described in: (1) Computational Molecular Biology (Lesk, A. M., Ed.) Oxford University: NY (1988); (2) Biocomputing: Informatics and Genome Projects (Smith, D. W., Ed.) Academic: NY (1993); (3) Computer Analysis of Sequence Data, Part I (Griffin, A. M., and Griffin, H. G., Eds.) Humania: NJ (1994); (4) Sequence Analysis in Molecular Biology (von Heinje, G., Ed.) Academic (1987); and (5) Sequence Analysis Primer (Gribskov, M. and Devereux, J., Eds.) Stockton: NY (1991).

A polynucleotide can "hybridize" to another polynucleotide, when a single-stranded form of the nucleic acid fragment can anneal to the other nucleic acid fragment under the appropriate conditions of temperature and solution ionic strength. Hybridization and washing conditions are well known and exemplified, for example, in Sambrook et al., Molecular Cloning: A Laboratory Manual, 2nd ed., Cold Spring Harbor Laboratory: Cold Spring Harbor, N.Y. (1989), particularly Chapter 11 and Table 11.1 therein (incorporated herein by reference in its entirety). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One exemplary set of stringent conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of exemplary stringent conditions uses higher temperatures in which the washes are identical to those above except for the temperature of the final two 30 min washes in 0.2×SSC, 0.5% SDS was increased to 60° C. This set of stringent conditions can be modified to a "highly stringent condition" by adding two final washes in 0.1×SSC, 0.1% SDS at 65° C. An additional exemplary set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment, the length for a hybridizable nucleic acid is at least about 10 nucleotides. In other embodiments, a minimum length for a hybridizable nucleic acid is at least about 15 nucleotides, or at least about 20 nucleotides.

As used herein throughout, the term "alkyl" refers to a saturated aliphatic hydrocarbon including straight chain and branched chain groups. In some embodiments, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a medium size alkyl having 1 to 10 carbon atoms. In some embodiments, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydro furane, tetrahydropyrane, morpholino and the like.

An "alkoxy" group refers to both an —O-alkyl and an —O-cycloalkyl group, as defined herein.

An "aryloxy" group refers to both an —O-aryl and an —O-heteroaryl group, as defined herein.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R group, where R is hydrogen, alkyl, alkenyl, cycloalkyl, aryl, heteroaryl (bonded through a ring carbon) or heteroalicyclic (bonded through a ring carbon) as defined herein.

An "aldehyde" group refers to a carbonyl group, where R is hydrogen.

A "thiocarbonyl" group refers to a —C(=S)—R group, where R is as defined herein.

A "C-carboxy" group refers to a —C(=O)—O—R groups, where R is as defined herein.

An "O-carboxy" group refers to an RC(=O)—O— group, where R is as defined herein.

An "oxo" group refers to a =O group.

A "carboxylic acid" group refers to a C-carboxyl group in which R is hydrogen.

A "halo" group refers to fluorine, chlorine, bromine or iodine.

A "trihalomethyl" group refers to a —CX$_3$ group wherein X is a halo group as defined herein.

A "sulfinyl" group refers to an —S(=O)—R group, where R is as defined herein.

A "sulfonyl" group refers to an —S(=O)$_2$—R group, where R is as defined herein.

An "S-sulfonamido: group refers to a —S(=O)$_2$—NR$_2$ group, with each of R as is defined herein.

An "N-sulfonamido" group refers to an RS(=O)$_2$—NR group, where each of R is as defined herein.

An "O-carbamyl" group refers to an —OC(=O)—NR$_2$ group, where each of R is as defined herein.

An "N-carbamyl" group refers to an ROC(=O)—NR— group, where each of R is as defined herein.

An "O-thiocarbamyl" group refers to an —OC(=S)—NR$_2$ group, where each of R is as defined herein.

An "N-thiocarbamyl" group refers to an ROC(=S)NR— group, where each of R is as defined herein.

An "amino" group refers to an —NR$_2$ group where each of R is as defined herein.

A "C-amido" group refers to a —C(=O)—NR$_2$ group, where each of R is as defined herein.

An "N-amido" group refers to an RC(=O)—NR— group, where each of R is as defined herein.

An "urea" group refers to an —NRC(=O)—NR$_2$ group, where each of R is as defined herein.

A "guanidino" group refers to an —RNC(=N)—NR$_2$ group, where each of R is as defined herein.

A "guanyl" group refers to an R$_2$NC(=N)— group, where each of R is as defined herein.

The term "phosphonyl" or "phosphonate" describes a —P(=O)(OR)$_2$ group, with each of R as defined herein.

The term "phosphate" describes an —O—P(=O)(OR)$_2$ group, with each of R as defined herein.

A "phosphoric acid" is a phosphate group in which each of R is hydrogen.

The term "phosphinyl" describes a —PR$_2$ group, with each of R as defined herein.

The term "thiourea" describes a —NR—C(=S)—NR— group, with each of R as defined herein.

The term "saccharide" refers to one or more sugar unit, either an open-chain sugar unit or a cyclic sugar unit (e.g., pyranose- or furanose-based units), and encompasses any monosaccharide, disaccharide and oligosaccharide, unless otherwise indicated.

The term "salt" includes both internal salt or external salt. In some embodiments, the salt is an internal salt, i.e., a zwitterion structure. In some embodiments, the salt is an external salt. In some embodiments, the external salt is a pharmaceutically acceptable salt having a suitable counter ion. Suitable counterions for pharmaceutical use are known in the art.

The term "VB-201" refers to 1-hexadecyl-2-(4'-carboxy) butyl-glycero-3-phosphocholine. According to embodiments of the present invention, VB-201 may be a chiral enantiomer of 1-hexadecyl-2-(4'-carboxy)butyl-glycero-3-phosphocholine, i.e., either the (R)-enantiomer ((R)-1-hexadecyl-2-(4'-carboxy)butyl-sn-glycero-3-phosphocholine) or the (S)-enantiomer ((S)-1-hexadecyl-2-(4'-carboxy)butyl-sn-glycero-3-phosphocholine), or a mixture thereof (e.g., a racemate). According to exemplary embodiments, VB-201 is (R)-1-hexadecyl-2-(4'-carboxy)butyl-sn-glycero-3-phosphocholine. As understood by those skilled in the art, designating VB-201 as the (R)-enantiomer or the (S)-enantiomer does not require 100% enantiomeric purity, but instead refers to a substantially enriched single enantiomer either as an R or S isomer (e.g., having an enantiomeric excess of at least 80%, at least 85%, at least 90%, at least 95%, at least 98%, at least 99%, or higher). In some embodiments, VB-201 is (R)-1-hexadecyl-2-(4'-carboxy) butyl-sn-glycero-3-phosphocholine having at least 90% enantiomeric excess.

The term "VB-221" refers to 1-(2'-octyl)dodecyl-2-(4'-carboxy)butyl-glycero-3-phosphocholine. According to embodiments of the present invention, VB-221 may be a chiral enantiomer of (1-(2'-octyl)dodecyl-2-(4'-carboxy) butyl-glycero-3-phosphocholine), i.e., either the (R)-enantiomer or the (S)-enantiomer, or any mixtures thereof (e.g., a racemate). According to exemplary embodiments, VB-221 is (R)-1-(2'-octyl)dodecyl-2-(4'-carboxy)butyl-sn-glycero-3-phosphocholine. Similarly, as understood by those skilled in the art, designating VB-221 as the (R)-enantiomer or the (S)-enantiomer does not require 100% enantiomeric purity, but instead refers to a substantially enriched single enantiomer either as an R or S isomer (e.g., having an enantiomeric excess of at least 80%, at least 85%, at least 90%, at least 95%, at least 98%, at least 99%, or higher). In some embodiments, VB-221 is (R)-1-(2'-octyl)dodecyl-2-(4'-carboxy)butyl-sn-glycero-3-phosphocholine having at least 90% enantiomeric excess.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

MOSPD2 and Inhibitors of MOSPD2

Inhibition of MOSPD2 has been found to inhibit migration of cancer cells and monocytes towards different chemokines (e.g., EGF) and block activation of chemokine receptor signaling pathways. These results indicate that MOSPD2 is pivotal for cancer cell migration and metastasis and that blocking its activity has therapeutic benefit, for example, in treating, preventing, or reducing the incidence of metastasis of cancer cells.

Embodiments of the invention relate to an inhibitor of MOSPD2, e.g., MOSPD2 expressed by a cancer cell, or to methods and compositions comprising an inhibitor of MOSPD2, e.g., MOSPD2 expressed by a cancer cell. In some embodiments the MOSPD2 is a mammalian MOSPD2. In other embodiments, the MOSPD2 is a human MOSPD2. In some embodiments, the inhibitor is an isolated binding molecule that inhibits MOSPD2. In other embodiments, the inhibitor is a polypeptide, DNA, or RNA. In other embodiments, the inhibitor is a polypeptide that specifically binds to MOSPD2. In other embodiments, the inhibitor is an antibody or antigen binding fragment thereof that specifically binds to MOSPD2. In other embodiments, the inhibitor is an RNA silencing agent.

In additional embodiments of the invention, inhibition of MOSPD2 and downregulation of a MOSPD2 activity can be affected on the genomic and/or the transcription level using a variety of molecules which interfere with transcription and/or translation [e.g., RNA silencing agents (e.g., antisense, siRNA, shRNA, micro-RNA), Ribozyme and DNAzyme], or on the protein level using e.g., antagonists, enzymes that cleave the polypeptide, small molecules that interfere with the protein's activity (e.g., competitive ligands) and the like.

Following is an exemplary list of agents capable of downregulating expression level and/or activity of a target such as MOSPD2.

Inhibition of MOSPD2 can occur, for example, by ectopic overexpression of MOSPD2 by infection, and it is intended that an inhibitor of MOSPD2 or a MOSPD2 inhibitor encompasses this type of inhibition.

Downregulation of MOSPD2 can also be achieved by gene editing. Gene editing can be performed, for example, with a clustered regularly interspaced short palindromic repeats CRISPR-CAS9 system. CRISPR-CAS9 systems have been described in the literature and can include, for example, CAS9 and a guide RNA. Other gene editing techniques have also been described in the literature and can also be used.

Downregulation of MOSPD2 can also be achieved by RNA silencing. As used herein, the phrase "RNA silencing" refers to a group of regulatory mechanisms [e.g., RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In some embodiments, the RNA silencing agent is capable of preventing complete processing (e.g., the full translation and/or expression) of an mRNA molecule through a post-transcriptional silencing mechanism. RNA silencing agents include non-coding RNA molecules, for example, RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarilyconserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

Some embodiments of the invention contemplate use of dsRNA to downregulate protein expression from mRNA.

The term "siRNA" refers to small inhibitory RNA duplexes (generally between 18-30 basepairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is theorized to result from providing Dicer with a substrate (27 mer) instead of a product (21 mer) and that this improves the rate or efficiency of entry of the siRNA duplex into RISC.

The strands of a double-stranded interfering RNA (e.g., an siRNA) may be connected to form a hairpin or stem-loop structure (e.g., an shRNA or sh-RNA). Thus, as mentioned, the RNA silencing agent of some embodiments of the invention may also be a short hairpin RNA (shRNA).

The terms "shRNA" or "sh-RNA", as used herein, refer to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide. As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell.

According to another embodiment, the RNA silencing agent may be a miRNA or a mimic thereof.

The term "microRNA", "miRNA", and "miR" are synonymous and refer to a collection of non-coding single-stranded RNA molecules of about 19-28 nucleotides in length, which regulate gene expression. miRNAs are found in a wide range of organisms and have been shown to play a role in development, homeostasis, and disease etiology.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O,4'-C-ethylene-bridged nucleic acids (ENA)). For mature, double stranded miRNA mimics, the length of the duplex region can vary between 13-33, 18-24 or 21-23 nucleotides. The miRNA can also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA can be the first 13-33 nucleotides of the pre-miRNA. The sequence of the miRNA can also be the last 13-33 nucleotides of the pre-miRNA.

Another agent capable of downregulating a target is a DNAzyme molecule capable of specifically cleaving an mRNA transcript or DNA sequence of the target. DNAzymes are single-stranded polynucleotides which are capable of cleaving both single and double stranded target sequences. (Breaker et al., Chemistry and Biology 1995; 2:655; Santoro et al., Proc. Natl. Acad. Sci. USA 1997; 943:4262.) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions. (Santoro et al.; Khachigian, Curr. Cpin. Mol. Ther. 2002; 4:119-121.)

Downregulation of a target can also be affected by using an antisense polynucleotide capable of specifically hybridizing with an mRNA transcript encoding the target.

Another agent capable of downregulating a target is a ribozyme molecule capable of specifically cleaving an mRNA transcript encoding a target. Ribozymes are being increasingly used for the sequence-specific inhibition of gene expression by the cleavage of mRNAs encoding proteins of interest. (Welch et al., Curr. Cpin. Biotechnol. 1998; 9:486-96.)

Another agent capable of downregulating a target is any molecule which binds to and/or cleaves the target. Such molecules can be antagonists of the target, or inhibitory peptides of the target.

It will be appreciated that a non-functional analogue of at least a catalytic or binding portion of a target can be also used as an agent which downregulates the target.

Another agent which can be used along with some embodiments of the invention to downregulate a target is a molecule which prevents target activation or substrate binding.

In some embodiments, an inhibitor of a given protein target inhibits the protein by binding to the protein, by binding to a compound which binds to the protein (e.g., a substrate, a regulatory protein) and/or by binding to an oligonucleotide (e.g., mRNA) encoding the protein.

In some embodiments, the inhibitor of MOSPD2 is a small molecule (e.g., characterized by a molecular weight of less than 800 Da). In some embodiments, the small molecule MOSPD2 inhibitor is a tocopherol or a derivative thereof (e.g., alpha-tocopherol, beta-tocopherol, gamma-tocopherol, delta-tocopherol), a triterpene (e.g., squalene), a vitamin A or a derivative thereof (e.g., retinaldehyde), a phosphatidylglyceride (e.g., phosphatidylinositol), or a phospholipid (e.g., phosphatidylcholine, an oxidized phospholipid).

In some embodiments, the small molecule MOSPD2 inhibitor is an oxidized phospholipid having a structure according to Formula I:

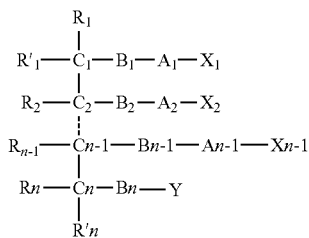

Formula I or a pharmaceutically acceptable salt, a hydrate or a solvate thereof, wherein:
n is an integer from 1 to 6, wherein when n is 1, Cn, Bn, Rn, and Y are absent, and $C_1$ is attached to R'n;

each of $B_1, B_2, \ldots Bn-1$ and Bn is independently selected from the group consisting of oxygen, sulfur, nitrogen, phosphorus and silicon, whereby each of said nitrogen, phosphorus and silicon is optionally substituted by one substituent selected from the group consisting of alkyl, halo, cycloalkyl, aryl, hydroxy, thiohydroxy, alkoxy, aryloxy, thioaryloxy, thioalkoxy and oxo;

each of $A_1, A_2, \ldots An-1$ and An is independently selected from the group consisting of CR"R'", C=O and C=S, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-biphosphonate, phosphoinositol-4,5-bisphosphate, pyrophosphate, phosphoethanolamine-diethylenetriaminepentaacetate, dinitrophenyl-phosphoethanolamine, phosphoglycerol and a moiety having the general formula:

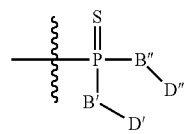

wherein:
each of B' and B" is independently selected from the group consisting of sulfur and oxygen; and each of D' and D" is independently selected from the group consisting of hydrogen, alkyl, amino substituted alkyl, cycloalkyl, phosphonate and thiophosphonate; and each of $X_1, X_2, \ldots Xn-1$ is independently a saturated or unsaturated hydrocarbon having the general Formula II:

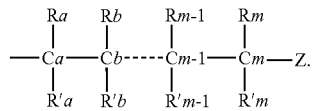

Formula II wherein m is an integer from 1 to 26; and

Z is selected from the group consisting of:

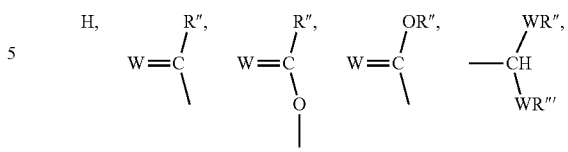

and —OR",
wherein W is selected from the group consisting of oxygen and sulfur;

wherein at least one of $X_1, X_2, \ldots Xn-1$ comprises a Z other than hydrogen, and wherein:
each of $R_1, R'_1, R_2, \ldots Rn-1, Rn, R'n$, each of R" and R'" and each of Ra, R'a, Rb, R'b, . . . . Rm-1, R'm-1, Rm and R'm is independently selected from the group consisting of a bond, hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, or, alternatively, at least two of $R_1, R'_1, R_2, \ldots Rn-1, Rn$ and R'n and/or at least two of Ra, R'a, Rb, R'b, . . . Rm-1, R'm-1, Rm and R'm form at least one four-, five- or six-membered aromatic, heteroaromatic, alicyclic or heteroalicyclic ring, or a pharmaceutically acceptable salt, a hydrate or a solvate thereof. In any of the embodiments described herein, the oxidized phospholipid can exist as a stereoisomeric mixture of any ratio, for example, as a substantially enriched single enantiomer such as an R or S isomer (e.g., having an enantiomeric excess of at least 80%, at least 85%, at least 90%, at least 95%, at least 98%, at least 99%, or higher), or as a mixture of two enantiomers (e.g., a racemic mixture); and/or as a substantially enriched single diastereomer (e.g., having an diastereomeric excess of at least 80%, at least 85%, at least 90%, at least 95%, at least 98%, at least 99%, or higher), or as a mixture of two or more diastereomers.

In one embodiment, the oxidized phospholipid useful in any of the methods of the present disclosure has a structure according to Formula III:

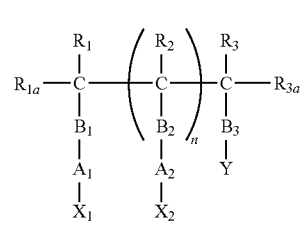

Formula III or a pharmaceutically acceptable salt, hydrate or solvate thereof.

In Formula III, n is an integer selected from 1 to 4.

In Formula III, $B_1$, each $B_2$, and $B_3$ are independently selected from the group consisting of oxygen, sulfur, and $NR_4$, wherein $R_4$ is selected from hydrogen, alkyl, cycloalkyl, aryl, and acyl.

In Formula III, $A_1$ and each $A_2$ are independently selected from the group consisting of $CR_eR_{cc}$, $CR_e=CR_{cc}$, $C=O$ and $C=S$, wherein $R_e$ and $R_{cc}$ are independently selected from hydrogen, alkyl, alkenyl, alkynyl, cycloalkyl, aryl, and heteroaryl.

In Formula III, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, phosphoglycerol, and a moiety having the general formula:

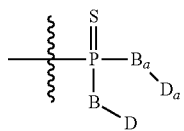

wherein:

each of B and $B_a$ is independently selected from the group consisting of sulfur and oxygen; and D and $D_a$ are independently selected from the group consisting of hydrogen, alkyl, aminoalkyl, cycloalkyl, phosphonate and thiophosphonate.

In Formula III, $X_1$ and each $X_2$ are independently a saturated or unsaturated, linear or branched hydrocarbon, wherein at least one of $X_1$ and $X_2$ is substituted with an oxidized moiety Z selected from the group consisting of:

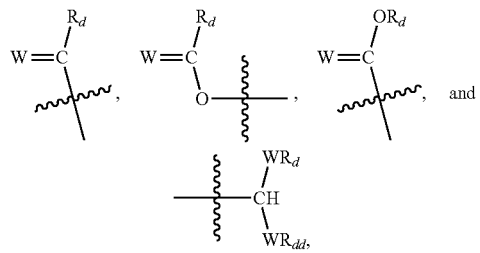

wherein W is oxygen or sulfur; and Rd and Rad are independently selected from hydrogen, alkyl, alkenyl, alkynyl, cycloalkyl, aryl, and heteroaryl.

In one embodiment in Formula III, $X_1$ and each $X_2$ independently have the general Formula IV:

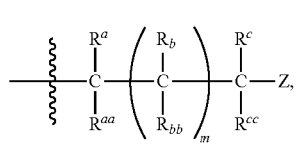

Formula IV

In Formula IV, m is an integer selected from 1 to 26.

In Formula IV, Z is selected from the group consisting of:

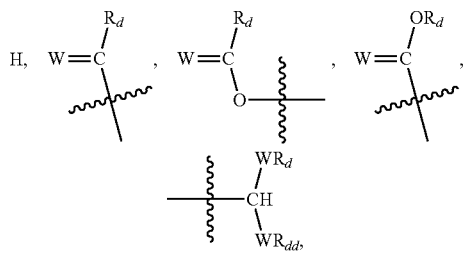

and OH, wherein W is oxygen or sulfur; and Rd and Rad are independently selected from hydrogen, alkyl, alkenyl, alkynyl, cycloalkyl, aryl, and heteroaryl, wherein at least one of $X_1$ and $X_2$ comprises a Z other than hydrogen.

In Formula III and Formula IV, $R_1$, $R_{1a}$, each $R_2$, $R_3$, $R_{3a}$, $R_a$, $R_{aa}$, each $R_b$, each $R_{bb}$, $R_c$ and $R_{cc}$ are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_1$, $R_{1a}$, $R_2$, $R_3$ and $R_{3a}$ are optionally joined to form a four-, five- or six-membered aromatic, heteroaromatic, alicyclic or heteroalicyclic ring, and wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring.

In one embodiment in Formula III, n is 1 or 2. In another embodiment in Formula III, n is 1.

In one embodiment in Formula III, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, and phosphoglycerol.

In another embodiment in Formula III, Y is selected from the group consisting of hydrogen, phosphoryl choline, and phosphoryl ethanolamine.

In another embodiment in Formula III, Y is selected from the group consisting of phosphoryl choline, and phosphoryl ethanolamine.

In one embodiment in Formula III, Y is phosphoryl choline.

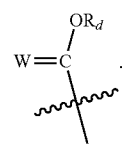

In one embodiment in Formula III, Z is In another embodiment in Formula III, Z is a carboxylic acid group.

In a further embodiment in Formula III, n is 1 and Y is phosphoryl choline.

In a further embodiment in Formula III, each of $B_1$, $B_2$, and $B_3$ is oxygen.

In a further embodiment in Formula III, n is 1, Y is phosphoryl choline, and each of $B_1$, $B_2$, and $B_3$ is oxygen.

In one embodiment, the oxidized phospholipid useful in any of the methods of the present disclosure has a structure according to Formula IIIa:

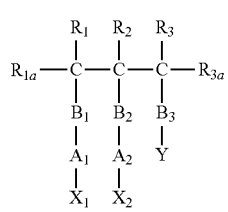

Formula IIIa or a pharmaceutically acceptable salt, hydrate or solvate thereof.

In Formula IIIa, $B_1$, $B_2$, and $B_3$ are independently selected from oxygen and sulfur.

In Formula IIIa, $A_1$ and $A_2$ are independently selected from the group consisting of $CH_2$, $CH=CH$, $C=O$ and $C=S$.

In Formula IIIa, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, and phosphoglycerol.

In Formula IIIa, $R_1$, $R_{1a}$, $R_2$, $R_3$, and $R_{3a}$, are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_1$, $R_{1a}$, $R_2$, $R_3$ and $R_{3a}$ are optionally joined to form a four-, five- or six-membered aromatic, heteroaromatic, alicyclic or heteroalicyclic ring, and wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring;

In Formula IIIa, $X_1$ and $X_2$ are independently a saturated or unsaturated, linear or branched hydrocarbon, wherein at least one of $X_1$ and $X_2$ is substituted with an oxidized moiety Z having a formula selected from:

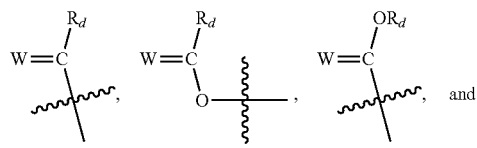

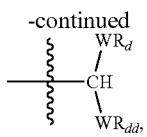

wherein W is oxygen or sulfur; and $R_d$ and $R_{dd}$ are independently selected from hydrogen, alkyl, alkenyl, alkynyl, cycloalkyl, aryl, and heteroaryl.

In one embodiment in Formula IIIa, $X_1$ and $X_2$ independently have a structure according to Formula IVa:

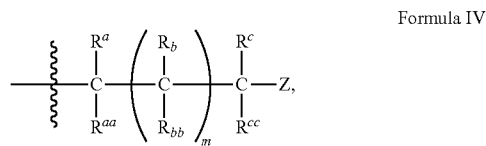

Formula IV

In Formula IVa, m is an integer selected from 1 to 26.

In Formula IVa, $R_a$, $R_{aa}$, each $R_b$, each $R_{bb}$, $R_c$, and $R_{cc}$ are independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, wherein at least two of $R_a$, $R_{aa}$, $R_b$, $R_{bb}$, $R_c$, and $R_{cc}$ are optionally joined to form a four-, five- or six-membered aromatic, heteroaromatic, alicyclic or heteroalicyclic ring.

In Formula IVa, Z is selected from the group consisting of:

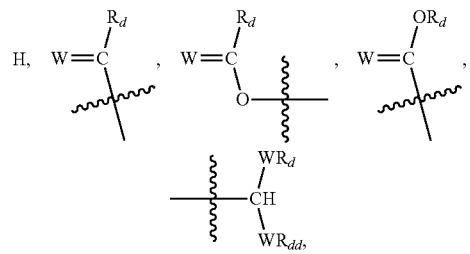

and $OR_d$, wherein W is oxygen or sulfur; and $R_d$ and $R_{dd}$ are independently selected from hydrogen, alkyl, alkenyl, alkynyl, cycloalkyl, aryl, and heteroaryl, wherein at least one of $X_1$ and $X_2$ comprises a Z other than hydrogen.

In one embodiment in Formula IIIa, Z is

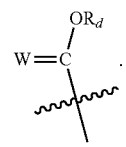

In another embodiment in Formula IIIa, Z is a carboxylic acid group.

In one embodiment in Formula IIIa, Y is selected from the group consisting of hydrogen, acyl, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-glutaric acid, phosphoethanolamine-N-[methoxy(propylene glycol)], phosphoinositol-4-phosphate, phosphoinositol-4,5-bisphosphate, phosphoethanolamine-diethylenetriamine-pentaacetate, dinitrophenyl-phosphoethanolamine, and phosphoglycerol.

In one embodiment in Formula IIIa, Y is selected from the group consisting of hydrogen, phosphoryl choline, and phosphoryl ethanolamine.

In another embodiment in Formula IIIa, Y is selected from the group consisting of phosphoryl choline, and phosphoryl ethanolamine.

In one embodiment in Formula IIIa, Y is phosphoryl choline.

In a further embodiment in Formula IIIa, each of $B_1$, $B_2$, and $B_3$ is oxygen.

In a further embodiment in Formula IIIa, Y is phosphoryl choline, and each of $B_1$, $B_2$, and $B_3$ is oxygen.

In one embodiment in Formula IIIa, the oxidized phospholipid has a structure according to Formula V:

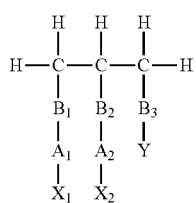

Formula V wherein $B_1$, $B_2$, $B_3$, $A_1$, $A_2$, $X_1$, $X_2$, and Y are defined as for Formula IIIa.

In one embodiment, each of $B_1$, $B_2$, $B_3$ in Formula V is oxygen and the oxidized phospholipid has a structure according to the Formula VI:

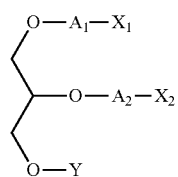

Formula VI

In Formula VI, $A_1$ is selected from the group consisting of $CH_2$, CH=CH and C=O. In one example, $A_1$ in Formula VI is $CH_2$.

In Formula VI, $A_2$ is absent or $CH_2$.

In Formula VI, $X_1$ is an alkyl having from 1 to 30 carbon atoms.

In Formula VI, $X_2$ is

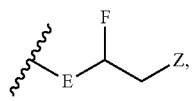

wherein
E is absent or is an alkyl chain having from 1 to 24 carbon atoms;
F is selected from the group consisting of hydrogen, hydroxy, alkyl, alkoxy, halide, acetoxy and aryl; and Z is selected from the group consisting of:

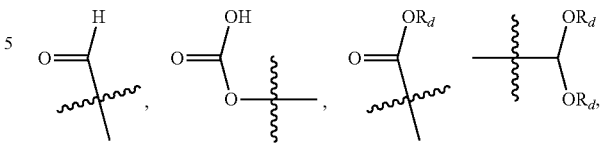

and —$OR_d$, wherein $R_d$ is selected from H, alkyl and aryl.

In Formula VI, Y is selected from the group consisting of hydrogen, alkyl, aryl, phosphoric acid, phosphoryl choline, phosphoryl ethanolamine, phosphoryl serine, phosphatidyl choline, phosphatidyl ethanolamine, phosphatidyl serine, phosphatidyl cardiolipin, phosphatidyl inositol, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-bisphosphate, pyrophosphate, phosphoethanolamine-diethylenetriamine-pentaacetate, dinitrophenyl-phosphoethanolamine, phosphoglycerol.

In one embodiment in Formula VI, $X_1$ is alkyl having from 10 to 30 carbon atoms, or from 8 to 30 carbon atoms.

In one embodiment in Formula VI, E is alkyl having from 1 to 10 carbon atoms, or from 1 to 4 carbon atoms.

In one embodiment in Formula VI, Y is phosphoryl choline.

Each carbon atom in Formula I, II, III, Ma, V, and VI is a chiral or non-chiral carbon atom, wherein each chiral carbon atom can have an S-configuration or R-configuration.

In one preferred embodiment, the oxidized phospholipid is 1-hexadecyl-2-(4'-carboxy)butyl-glycero-3-phosphocholine. In another preferred embodiment, the oxidized phospholipid is (R)-1-hexadecyl-2-(4'-carboxy)butyl-sn-glycero-3-phosphocholine.

In one preferred embodiment, the oxidized phospholipid is

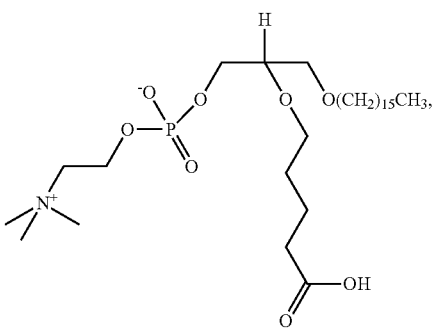

or a pharmaceutically acceptable salt thereof.

In one preferred embodiment, the oxidized phospholipid is

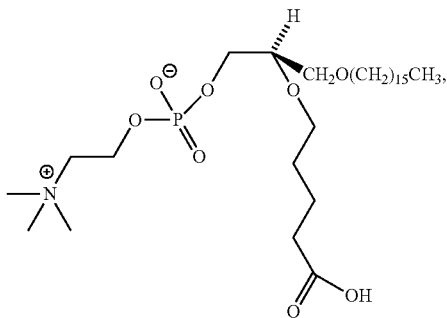

or a pharmaceutically acceptable salt thereof.

The small molecule MOSPD2 inhibitor described herein can be used alone, as a single agent, in any of the methods described herein or it can be used in combination with another agent (e.g., another MOSPD2 inhibitor or an anti-cancer drug).

VB-201 inhibits human monocyte chemotaxis in vitro and signaling pathways activated downstream of chemokine receptors. In contrast, VB-221, a derivative of VB-201, does not inhibit chemokine-induced signaling and migration in human monocytes. It was also found that ovalbumin labeled VB-201 binds and precipitates MOSPD2 from cell lysate of human CD14 monocytes. Further, HEK293 cells transfected with hemagglutinin (HA)-tagged human MOSPD2 and positively stained for HA have a strong binding to ovalbumin labeled VB-201, but not to ovalbumin labeled VB-221. These experiments and others demonstrate that 1) VB-201 binds MOSPD2; 2) that VB-201 inhibits cell chemotaxis and chemotaxis-mediated downstream pathways; and 3) that addition of VB-201 yields the same signaling effects as silencing of MOSPD2.

In any of the embodiments described herein, useful small molecule MOSPD2 inhibitors include those that are more potent inhibitors of MOSPD2 (e.g., human MOSPD2 on the cell surface of a monocyte or cancer cell) when compared to VB-221, e.g., those having a lower $IC_{50}$ value compared to that of VB-221. More preferably, useful small molecule MOSPD2 inhibitors include those that are equal or more potent inhibitors of MOSPD2 (e.g., human MOSPD2 on the cell surface of a monocyte or cancer cell) when compared to VB-201, e.g., those having a lower $IC_{50}$ value compared to that of VB-201. As understood by those skilled in the art, an $IC_{50}$ value indicates how much of a particular drug or other substance (inhibitor) is needed to inhibit a given biological process (or component of a process, i.e. an enzyme, cell, cell receptor or microorganism) by half. Methods for determining $IC_{50}$ values are known in the art.

When a small molecule MOSPD2 inhibitor (as described herein) in a pharmaceutical composition is administered to a subject alone as a single agent or in combination with another agent, the small molecule MOSPD2 inhibitor (e.g., VB-201) is present in an amount such that the administration causes at least 10% (e.g., at least 20%, at least 30%, at least 40%, at least 50%, at least 60%, at least 70%, at least 80%, at least 90%, at least 95%, at least 99%, or higher) inhibition of one or more activities of MOSPD2 (e.g., human MOSPD2) (e.g., MOSPD2 expression, cancer cell migration, monocyte migration associated with tumor growth (e.g., presence of tumor associated macrophages), a chemokine signaling pathway, a growth factor signaling pathway, EGF receptor phosphorylation, ERK phosphorylation, AKT phosphorylation, and/or FAK phosphorylation). In some embodiments, administration of the small molecule MOSPD2 inhibitor to a human subject causes at least 10% (e.g., at least 20%, at least 30%, at least 40%, at least 50%, at least 60%, at least 70%, at least 80%, at least 90%, at least 95%, at least 99%, or higher) inhibition of one or more activities of a human MOSPD2. In one aspect, administration of the small molecule MOSPD2 inhibitor causes from about 10% to 100%, from about 10% to about 99%, from about 10% to about 95%, from about 10% to about 90%, from about 10% to about 85%, from about 10% to about 80%, from about 10% to about 70%, from about 20% to about 99%, from about 20% to about 95%, from about 20% to about 90%, from about 20% to about 85%, from about 20% to about 80%, from about 30% to about 95%, from about 30% to about 90%, from about 30% to about 85%, from about 30% to about 80%, from about 40% to about 95%, from about 40% to about 90%, from about 40% to about 85%, from about 40% to about 80%, from about 50% to about 95%, from about 50% to about 90%, from about 50% to about 85%, from about 50% to about 80%, from about 60% to about 95%, from about 60% to about 90%, from about 60% to about 85%, or from about 60% to about 80% inhibition of one or more activities of MOSPD2, e.g., regulation of cancer cell migration, monocyte migration associated with tumor growth, presence of tumor associated macrophages, chemokine signaling pathways, growth factor signaling pathways, EGF receptor phosphorylation, ERK phosphorylation, AKT phosphorylation, and/or FAK phosphorylation. Preferably, the small molecule MOSPD2 inhibitor is VB-201.

In some embodiments, an inhibitor of a given protein inhibits the protein by binding to the protein and/or to an oligonucleotide (e.g., mRNA) encoding the protein.

In other embodiments, the MOSPD2 inhibitor is (i) an isolated binding molecule that specifically binds to a MOSPD2 polypeptide, (ii) an isolated binding molecule that specifically binds to a ligand of a MOSPD2 polypeptide, (iii) an antisera raised against a MOSPD2 polypeptide, (iv) a soluble MOSPD2 polypeptide, or (v) a soluble MOSPD2 polypeptide comprising, consisting essentially of, or consisting of an extracellular domain of a MOSPD2 polypeptide.

In still other embodiments, the inhibitor is an antibody that specifically binds to a MOSPD2 polypeptide. In other embodiments, the inhibitor is an antigen binding fragment of an antibody that specifically binds to a MOSPD2 polypeptide. In other embodiments, the antibody is a polyclonal, monoclonal, murine, human, humanized, chimeric, or single chain antibody. In other embodiments, the antigen binding fragment is a Fab, Fab', F(ab')$_2$, Fv, scFv, sdFv fragment, VH domain, or VL domain.

In some embodiments, an antibody or antigen binding fragment thereof described herein, which specifically binds to MOSPD2 (e.g., human MOSPD2), comprises a VH, a VL, or a VH and VL. In other embodiments, the antibody or antigen binding fragment thereof comprises a constant region.

In some embodiments, the VH, VL, or VH and VL comprise one or more complementarity determining regions (CDRs). In some embodiments, the VH comprises CDR1, CDR2, CDR3, or any combination thereof. In some embodiments, the VL comprises CDR1, CDR2, CDR3, or any combination thereof.

In some embodiments, the VH, VL, or VH and VL comprise one or more framework regions (FRs). In some embodiments, the VH comprises FR1, FR2, FR3, FR4, or any combination thereof. In some embodiments, the VL comprises FR1, FR2, FR3, FR4, or any combination thereof.

In a particular embodiment, an antibody or antigen binding fragment thereof described herein, which specifically binds to MOSPD2 (e.g., human MOSPD2), comprises a VH comprising CDR1, CDR2, and CDR3, and a VL comprising CDR1, CDR2, and CDR3.

In other embodiments, the antibodies or antigen binding fragments thereof comprise a constant region. In some embodiments, the constant region of the light chain comprises the amino acid sequence of a human kappa light chain constant region or a human lambda light chain constant region. In some embodiments, the constant region of the heavy chain comprises the amino acid sequence of a human gamma heavy chain constant region. Non-limiting examples of human constant region sequences have been described, e.g., see U.S. Pat. No. 5,693,780 and Kabat, E A et al., (1991). In some embodiments, the constant region amino acid sequence has been modified (e.g., one, two or more amino acid substitutions) such that it has at least 90%, at least 95%, at least 96%, at least 97%, at least 98%, or at least 99% sequence identity to a native human sequence. In another aspect, provided herein are antibodies or antigen binding fragments thereof that recognize or bind to an epitope of MOSPD2 (e.g., an epitope of human MOSPD2). In another aspect, provided herein are antibodies or antigen binding fragments thereof that recognize or bind to the same epitope or an overlapping epitope of MOSPD2 (e.g., human MOSPD2) as an antibody described herein (e.g., an antibody described in Example 1 or 8). In another aspect, the antibodies or antigen binding fragments thereof recognize more than one epitope of MOSPD2 (e.g., two, three, four, five or six epitopes).

In certain embodiments, an epitope of MOSPD2 can be determined by one or more methods described in the literature, e.g., NMR spectroscopy, X-ray diffraction crystallography studies, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping). For X-ray crystallography, crystallization can be accomplished using methods described in the literature (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody: antigen crystals can be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using methods described in the literature. See, e.g., Champe M et al., (1995) szpra and Cunningham B C & Wells J A (1989) szpra for a description of mutagenesis techniques, including alanine scanning mutagenesis techniques. In a specific embodiment, an epitope of an antibody or antigen binding fragment thereof is determined using alanine scanning mutagenesis studies. Epitope characterization of an antibody can also be determined by the methods provided in Ravn et al., Journal of Biological Chemistry 288: 19760-19772 (2013).

In addition, antibodies or antigen binding fragments thereof that recognize or bind to the same or overlapping epitopes of MOSPD2 (e.g., human MOSPD2) can be identified using routine techniques such as an immunoassay, for example, by showing the ability of one antibody to block the binding of another antibody to a target antigen, i.e., a competitive binding assay. Competitive binding can be determined in an assay in which the immunoglobulin under test inhibits specific binding of a reference antibody to a common antigen, such as MOSPD2. Numerous types of competitive binding assays have been described, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using 1-125 label (see Morel G A et al., (1988) Mol Immunol 25(1): 7-15); solid phase direct biotin-avidin EIA (Cheung R C et al., (1990) Virology 176: 546-52); and direct labeled RIA (Moldenhauer G et al., (1990) Scand J Immunol 32: 77-82). Typically, such an assay involves the use of purified antigen (e.g., MOSPD2 such as human MOSPD2) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors szpra, pp. 386-389.

In one embodiment, a competition assay is performed using surface plasmon resonance (BIAcore®), e.g., by an "in tandem approach" such as that described by Abdiche Y N et al., (2009) Analytical Biochem 386: 172-180, whereby MOSPD2 antigen is immobilized on the chip surface, for example, a CMS sensor chip and the anti-MOSPD2 antibodies are then run over the chip. To determine if an antibody or antigen binding fragment thereof competes with an anti-MOSPD2 antibody or antigen binding fragment thereof described herein, the anti-MOSPD2 antibody or antigen binding fragment thereof is first run over the chip surface to achieve saturation and then the potential, competing antibody is added. Binding of the competing antibody can then be determined and quantified relative to a non-competing control.

In certain aspects, competition binding assays can be used to determine whether an antibody or antigen binding fragment thereof is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody or antigen binding fragment thereof can be tested in competition binding assays with an antibody described herein (e.g., those in Example 1 or 8), or a chimeric or Fab antibody thereof, or an antibody comprising VH CDRs and VL CDRs of an antibody described herein (e.g., those in Example 1 or 8).

Accordingly, in a certain aspect, provided herein are antibodies or antigen binding fragments thereof that compete (e.g., in a dose dependent manner) for binding to MOSPD2 (e.g., human MOSPD2) with an antibody described herein (e.g., Example 1 or 8), as determined using assays known to one of skill in the art or described herein (e.g., ELISA competitive assays, surface plasmon resonance or Scatchard analysis).

In some embodiments, anti-MOSPD2 antibodies or antigen binding fragments thereof of the invention specifically bind to one or more of the following amino acid regions (epitopes) of MOSPD2, numbered according to SEQ ID NO:1 (amino acid residues 1-518): 508-517, 501-514, 233-241, 509-517, 212-221, 13-24, 505-517, 505-514, 89-100, 506-517, 233-245, 504-514, 128-136, 218-226, 15-24, 83-96, 42-50, 462-474, 340-351, 504-517, 462-470, 327-337, 21-32, 217-226, 510-517, 178-190, 497-509, 504-516, 64-77, 504-515, 147-159, 503-315, 88-97, 208-218, 178-191, 502-515, 503-516, 497-505, 500-509, 189-202, 189-197, 505-516, 1-63, 82-239, 93-234, 327-445, 327-431, and 497-517.

In some embodiments, anti-MOSPD2 antibodies or antigen binding fragments thereof of the invention specifically bind to one or more of the following amino acid regions (epitopes) of MOSPD2, numbered according to SEQ ID NO:1 (amino acid residues 1-518): about 508 to about 517, about 501 to about 514, about 233 to about 241, about 509 to about 517, about 212 to about 221, about 13 to about 24, about 505 to about 517, about 505 to about 514, about 89 to about 100, about 506 to about 517, about 233 to about 245, about 504 to about 514, about 128 to about 136, about 218 to about 226, about 15 to about 24, about 83 to about 96, about 42 to about 50, about 462 to about 474, about 340 to about 351, about 504 to about 517, about 462 to about 470, about 327 to about 337, about 21 to about 32, about 217 to about 226, about 510 to about 517, about 178 to about 190, about 497 to about 509, about 504 to about 516, about 64 to about 77, about 504 to about 515, about 147 to about 159, about 503 to about 515, about 88 to about 97, about 208 to about 218, about 178 to about 191, about 502 to about 515, about 503 to about 516, about 497 to about 505, about 500 to about 509, about 189 to about 202, about 189 to about 197, about 505 to about 516, about 1 to about 63, about 82 to about 239, about 93 to about 234, about 327 to about 445, about 327 to about 431, and about 497 to about 517.

In some embodiments, anti-MOSPD2 antibodies or antigen binding fragments thereof of the invention specifically bind to one or more of the following amino acid regions (epitopes) of MOSPD2, numbered according to SEQ ID NO:1 (amino acid residues 1-518): about 505 to about 515, about 500 to about 515, about 230 to about 240, about 510 to about 520, about 210 to about 220, about 15 to about 25, about 505 to about 520, about 505 to about 515, about 90 to about 100, about 505 to about 525, about 230 to about 245, about 505 to about 510, about 130 to about 140, about 220 to about 230, about 15 to about 30, about 80 to about 95, about 40 to about 50, about 460 to about 475, about 340 to about 350, about 500 to about 515, about 460 to about 470, about 325 to about 335, about 20 to about 35, about 215 to about 225, about 510 to about 520, about 175 to about 190, about 500 to about 510, about 505 to about 530, about 60 to about 75, about 500 to about 520, about 145 to about 160, about 502 to about 515, about 85 to about 100, about 205 to about 220, about 175 to about 190, about 500 to about 505, about 500 to about 525, about 495 to about 505, about 495 to about 510, about 190 to about 200, about 190 to about 198, about 502 to about 515, about 1 to about 60, about 80 to about 240, about 90 to about 235, about 330 to about 445, about 330 to about 430, and about 495 to about 515.

In some embodiments, antibodies or antigen binding fragments of the invention bind to MOSPD2 with an antibody-antigen equilibrium dissociation constant ($K_D$) of from about $10^{-6}$ M to about $10^{-12}$ M, or any range of values thereof (e.g., from about $10^{-7}$ M to about $10^{-12}$, from $10^{-8}$ M to about $10^{-12}$ M, from about $10^{-9}$ M to about $10^{-12}$ M, from about $10^{-10}$ M to about $10^{-12}$ M, from about $10^{-11}$ M to about $10^{-12}$ M, from about $10^{-6}$ M to about $10^{-11}$ M, from about $10^{-7}$ M to about $10^{-11}$ M, from about $10^{-8}$ M to about $10^{-11}$ M, from about $10^{-9}$ M to about $10^{-11}$ M, from about $10^{-10}$ M to about $10^{-11}$ M, from about $10^{-6}$ M to about $10^{-10}$ M, from about $10^{-7}$ M to about $10^{-10}$ M, from about $10^{-8}$ M to about $10^{-10}$ M, from about $10^{-9}$ M to about $10^{-10}$ M, from about $10^{-6}$ M to about $10^{-9}$ M, from about $10^{-7}$ M to about $10^{-9}$ M, from about $10^{-8}$ M to about $10^{-9}$ M, from about $10^{-6}$ M to about $10^{-8}$ M, or from about $10^{-7}$ M to about $10^{-8}$). In other embodiments, the antibody or antigen binding fragment thereof has a $K_D$ of about $10^{-6}$ M, about $10^{-7}$ M, about $10^{-8}$ M, about $10^{-9}$ M, about $10^{-10}$ M, about $10^{-11}$ M, or about $10^{-12}$ M. In some embodiments, the antibody or antigen binding fragment binds to one or more epitopes on MOSPD2. In some embodiments, the $K_D$ is determined by Scatchard analysis, surface plasmon resonance, or other method described herein, in some embodiments, at 37° C.

In some embodiments, antibodies or antigen binding fragments of the invention bind to MOSPD2 with a $K_{on}$ of from about $10^3$ 1/Ms to about $10^6$ 1/Ms, or any range of values thereof (e.g., from about $10^3$ 1/Ms to about $10^5$ 1/Ms, from about $10^4$ 1/Ms to about $10^5$ 1/Ms, from about $10^4$ 1/Ms to about $10^6$ 1/Ms, from about $10^5$ 1/Ms to about $10^6$ 1/Ms, or from about $10^3$ 1/Ms to about $10^4$ 1/Ms). In other embodiments, the antibody or antigen binding fragment has a $K_{on}$ of about $10^3$ 1/Ms, about $10^4$ 1/Ms, about $10^5$ 1/Ms, or about $10^6$ 1/Ms.

In some embodiments, antibodies or antigen binding fragments of the invention bind to MOSPD2 with a $K_{off}$ of from about $10^{-3}$ 1/s to about $10^{-6}$ 1/s, or any range of values thereof (e.g., from about $10^{-3}$ 1/s to about $10^{-5}$ 1/s, from about $10^{-4}$ 1/s to about $10^{-5}$ 1/s, from about $10^{-4}$ 1/s to about $10^{-6}$ 1/s, from about $10^{-5}$ 1/s to about $10^{-6}$ 1/s, or from about $10^{-3}$ 1/s to about $10^{-4}$ 1/s). In other embodiments, the antibody or antigen binding fragment has a $K_{off}$ of about $10^{-3}$ 1/s, about $10^{-4}$ 1/s, about $10^{-5}$ 1/s, or about $10^{-6}$ 1/s.

In still other embodiments, the inhibitor of MOSPD2 is an RNAi, miRNA, siRNA, shRNA, an antisense RNA, an antisense DNA, a decoy molecule, a decoy DNA, a double-stranded DNA, a single-stranded DNA, a complexed DNA, an encapsulated DNA, a viral DNA, a plasmid DNA, a naked RNA, an encapsulated RNA, a viral RNA, a double-stranded RNA, a molecule capable of generating RNA interference, or combinations thereof. In some embodiments, the inhibitor hybridizes to a nucleotide sequence encoding a MOSPD2 polypeptide. In some embodiments, the hybridization is under a stringent condition or under a highly stringent condition.

In some embodiments, the inhibitor is a clustered regularly interspaced short palindromic repeats CRISPR-CAS9 system.

In further embodiments, a MOSPD2 polypeptide has a sequence at least about 75%, at least about 80%, at least about 85%, at least about 90%, at least about 95%, at least about 96%, at least about 97%, at least about 98%, at least about 99%, or 100% identical to any one of SEQ ID NOs:1-4. In other embodiments, the MOSPD2 polypeptide has a sequence at least 75%, at least 80%, at least 85%, at least 90%, at least 95%, at least 96%, at least 97%, at least 98%, or at least 99% identical to any one of SEQ ID NOs:1-4. In other embodiments, the MOSPD2 polypeptide has a sequence of about 75%, about 80%, about 85%, about 90%, about 95%, about 96%, about 97%, about 98%, or about 99% identical to any one of SEQ ID NOs:1-4. In other embodiments, the MOSPD2 polypeptide has a sequence with 75%, 80%, 85%, 90%, 95%, 96%, 97%, 98%, or 99% identity to any one of SEQ ID NOs:1-4. In other embodiments, the MOSPD2 polypeptide has a sequence with from about 75% to 100% identity to any one of SEQ ID NOs:1-4, or any range of values thereof, for example, from about 80% to 100% identity, from about 85% to 100% identity, from about 90% to 100% identity, from about 95% to 100% identity, from about 96% to 100% identity, from about 97% to 100% identity, from about 98% to 100% identity, from about 99% to about 100% identity, from about 75% to about 99% identity, from about 80% to about 99% identity, from about 85% to about 99% identity, from about 90% to about 99% identity, from about 95% to about 99% identity, from about 96% to about 99% identity, from about 97% to about 99% identity, from about 98% to about 99% identity, from about 99% to about 100% identity, from about 75% to about 95% identity, from about 80% to about 95% identity, from about 85% to about 95% identity, or from about 90% to about 95% identity to any one of SEQ ID NOs:1-4.

In further embodiments of the invention, the MOSPD2 polypeptide is encoded by a polynucleotide sequence having at least about 75%, at least about 80%, at least about 85%, at least about 90%, at least about 95%, at least about 96%, at least about 97%, at least about 98%, at least about 99%, or 100% identity to any one of SEQ ID NOs:5-8. In other embodiments, the MOSPD2 polypeptide is encoded by a polynucleotide sequence having at least 75%, at least 80%, at least 85%, at least 90%, at least 95%, at least 96%, at least 97%, at least 98%, or at least 99% identity to any one of SEQ ID NOs:5-8. In other embodiments, the MOSPD2 polypeptide is encoded by a polynucleotide sequence having about 75%, about 80%, about 85%, about 90%, about 95%, about 96%, about 97%, about 98%, or about 99% identity to any one of SEQ ID NOs:5-8. In other embodiments, the MOSPD2 polypeptide is encoded by a polynucleotide sequence 75%, 80%, 85%, 90%, 95%, 96%, 97%, 98%, or 99% identical to any one of SEQ ID NOs:1-4. In other embodiments, the MOSPD2 polypeptide is encoded by a polynucleotide sequence having from about 75% to 100% identity to any one of SEQ ID NOs:5-8, or any range of values thereof, for example, from about 80% to 100% identity, from about 85% to 100% identity, from about 90% to 100% identity, from about 95% to 100% identity, from about 96% to 100% identity, from about 97% to 100% identity, from about 98% to 100% identity, from about 99% to about 100% identity, from about 75% to about 99% identity, from about 80% to about 99% identity, from about 85% to about 99% identity, from about 90% to about 99% identity, from about 95% to about 99% identity, from about 96% to about 99% identity, from about 97% to about 99% identity, from about 98% to about 99% identity, from about 99% to about 100% identity, from about 75% to about 95% identity, from about 80% to about 95% identity, from about 85% to about 95% identity, or from about 90% to about 95% identity to any one of SEQ ID NOs:5-8.

In any of the embodiments described herein, an inhibitor of MOSPD2 can be an inhibitor of MOSPD2 expressed by a cancer cell, e.g., a human cancer cell. Non-exclusive listing of types of cancer cells include cells of bladder cancer, breast cancer, colon cancer, rectal cancer, kidney cancer, liver cancer, lung cancer, esophageal cancer, gallbladder cancer, ovarian cancer, pancreatic cancer, stomach cancer, cervical cancer, thyroid cancer, prostate cancer, skin cancer, hematopoietic cancer, cancer of mesenchymal origin, cancer of central or peripheral nervous system, endometrial cancer, head and neck cancer, glioblastoma, and malignant ascites. In some embodiments, the cancer is a small cell lung cancer or a non-small-cell lung cancer. In some embodiments, the cancer is skin cancer, e.g., squamous cell carcinoma, basal cell cancer, melanoma, dermatofibrosarcoma protuberans, Merkel cell carcinoma, Kaposi's sarcoma, keratoacanthoma, spindle cell tumors, sebaceous carcinomas, microcystic adnexal carcinoma, Paget's disease of the breast, atypical fibroxanthoma, leiomyosarcoma, or angiosarcoma. In some embodiments, the cancer is a hematopoietic cancer of lymphoid lineage, e.g., leukemia, acute lymphocytic leukemia, chronic lymphocytic leukemia, acute lymphoblastic leukemia, B-cell lymphoma, T-cell-lymphoma, Hodgkin's lymphoma, non-Hodgkin's lymphoma, hairy cell lymphoma or Burkitt's lymphoma. In some embodiments, the cancer is a hematopoietic cancer of myeloid lineage, e.g., fibrosarcoma, rhabdomyosarcoma, soft tissue sarcoma, or bone sarcoma. In some embodiments, the cancer is a cancer of the central or peripheral nervous system, e.g., astrocytoma, neuroblastoma, glioma, or schwannomas. In some embodiments, the cancer is anal cancer, bone cancer, gastrointestinal stomal cancer, gestational trophoblastic disease, Hodgkin's lymphoma, Kaposi sarcoma, keratoacanthoma, malignant mesothelioma, multicentric castleman disease, multiple myeloma and other plasma cell neoplasms, myeloproliferative neoplasms, neuroblastoma, non-Hodgkin's lymphoma, osteosarcoma, ovarian, fallopian tube, or primary peritoneal cancer, penile cancer, retinoblastoma, rhabdomyosarcoma, seminoma, soft tissue sarcoma, stomach (gastric) cancer, testicular cancer, teratocarcinoma, thyroid follicular cancer, vaginal cancer, vulvar cancer, Wilms tumor and other childhood kidney cancers, and xeroderma pigmentosum. In some embodiments, the cancer is bladder cancer, brain cancer (e.g., cerebrum astrocytoma), breast cancer, colon cancer (e.g., colon adenocarcinoma), esophageal cancer (e.g., esophageal adenocarcinoma), lung cancer, skin cancer (e.g., melanoma), tongue cancer (e.g., head and neck (tongue) cell carcinoma), kidney cancer (e.g., kidney clear cell carcinoma), or hepatic cancer (e.g., hepatocellular carcinoma).

Pharmaceutical Compositions

Other embodiments of the invention relate to a pharmaceutical composition comprising an inhibitor of MOSPD2, e.g., MOSPD2 expressed by a cancer cell. In some embodiments, the pharmaceutical composition comprises an inhibitor of MOSPD2, e.g., MOSPD2 expressed by a cancer cell and a pharmaceutically acceptable carrier. In other embodiments, the pharmaceutical composition comprises a therapeutically effective amount of the inhibitor of MOSPD2, e.g., MOSPD2 expressed by a cancer cell. Exemplary inhibitors of MOSPD2 are described herein. Suitable types of cancer are also described herein.

In other embodiments, the inhibitor of MOSPD2 is an antibody or antigen binding fragment of an antibody, and the therapeutically effective amount is from about 1 µg/ml to about 10 µg/ml, or any range of values thereof (e.g., from about 2 µg/ml to about 10 µg/ml, from about 3 µg/ml to about 10 µg/ml, from about 4 µg/ml to about 10 µg/ml, from about 5 µg/ml to about 10 µg/ml, from about 6 µg/ml to about 10 µg/ml, from about 7 µg/ml to about 10 µg/ml, from about 8 µg/ml to about 10 µg/ml, from about 9 µg/ml to about 10 µg/ml, from about 1 µg/ml to about 9 µg/ml, from about 2 µg/ml to about 9 µg/ml, from about 3 µg/ml to about 9 µg/ml, from about 4 µg/ml to about 9 µg/ml, from about 5 µg/ml to about 9 µg/ml, from about 6 µg/ml to about 9 µg/ml, from about 7 µg/ml to about 9 µg/ml, from about 8 µg/ml to about 9 µg/ml, from about 1 µg/ml to about 8 µg/ml, from about 2 µg/ml to about 8 µg/ml, from about 3 µg/ml to about 8 µg/ml, from about 4 µg/ml to about 8 µg/ml, from about 5 µg/ml to about 8 µg/ml, from about 6 µg/ml to about 8 µg/ml, from about 7 µg/ml to about 8 µg/ml, from about 1 µg/ml to about 7 µg/ml, from about 2 µg/ml to about 7 µg/ml, from about 3 µg/ml to about 7 µg/ml, from about 4 µg/ml to about 7 µg/ml, from about 5 µg/ml to about 7 µg/ml, from about 6 µg/ml to about 7 µg/ml, from about 1 µg/ml to about 6 µg/ml, from about 2 µg/ml to about 6 µg/ml, from about 3 µg/ml to about 6 µg/ml, from about 4 µg/ml to about 6 µg/ml, from about 5 µg/ml to about 6 µg/ml, from about 1 µg/ml to about 5 µg/ml, from about 2 µg/ml to about 5 µg/ml, from about 3 µg/ml to about 5 µg/ml, from about 4 µg/ml to about 5 µg/ml, from about 1 µg/ml to about 4 µg/ml, from about 2 µg/ml to about 4 µg/ml, from about 3 µg/ml to about 4 µg/ml, from about 1 µg/ml to about 3 µg/ml, from about 2 µg/ml to about 3 µg/ml, or from about 1 µg/ml to about 2 µg/ml). In other embodiments, the inhibitor of MOSPD2 is an antibody or antigen binding fragment of an antibody, and the therapeutically effective amount is about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, or about 10 µg/ml.

In some embodiments, the inhibitor of MOSPD2 is an antibody or antigen binding fragment of an antibody, and the therapeutically effective amount is from about 10 mg/kg to about 40 mg/kg, or any range of values thereof (e.g., from about 15 mg/kg to about 40 mg/kg, from about 20 mg/kg to about 40 mg/kg, from about 25 mg/kg to about 40 mg/kg, from about 30 mg/kg to about 40 mg/kg, from about 35 mg/kg to about 40 mg/kg, from about 10 mg/kg to about 35 mg/kg, from about 15 mg/kg to about 35 mg/kg, from about 20 mg/kg to about 35 mg/kg, from about 25 mg/kg to about 35 mg/kg, from about 30 mg/kg to about 35 mg/kg, from about 10 mg/kg to about 30 mg/kg, from about 15 mg/kg to about 30 mg/kg, from about 20 mg/kg to about 30 mg/kg, from about 25 mg/kg to about 30 mg/kg, from about 10 mg/kg to about 25 mg/kg, from about 15 mg/kg to about 25 mg/kg, from about 20 mg/kg to about 25 mg/kg, from about 10 mg/kg to about 20 mg/kg, from about 15 mg/kg to about 20 mg/kg, or from about 10 mg/kg to about 15 mg/kg). In other embodiments, the inhibitor of MOSPD2 is an antibody or antigen binding fragment of an antibody, and the therapeutically effective amount is about 10 mg/kg, about 15 mg/kg, about 20 mg/kg, about 25 mg/kg, about 30 mg/kg, about 35 mg/kg, or about 40 mg/kg.

In some embodiments, the inhibitor of MOSPD2 (e.g., an antibody or antigen binding fragment thereof) is present in an amount such that administration of the MOSPD2 inhibitor causes at least 10% (e.g., at least 20%, at least 30%, at least 40%, at least 50%, at least 60%, at least 70%, at least 80%, at least 90%, at least 95%, at least 99%, or higher) inhibition of one or more activities of MOSPD2 (e.g., human MOSPD2, e.g., MOSPD2 expressed by a human cancer cell) (e.g., MOSPD2 expression, cancer cell migration, monocyte migration associated with tumor growth (e.g., presence of tumor associated macrophages), a chemokine signaling pathway, a growth factor signaling pathway, EGF receptor phosphorylation, ERK phosphorylation, AKT phosphorylation, and/or FAK phosphorylation). In some embodiments, administration of the MOSPD2 inhibitor to a human subject causes at least 10% (e.g., at least 20%, at least 30%, at least 40%, at least 50%, at least 60%, at least 70%, at least 80%, at least 90%, at least 95%, at least 99%, or higher) inhibition of one or more activities of a human MOSPD2, e.g., MOSPD2 expressed by a human cancer cell.

In another aspect, administration of the MOSPD2 inhibitor (e.g., an anti-MOSPD2 antibody or antigen binding fragment thereof) causes from about 10% to 100%, from about 10% to about 99%, from about 10% to about 95%, from about 10% to about 90%, from about 10% to about 85%, from about 10% to about 80%, from about 10% to about 70%, from about 20% to about 99%, from about 20% to about 95%, from about 20% to about 90%, from about 20% to about 85%, from about 20% to about 80%, from about 30% to about 95%, from about 30% to about 90%, from about 30% to about 85%, from about 30% to about 80%, from about 40% to about 95%, from about 40% to about 90%, from about 40% to about 85%, from about 40% to about 80%, from about 50% to about 95%, from about 50% to about 90%, from about 50% to about 85%, from about 50% to about 80%, from about 60% to about 95%, from about 60% to about 90%, from about 60% to about 85%, or from about 60% to about 80% inhibition of one or more activities of MOSPD2, e.g., regulation of cancer cell migration, monocyte migration associated with tumor growth, presence of tumor associated macrophages, chemokine signaling pathways, growth factor signaling pathways, EGF receptor phosphorylation, ERK phosphorylation, AKT phosphorylation, and/or FAK phosphorylation.

As used herein, a "pharmaceutical composition" refers to a preparation of one or more agents as described herein (e.g., a MOSPD2 inhibitor, or a MOSPD2 inhibitor with one or more other agents described herein), or physiologically acceptable salts or prodrugs thereof, with other chemical components, including, but not limited to, pharmaceutically acceptable carriers, excipients, lubricants, buffering agents, antibacterial agents, bulking agents (e.g., mannitol), antioxidants (e.g., ascorbic acid or sodium bisulfite), and the like. The purpose of the pharmaceutical composition is to facilitate administration of the agent(s) to a subject.

As used herein, "administration" or "administering" to a subject includes, but is not limited to, the act of a physician or other medical professional prescribing a pharmaceutical composition of the invention for a subject. Administration can be local administration, e.g., intra-tumor administration.

Herein, the phrase "pharmaceutically acceptable carrier" refers to a carrier or a diluent that does not cause significant irritation to the subject and does not abrogate the biological activity and properties of the agent(s) described herein.

As used herein, the term "carrier" refers to a diluent, adjuvant, excipient, or vehicle with which the therapeutic is administered.

Herein the term "excipient" refers to an inert substance added to a pharmaceutical composition to further facilitate administration of an active ingredient.

In some embodiments, a pharmaceutical composition comprising a MOSPD2 inhibitor further comprises one or more additional active agents. In some embodiments, the one or more additional active agent is an anticancer drug. In some embodiments, the one or more additional active agent is an anti-proliferative agent.

In any of the embodiments described herein, useful anticancer drugs include those known in the art, for example, those anticancer drugs approved for use by a regulatory agency such as the U.S. Food and Drug Administration (US FDA) or the like. Some of the useful anticancer drugs are listed by the U.S. National Cancer Institute at http://www.cancer.gov/about-cancer/treatment/drugs. Exemplary useful anticancer drugs include those approved (e.g., by the US FDA) for anal cancer, bladder cancer, bone cancer, brain cancer, breast cancer, cervical cancer, colon and rectal cancer, endometrial cancer, esophageal cancer, gastrointestinal stomal cancer, gestational trophoblastic disease, head and neck cancer, Hodgkin's lymphoma, Kaposi sarcoma, kidney (renal cell) cancer, leukemia, liver cancer, lung cancer, malignant mesothelioma, melanoma, multicentric castleman disease, multiple myeloma and other plasma cell neoplasms, myeloproliferative neoplasms, neuroblastoma, non-Hodgkin's lymphoma, ovarian, fallopian tube, or primary peritoneal cancer, pancreatic cancer, penile cancer, prostate cancer, retinoblastoma, rhabdomyosarcoma, skin cancer, soft tissue sarcoma, stomach (gastric) cancer, testicular cancer, thyroid cancer, vaginal cancer, vulvar cancer, and Wilms tumor and other childhood kidney cancers.

In any of the embodiments described herein, the anticancer drug can be selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Akynzeo (Netupitant and Palonosetron Hydrochloride), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPDX, Carboplatin, Carboplatin-Taxol, Carfilzomib, Carmubris (Carmustine), Carmustine, Carmustine Implant, Casodex (Bicalutamide), CeeNU (Lomustine), Ceritinib, Cerubidine (Daunorubicin Hydrochloride), Cervarix (Recombinant HPV Bivalent Vaccine), Cetuximab, Chlorambucil, Chlorambucil-Prednisone, CHOP, Cisplatin, Clafen (Cyclophosphamide), Clofarabine, CMF,Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), Folfiri, Folfiri-Bevacizumab, Folfiri-Cetuximab, Folfirinox, Folflox, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, Gemcitabine-Cisplatin, Gemcitabine-Oxaliplatin, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Netupitant and Palonosetron Hydrochloride, Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Disodium, Panitumumab, Panobinostat, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Unituxin (Dinutuximab), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

When two or more agents are administered as a pharmaceutical composition, each agent may optionally be administered in a separate composition and/or via a different route of administration. Possible routes of administration for each agent independently include, but are not limited to, parenteral administration, transmucosal administration, rectal administration, buccal administration and/or inhalation (e.g., as described herein).

In some embodiments, the pharmaceutical composition is suitable for systemic or local administration. In other embodiments, the pharmaceutical composition is suitable for nasal, oral, or intra-peritoneal administration. In other embodiments, the pharmaceutical composition is suitable for intravenous administration, intramuscular administration or subcutaneous administration. In other embodiments, the pharmaceutical composition is suitable for intra-tumor administration.

Methods of Use in Cancer and Metastasis

In some embodiments, the present invention relates to the discovery that MOSPD2 expression in cancer cells is upregulated when compared to its non-cancerous counterpart. As shown in the Examples section, MOSPD2 expression was positively identified in various types of cancer cells, e.g., bladder cancer, brain cancer (e.g., cerebrum astrocytoma), breast cancer, colon cancer (e.g., colon adenocarcinoma), esophageal cancer (e.g., esophageal adenocarcinoma), lung cancer, skin cancer (e.g., melanoma), tongue cancer (e.g., head and neck (tongue) cell carcinoma), kidney cancer (e.g., kidney clear cell carcinoma), and hepatic cancer (e.g., hepatocellular carcinoma), but not in the counterpart normal, non-cancerous cells. Further, inhibition of MOSPD2 by silencing of MOSPD2 expression or administration of anti-MOSPD2 F(ab')$_2$ mAb in various types of cancer cells inhibits migration and metastasis of cancer cells both in vitro and in vivo.

Embodiments of the invention relate to methods for treating, preventing, or reducing the incidence of metastasis of a cancer cell with an inhibitor of MOSPD2. In some embodiments, the methods include administering to a subject in need thereof an effective amount of an inhibitor of MOSPD2. In other embodiments, the MOSPD2 is expressed by the cancer cell. Exemplary MOSPD2 inhibitors include those described herein. Suitable types of cancer are also described herein. In some embodiments, the cancer is bladder cancer, brain cancer (e.g., cerebrum astrocytoma), breast cancer, colon cancer (e.g., colon adenocarcinoma), esophageal cancer (e.g., esophageal adenocarcinoma), lung cancer, skin cancer (e.g., melanoma), tongue cancer (e.g., head and neck (tongue) cell carcinoma), kidney cancer (e.g., kidney clear cell carcinoma), or hepatic cancer (e.g., hepatocellular carcinoma).

Embodiments of the invention also relate to methods of treating, preventing, or reducing the incidence of a cancer with an inhibitor of MOSPD2. In some embodiments, the methods include administering to a subject in need thereof a therapeutically effective amount of an inhibitor of MOSPD2. In other embodiments, the MOSPD2 is expressed by the cancer cells. In some embodiments, the methods further comprise administering a therapeutically effective amount of an inhibitor of MOSPD2 and another anticancer drug. Exemplary MOSPD2 inhibitors and anticancer drugs include those described herein. Suitable types of cancer are also described herein. In some embodiments, the cancer is bladder cancer, brain cancer (e.g., cerebrum astrocytoma), breast cancer, colon cancer (e.g., colon adenocarcinoma), esophageal cancer (e.g., esophageal adenocarcinoma), lung cancer, skin cancer (e.g., melanoma), tongue cancer (e.g., head and neck (tongue) cell carcinoma), kidney cancer (e.g., kidney clear cell carcinoma), or hepatic cancer (e.g., hepatocellular carcinoma).

Embodiments of the invention also relate to methods of treating, preventing, or reducing the incidence of a metastatic cancer with an inhibitor of MOSPD2. In some embodiments, the methods include administering to a subject in need thereof a therapeutically effective amount of an inhibitor of MOSPD2 and another anticancer drug. In some embodiments, the administration is local, e.g., intra-tumor administration. In some embodiments, the MOSPD2 is expressed by the metastatic cancer cells. Exemplary MOSPD2 inhibitors and anticancer drugs include those described herein. Suitable types of cancer are also described herein. In some embodiments, the cancer is bladder cancer, brain cancer (e.g., cerebrum astrocytoma), breast cancer, colon cancer (e.g., colon adenocarcinoma), esophageal cancer (e.g., esophageal adenocarcinoma), lung cancer, skin cancer (e.g., melanoma), tongue cancer (e.g., head and neck (tongue) cell carcinoma), kidney cancer (e.g., kidney clear cell carcinoma), or hepatic cancer (e.g., hepatocellular carcinoma).

In some embodiments, the inhibitor of MOSPD2 is an antibody or antigen binding fragment of an antibody described herein, e.g., having an antibody-antigen equilibrium dissociation constant ($K_D$) of from about $10^{-6}$ M to about $10^{-12}$ M, or any range of values thereof (e.g., from about $10^{-7}$ M to about $10^{-12}$, from $10^{-8}$ M to about $10^{-12}$ M, from about $10^{-9}$ M to about $10^{-12}$ M, from about $10^{-10}$ M to about $10^{-12}$ M, from about $10^{-11}$ M to about $10^{-12}$ M, from about $10^{-6}$ M to about $10^{-11}$ M, from about $10^{-7}$ M to about $10^{-11}$ M, from about $10^{-8}$ M to about $10^{-11}$ M, from about $10^{-9}$ M to about $10^{-11}$ M, from about $10^{-10}$ M to about $10^{-11}$ M, from about $10^{-6}$ M to about $10^{-10}$ M, from about $10^{-7}$ M to about $10^{-10}$ M, from about $10^{-8}$ M to about $10^{-10}$ M, from about $10^{-9}$ M to about $10^{-10}$ M, from about $10^{-6}$ M to about $10^{-9}$ M, from about $10^{-7}$ M to about $10^{-9}$ M, from about $10^{-8}$ M to about $10^{-9}$ M, from about $10^{-6}$ M to about $10^{-8}$ M, or from about $10^{-7}$ M to about $10^{-8}$). In other embodiments, the antibody or antigen binding fragment thereof has a $K_D$ of about $10^{-6}$ M, about $10^{-7}$ M, about $10^{-8}$ M, about $10^{-9}$ M, about $10^{-10}$ M, about $10^{-11}$ M, or about $10^{-12}$ M. In some embodiments, the antibody or antigen binding fragment binds to one or more epitopes on MOSPD2. In some embodiments, the $K_D$ is determined by Scatchard analysis, surface plasmon resonance, or other method described herein, in some embodiments, at 37° C.

In some embodiments, antibodies or antigen binding fragments of the invention bind to MOSPD2 with a $K_{on}$ of from about $10^3$ 1/Ms to about $10^6$ 1/Ms, or any range of values thereof (e.g., from about $10^3$ 1/Ms to about $10^5$ 1/Ms, from about $10^4$ 1/Ms to about $10^5$ 1/Ms, from about $10^4$ 1/Ms to about $10^6$ 1/Ms, from about $10^5$ 1/Ms to about $10^6$ 1/Ms, or from about $10^3$ 1/Ms to about $10^4$ 1/Ms). In other embodiments, the antibody or antigen binding fragment has a $K_{on}$ of about $10^3$ 1/Ms, about $10^4$ 1/Ms, about $10^5$ 1/Ms, or about $10^6$ 1/Ms.

In some embodiments, antibodies or antigen binding fragments of the invention bind to MOSPD2 with a $K_{off}$ of from about $10^{-3}$ 1/s to about $10^{-6}$ 1/s, or any range of values thereof (e.g., from about $10^{-3}$ 1/s to about $10^{-5}$ 1/s, from about $10^{-4}$ 1/s to about $10^{-5}$ 1/s, from about $10^{-4}$ 1/s to about $10^{-6}$ 1/s, from about $10^{-5}$ 1/s to about $10^{-6}$ 1/s, or from about $10^{-3}$ 1/s to about $10^{-4}$ 1/s). In other embodiments, the antibody or antigen binding fragment has a $K_{off}$ of about $10^{-6}$ 1/s, about $10^{-4}$ 1/s, about $10^{-5}$ 1/s, or about $10^{-6}$ 1/s.

In some embodiments, the inhibitor of MOSPD2 is an antibody or antigen binding fragment of an antibody, and the therapeutically effective amount is from about 1 µg/ml to about 10 µg/ml, or any range of values thereof (e.g., from about 2 µg/ml to about 10 µg/ml, from about 3 µg/ml to about 10 µg/ml, from about 4 µg/ml to about 10 µg/ml, from about 5 µg/ml to about 10 µg/ml, from about 6 µg/ml to about 10 µg/ml, from about 7 µg/ml to about 10 µg/ml, from about 8 µg/ml to about 10 µg/ml, from about 9 µg/ml to about 10 µg/ml, from about 1 µg/ml to about 9 µg/ml, from about 2 µg/ml to about 9 µg/ml, from about 3 µg/ml to about 9 µg/ml, from about 4 µg/ml to about 9 µg/ml, from about 5 µg/ml to about 9 µg/ml, from about 6 µg/ml to about 9 µg/ml, from about 7 µg/ml to about 9 µg/ml, from about 8 µg/ml to about 9 µg/ml, from about 1 µg/ml to about 8 µg/ml, from about 2 µg/ml to about 8 µg/ml, from about 3 µg/ml to about 8 µg/ml, from about 4 µg/ml to about 8 µg/ml, from about 5 µg/ml to about 8 µg/ml, from about 6 µg/ml to about 8 µg/ml, from about 7 µg/ml to about 8 µg/ml, from about 1 µg/ml to about 7 µg/ml, from about 2 µg/ml to about 7 µg/ml, from about 3 µg/ml to about 7 µg/ml, from about 4 µg/ml to about 7 µg/ml, from about 5 µg/ml to about 7 µg/ml, from about 6 µg/ml to about 7 µg/ml, from about 1 µg/ml to about 6 µg/ml, from about 2 µg/ml to about 6 µg/ml, from about 3 µg/ml to about 6 µg/ml, from about 4 µg/ml to about 6 µg/ml, from about 5 µg/ml to about 6 µg/ml, from about 1 µg/ml to about 5 µg/ml, from about 2 µg/ml to about 5 µg/ml, from about 3 µg/ml to about 5 µg/ml, from about 4 µg/ml to about 5 µg/ml, from about 1 µg/ml to about 4 µg/ml, from about 2 µg/ml to about 4 µg/ml, from about 3 µg/ml to about 4 µg/ml, from about 1 µg/ml to about 3 µg/ml, from about 2 µg/ml to about 3 µg/ml, or from about 1 µg/ml to about 2 µg/ml). In other embodiments, the inhibitor of MOSPD2 is an antibody or antigen binding fragment of an antibody, and the therapeutically effective amount is about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, or about 10 µg/ml.

In some embodiments, the inhibitor of MOSPD2 is an antibody or antigen binding fragment of an antibody, and the therapeutically effective amount is from about 10 mg/kg to about 40 mg/kg, or any range of values thereof (e.g., from about 15 mg/kg to about 40 mg/kg, from about 20 mg/kg to about 40 mg/kg, from about 25 mg/kg to about 40 mg/kg, from about 30 mg/kg to about 40 mg/kg, from about 35 mg/kg to about 40 mg/kg, from about 10 mg/kg to about 35 mg/kg, from about 15 mg/kg to about 35 mg/kg, from about 20 mg/kg to about 35 mg/kg, from about 25 mg/kg to about 35 mg/kg, from about 30 mg/kg to about 35 mg/kg, from about 10 mg/kg to about 30 mg/kg, from about 15 mg/kg to about 30 mg/kg, from about 20 mg/kg to about 30 mg/kg, from about 25 mg/kg to about 30 mg/kg, from about 10 mg/kg to about 25 mg/kg, from about 15 mg/kg to about 25 mg/kg, from about 20 mg/kg to about 25 mg/kg, from about 10 mg/kg to about 20 mg/kg, from about 15 mg/kg to about 20 mg/kg, or from about 10 mg/kg to about 15 mg/kg). In other embodiments, the inhibitor of MOSPD2 is an antibody or antigen binding fragment of an antibody, and the therapeutically effective amount is about 10 mg/kg, about 15 mg/kg, about 20 mg/kg, about 25 mg/kg, about 30 mg/kg, about 35 mg/kg, or about 40 mg/kg.

In some embodiments, the subject is a mammal or a human. In other embodiments the MOSPD2 is a mammalian MOSPD2 or a human MOSPD2.

Methods of Inhibiting or Preventing One or More Activities in or of a Cancer Cell Embodiments of the invention also relate to methods of inhibiting or preventing one or more activities in or of a cancer cell comprising administering an inhibitor of MOSPD2. In some embodiments, the methods comprise administering a therapeutically effective amount of an inhibitor of MOSPD2 to a subject in need thereof. In some embodiments, the administration is local administration, e.g., intra-tumor administration. Exemplary MOSPD2 inhibitors include those described herein. Suitable types of cancer are also described herein.

In some embodiments, the inhibitor of MOSPD2 is an antibody or antigen binding fragment of an antibody described herein, e.g., having an antibody-antigen equilibrium dissociation constant ($K_D$) of from about $10^{-6}$ M to about $10^{-12}$ M, or any range of values thereof (e.g., from about $10^{-7}$ M to about $10^{-12}$, from $10^{-8}$ M to about $10^{-12}$ M, from about $10^{-9}$ M to about $10^{-12}$ M, from about $10^{-10}$ M to about $10^{-12}$ M, from about $10^{-11}$ M to about $10^{-12}$ M, from about $10^{-6}$ M to about $10^{-11}$ M, from about $10^{-7}$ M to about $10^{-11}$ M, from about $10^{-8}$ M to about $10^{-11}$ M, from about $10^{-9}$ M to about $10^{-11}$ M, from about $10^{-10}$ M to about $10^{-11}$ M, from about $10^{-6}$ M to about $10^{-10}$ M, from about $10^{-7}$ M to about $10^{-10}$ M, from about $10^{-8}$ M to about $10^{-10}$ M, from about $10^{-9}$ M to about $10^{-10}$ M, from about $10^{-6}$ M to about $10^{-9}$ M, from about $10^{-7}$ M to about $10^{-9}$ M, from about $10^{-8}$ M to about $10^{-9}$ M, from about $10^{-6}$ M to about $10^{-8}$ M, or from about $10^{-7}$ M to about $10^{-8}$). In other embodiments, the antibody or antigen binding fragment thereof has a $K_D$ of about $10^{-6}$ M, about $10^{-7}$ M, about $10^{-8}$ M, about $10^{-9}$ M, about $10^{-10}$ M, about $10^{-11}$ M, or about $10^{-12}$ M. In some embodiments, the antibody or antigen binding fragment binds to one or more epitopes on MOSPD2. In some embodiments, the $K_D$ is determined by Scatchard analysis, surface plasmon resonance, or other method described herein, in some embodiments, at 37° C.

In some embodiments, antibodies or antigen binding fragments of the invention bind to MOSPD2 with a $K_{on}$ of from about $10^3$ 1/Ms to about $10^6$ 1/Ms, or any range of values thereof (e.g., from about $10^3$ 1/Ms to about $10^5$ 1/Ms, from about $10^4$ 1/Ms to about $10^5$ 1/Ms, from about $10^4$ 1/Ms to about $10^6$ 1/Ms, from about $10^5$ 1/Ms to about $10^6$ 1/Ms, or from about $10^3$ 1/Ms to about $10^4$ 1/Ms). In other embodiments, the antibody or antigen binding fragment has a $K_{on}$ of about $10^3$ 1/Ms, about $10^4$ 1/Ms, about $10^5$ 1/Ms, or about $10^6$ 1/Ms.

In some embodiments, antibodies or antigen binding fragments of the invention bind to MOSPD2 with a $K_{off}$ of from about $10^{-3}$ 1/s to about $10^{-6}$ 1/s, or any range of values thereof (e.g., from about $10^{-3}$ 1/s to about $10^{-5}$ 1/s, from about $10^{-4}$ 1/s to about $10^{-5}$ 1/s, from about $10^{-4}$ 1/s to about $10^{-6}$ 1/s, from about $10^{-5}$ 1/s to about $10^{-6}$ 1/s, or from about $10^{-3}$ 1/s to about $10^{-4}$ 1/s). In other embodiments, the antibody or antigen binding fragment has a $K_{off}$ of about $10^{-3}$ 1/s, about $10^{-4}$ 1/s, about $10^{-5}$ 1/s, or about $10^{-6}$ 1/s.

In some embodiments, the inhibitor of MOSPD2 is an antibody or antigen binding fragment of an antibody, and the therapeutically effective amount is from about 1 µg/ml to about 10 µg/ml, or any range of values thereof (e.g., from about 2 µg/ml to about 10 µg/ml, from about 3 µg/ml to about 10 µg/ml, from about 4 µg/ml to about 10 µg/ml, from about 5 µg/ml to about 10 µg/ml, from about 6 µg/ml to about 10 µg/ml, from about 7 µg/ml to about 10 µg/ml, from about 8 µg/ml to about 10 µg/ml, from about 9 µg/ml to about 10 µg/ml, from about 1 µg/ml to about 9 µg/ml, from about 2 µg/ml to about 9 µg/ml, from about 3 µg/ml to about 9 µg/ml, from about 4 µg/ml to about 9 µg/ml, from about 5 µg/ml to about 9 µg/ml, from about 6 µg/ml to about 9 µg/ml, from about 7 µg/ml to about 9 µg/ml, from about 8 µg/ml to about 9 µg/ml, from about 1 µg/ml to about 8 µg/ml, from about 2 µg/ml to about 8 µg/ml, from about 3 µg/ml to about 8 µg/ml, from about 4 µg/ml to about 8 µg/ml, from about 5 µg/ml to about 8 µg/ml, from about 6 µg/ml to about 8 µg/ml, from about 7 µg/ml to about 8 µg/ml, from about 1 µg/ml to about 7 µg/ml, from about 2 µg/ml to about 7 µg/ml, from about 3 µg/ml to about 7 µg/ml, from about 4 µg/ml to about 7 µg/ml, from about 5 µg/ml to about 7 µg/ml, from about 6 µg/ml to about 7 µg/ml, from about 1 µg/ml to about 6 µg/ml, from about 2 µg/ml to about 6 µg/ml, from about 3 µg/ml to about 6 µg/ml, from about 4 µg/ml to about 6 µg/ml, from about 5 µg/ml to about 6 µg/ml, from about 1 µg/ml to about 5 µg/ml, from about 2 µg/ml to about 5 µg/ml, from about 3 µg/ml to about 5 µg/ml, from about 4 µg/ml to about 5 µg/ml, from about 1 µg/ml to about 4 µg/ml, from about 2 µg/ml to about 4 µg/ml, from about 3 µg/ml to about 4 µg/ml, from about 1 µg/ml to about 3 µg/ml, from about 2 µg/ml to about 3 µg/ml, or from about 1 µg/ml to about 2 µg/ml). In other embodiments, the inhibitor of MOSPD2 is an antibody or antigen binding fragment of an antibody, and the therapeutically effective amount is about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, or about 10 µg/ml.

In some embodiments, the inhibitor of MOSPD2 is an antibody or antigen binding fragment of an antibody, and the therapeutically effective amount is from about 10 mg/kg to about 40 mg/kg, or any range of values thereof (e.g., from about 15 mg/kg to about 40 mg/kg, from about 20 mg/kg to about 40 mg/kg, from about 25 mg/kg to about 40 mg/kg, from about 30 mg/kg to about 40 mg/kg, from about 35 mg/kg to about 40 mg/kg, from about 10 mg/kg to about 35 mg/kg, from about 15 mg/kg to about 35 mg/kg, from about 20 mg/kg to about 35 mg/kg, from about 25 mg/kg to about 35 mg/kg, from about 30 mg/kg to about 35 mg/kg, from about 10 mg/kg to about 30 mg/kg, from about 15 mg/kg to about 30 mg/kg, from about 20 mg/kg to about 30 mg/kg, from about 25 mg/kg to about 30 mg/kg, from about 10 mg/kg to about 25 mg/kg, from about 15 mg/kg to about 25 mg/kg, from about 20 mg/kg to about 25 mg/kg, from about 10 mg/kg to about 20 mg/kg, from about 15 mg/kg to about 20 mg/kg, or from about 10 mg/kg to about 15 mg/kg). In other embodiments, the inhibitor of MOSPD2 is an antibody or antigen binding fragment of an antibody, and the therapeutically effective amount is about 10 mg/kg, about 15 mg/kg, about 20 mg/kg, about 25 mg/kg, about 30 mg/kg, about 35 mg/kg, or about 40 mg/kg.

In some embodiments, the inhibitor of MOSPD2 (e.g., an antibody or antigen binding fragment thereof) causes at least about 10% (e.g., at least about 20%, at least about 30%, at least about 40%, at least about 40%, at least about 50%, at least about 60%, at least about 70%, at least about 80%, at least about 90%, at least about 95%, at least about 99%, or higher) inhibition of one or more activities of MOSPD2 (e.g., human MOSPD2) (e.g., MOSPD2 expression, cancer cell migration, monocyte migration associated with tumor growth (e.g., presence of tumor associated macrophages), a chemokine signaling pathway, a growth factor signaling pathway, EGF receptor phosphorylation, ERK phosphorylation, AKT phosphorylation, and/or FAK phosphorylation). In other embodiments, administration of the MOSPD2 inhibitor (e.g., an antibody or antigen binding fragment thereof) causes from about 10% to 100%, from about 10% to about 99%, from about 10% to about 95%, from about 10% to about 90%, from about 10% to about 85%, from about 10% to about 80%, from about 10% to about 70%, from about 20% to about 99%, from about 20% to about 95%, from about 20% to about 90%, from about 20% to about 85%, from about 20% to about 80%, from about 30% to about 95%, from about 30% to about 90%, from about 30% to about 85%, from about 30% to about 80%, from about 40% to about 95%, from about 40% to about 90%, from about 40% to about 85%, from about 40% to about 80%, from about 50% to about 95%, from about 50% to about 90%, from about 50% to about 85%, from about 50% to about 80%, from about 60% to about 95%, from about 60% to about 90%, from about 60% to about 85%, or from about 60% to about 80% inhibition of one or more activities of MOSPD2 (e.g., human MOSPD2) (e.g., MOSPD2 expression, cancer cell migration, monocyte migration associated with tumor growth (e.g., presence of tumor associated macrophages), a chemokine signaling pathway, a growth factor signaling pathway, EGF receptor phosphorylation, ERK phosphorylation, AKT phosphorylation, and/or FAK phosphorylation). In one aspect, administration of an anti-MOSPD2 antibody or antigen binding fragment thereof causes from about 10% to 100%, from about 10% to about 99%, from about 10% to about 95%, from about 10% to about 90%, from about 10% to about 85%, from about 10% to about 80%, from about 10% to about 70%, from about 20% to about 99%, from about 20% to about 95%, from about 20% to about 90%, from about 20% to about 85%, from about 20% to about 80%, from about 30% to about 95%, from about 30% to about 90%, from about 30% to about 85%, from about 30% to about 80%, from about 40% to about 95%, from about 40% to about 90%, from about 40% to about 85%, from about 40% to about 80%, from about 50% to about 95%, from about 50% to about 90%, from about 50% to about 85%, from about 50% to about 80%, from about 60% to about 95%, from about 60% to about 90%, from about 60% to about 85%, or from about 60% to about 80% inhibition of cancer cell migration (e.g., EGF-induced migration).

In some embodiments, the one or more activities is one or more of: MOSPD2 expression, cancer cell migration, monocyte migration associated with tumor growth (e.g., presence of tumor associated macrophages), a chemokine signaling pathway, a growth factor signaling pathway, EGF receptor phosphorylation, ERK phosphorylation, AKT phosphorylation, and/or FAK phosphorylation. In some embodiments, at least two, at least three, at least four, at least five, at least six, at least seven, at least eight, at least nine, at least ten, or all of these activities are inhibited.

In some embodiments, at least cancer cell migration and a chemokine signaling pathway are inhibited. In other embodiments, the inhibiting of a chemokine signaling pathway or a growth factor signaling pathway is the inhibiting of EGF receptor phosphorylation, ERK phosphorylation, AKT phosphorylation, and/or FAK phosphorylation. In other embodiments, the cancer cell migration or monocyte migration associated with tumor growth (e.g., presence of tumor associated macrophages) is induced by more than one chemokine or growth factor (e.g., EGF) or chemokine receptor or growth factor receptor (e.g., EGFR).

In some embodiments, the subject is a mammal or a human. In other embodiments the MOSPD2 is a mammalian MOSPD2 or a human MOSPD2.

Methods of Reducing Tumor Associated Macrophages or Tumor Associated Macrophage Migration Tumor associated macrophages (TAMs) are often found in close proximity or within tumor masses. TAMs are known to be important for tumor growth. TAMs mostly originate from circulating monocytes and their recruitment into tumors is driven by tumor-derived chemotactic factors. TAMs promote tumor cell proliferation and metastasis by secreting a wide range of growth and proangiogenic factors. Consequently, many tumors with a high number of TAMs have an increased tumor growth rate, local proliferation and distant metastasis. In fact, the extent of TAM infiltration has been used as an inverse prognostic predictor in breast cancer, head and neck cancer, prostate and uterine cancer (R. D. Leek, R. Landers, S. B. Fox, F. Ng, A. L. Harris, C. E. Lewis, *British journal of cancer* 1998, 77, 2246; M. R. Young, M. A. Wright, Y. Lozano, M. M. Prechel, J. Benefield, J. P. Leonetti, S. L. Collins, G. J. Petruzzelli, *International Journal of Cancer* 1997, 74, 69; I. F. Lissbrant, P. Stattin, P. Wikstrom, J. E. Damber, L. Egevad, A. Bergh, *International journal of oncology* 2000, 17, 445; H. B. Salvesen, L. A. Akslen, *International Journal of Cancer* 1999, 84, 538). TAMs are also prominent in tumor tissues, comprising up to 80% of the cell mass in breast carcinoma.

Some embodiments of the invention relate to methods for treating, reducing the incidence of, or preventing a cancer, which include administering to a subject in need thereof an effective amount of an inhibitor of MOSPD2, e.g., MOSPD2 expressed by circulating monocytes or tumor associated macrophages, to reduce the number of tumor associated macrophages near or within the cancer mass or reduce migration of tumor associated macrophages. Some embodiments of the invention relate to methods for treating, preventing, or reducing the incidence of cancer metastasis, which include administering to a subject in need thereof an effective amount of an inhibitor of MOSPD2, e.g., MOSPD2 expressed by circulating monocytes or tumor associated macrophages, to reduce the number of tumor associated macrophages near or within the cancer mass or reduce migration of tumor associated macrophages. In some embodiments, the administration is local administration, e.g., intra-tumor administration. In some embodiments, the administration is effective in reducing the number or migration of tumor associated macrophages by at least about 5%, at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or 100%, or any number in between the aforementioned percentages, when compared to baseline.

In some embodiments, the administration is effective in reducing the number or migration of tumor associated macrophages by about 5%, about 10%, about 20%, about 25%, about 30%, about 35%, about 40%, about 45%, about 50%, about 55%, about 60%, about 65%, about 70%, about 75%, about 80%, about 85%, about 90%, about 95%, or 100%, or any number in between the aforementioned percentages, when compared to baseline.

In other embodiments, the administration is effective in reducing the number or migration of tumor associated macrophages, when compared to baseline, by from about 5% to 100%, or from about 5% to about 95%, from about 5% to about 90%, from about 5% to about 80%, from about 5% to about 70%, from about 5% to about 60%, from about 5% to about 50%, from about 5% to about 40%, from about 5% to about 30%, from about 10% to 100%, from about 10% to about 95%, from about 10% to about 90%, from about 10% to about 80%, from about 10% to about 70%, from about 10% to about 60%, from about 10% to about 50%, from about 10% to about 40%, from about 20% to 100%, from about 20% to about 95%, from about 20% to about 90%, from about 20% to about 80%, from about 20% to about 70%, from about 20% to about 60%, from about 20% to about 50%, from about 20% to about 40%, or any other range of values described herein.

Any assay known in the art can be used to measure tumor associated macrophage density or numbers such as immunohistochemical staining of tumor sections using antibodies that specifically detect macrophages. See e.g., U.S. Patent Publication Nos. 2007/0218116 and 2011/0311616. Exemplary MOSPD2 inhibitors include those described herein. Suitable types of cancer are also described herein. In some embodiments, the cancer is a breast cancer, a head and neck cancer, a prostate cancer or a uterine cancer.

In some embodiments, the inhibitor of MOSPD2 is an antibody or antigen binding fragment of an antibody described herein, e.g., having an antibody-antigen equilibrium dissociation constant ($K_D$) of from about $10^{-6}$ M to about $10^{-12}$ M, or any range of values thereof (e.g., from about $10^{-6}$ M to about $10^{-12}$, from $10^{-8}$ M to about $10^{-12}$ M, from about $10^{-9}$ M to about $10^{-12}$ M, from about $10^{-10}$ M to about $10^{-12}$ M, from about $10^{-11}$ M to about $10^{-12}$ M, from about $10^{-6}$ M to about $10^{-11}$ M, from about $10^{-6}$ M to about $10^{-11}$ M, from about $10^{-8}$ M to about $10^{-11}$ M, from about $10^{-6}$ M to about $10^{-11}$ M, from about $10^{-10}$ M to about $10^{-11}$ M, from about $10^{-6}$ M to about $10^{-10}$ M, from about $10^{-6}$ M to about $10^{-10}$ M, from about $10^{-8}$ M to about $10^{-10}$ M, from about $10^{-9}$ M to about $10^{-10}$ M, from about $10^{-6}$ M to about $10^{-9}$ M, from about $10^{-7}$ M to about $10^{-9}$ M, from about $10^{-8}$ M to about $10^{-9}$ M, from about $10^{-6}$ M to about $10^{-8}$ M, or from about $10^{-7}$ M to about $10^{-8}$). In other embodiments, the antibody or antigen binding fragment thereof has a $K_D$ of about $10^{-6}$ M, about $10^{-7}$ M, about $10^{-8}$ M, about $10^{-9}$ M, about $10^{-10}$ M, about $10^{-11}$ M, or about $10^{-12}$ M. In some embodiments, the antibody or antigen binding fragment binds to one or more epitopes on MOSPD2. In some embodiments, the $K_D$ is determined by Scatchard analysis, surface plasmon resonance, or other method described herein, in some embodiments, at 37° C.

In some embodiments, antibodies or antigen binding fragments of the invention bind to MOSPD2 with a $K_{on}$ of from about $10^3$ 1/Ms to about $10^6$ 1/Ms, or any range of values thereof (e.g., from about $10^3$ 1/Ms to about $10^5$ 1/Ms, from about $10^4$ 1/Ms to about $10^5$ 1/Ms, from about $10^4$ 1/Ms to about $10^6$ 1/Ms, from about $10^5$ 1/Ms to about $10^6$ 1/Ms, or from about $10^3$ 1/Ms to about $10^4$ 1/Ms). In other embodiments, the antibody or antigen binding fragment has a $K_{on}$ of about $10^3$ 1/Ms, about $10^4$ 1/Ms, about $10^5$ 1/Ms, or about $10^6$ 1/Ms.

In some embodiments, antibodies or antigen binding fragments of the invention bind to MOSPD2 with a $K_{off}$ of from about $10^{-3}$ 1/s to about $10^{-6}$ 1/s, or any range of values thereof (e.g., from about $10^{-3}$ 1/s to about $10^{-5}$ 1/s, from about $10^{-4}$ 1/s to about $10^{-5}$ 1/s, from about $10^{-4}$ 1/s to about $10^{-6}$ 1/s, from about $10^{-5}$ 1/s to about $10^{-6}$ 1/s, or from about $10^{-6}$ 1/s to about $10^{-4}$ 1/s). In other embodiments, the antibody or antigen binding fragment has a $K_{off}$ of about $10^{-3}$ 1/s, about $10^{-4}$ 1/s, about $10^{-5}$ 1/s, or about $10^{-6}$ 1/s.

In some embodiments, the inhibitor of MOSPD2 is an antibody or antigen binding fragment of an antibody, and the therapeutically effective amount is from about 1 µg/ml to about 10 µg/ml, or any range of values thereof (e.g., from about 2 µg/ml to about 10 µg/ml, from about 3 µg/ml to about 10 µg/ml, from about 4 µg/ml to about 10 µg/ml, from about 5 µg/ml to about 10 µg/ml, from about 6 µg/ml to about 10 µg/ml, from about 7 µg/ml to about 10 µg/ml, from about 8 µg/ml to about 10 µg/ml, from about 9 µg/ml to about 10 µg/ml, from about 1 µg/ml to about 9 µg/ml, from about 2 µg/ml to about 9 µg/ml, from about 3 µg/ml to about 9 µg/ml, from about 4 µg/ml to about 9 µg/ml, from about 5 µg/ml to about 9 µg/ml, from about 6 µg/ml to about 9 µg/ml, from about 7 µg/ml to about 9 µg/ml, from about 8 µg/ml to about 9 µg/ml, from about 1 µg/ml to about 8 µg/ml, from about 2 µg/ml to about 8 µg/ml, from about 3 µg/ml to about 8 µg/ml, from about 4 µg/ml to about 8 µg/ml, from about 5 µg/ml to about 8 µg/ml, from about 6 µg/ml to about 8 µg/ml, from about 7 µg/ml to about 8 µg/ml, from about 1 µg/ml to about 7 µg/ml, from about 2 µg/ml to about 7 µg/ml, from about 3 µg/ml to about 7 µg/ml, from about 4 µg/ml to about 7 µg/ml, from about 5 µg/ml to about 7 µg/ml, from about 6 µg/ml to about 7 µg/ml, from about 1 µg/ml to about 6 µg/ml, from about 2 µg/ml to about 6 µg/ml, from about 3 µg/ml to about 6 µg/ml, from about 4 µg/ml to about 6 µg/ml, from about 5 µg/ml to about 6 µg/ml, from about 1 µg/ml to about 5 µg/ml, from about 2 µg/ml to about 5 µg/ml, from about 3 µg/ml to about 5 µg/ml, from about 4 µg/ml to about 5 µg/ml, from about 1 µg/ml to about 4 µg/ml, from about 2 µg/ml to about 4 µg/ml, from about 3 µg/ml to about 4 µg/ml, from about 1 µg/ml to about 3 µg/ml, from about 2 µg/ml to about 3 µg/ml, or from about 1 µg/ml to about 2 µg/ml). In other embodiments, the inhibitor of MOSPD2 is an antibody or antigen binding fragment of an antibody, and the therapeutically effective amount is about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, or about 10 µg/ml.

In some embodiments, the inhibitor of MOSPD2 is an antibody or antigen binding fragment of an antibody, and the therapeutically effective amount is from about 10 mg/kg to about 40 mg/kg, or any range of values thereof (e.g., from about 15 mg/kg to about 40 mg/kg, from about 20 mg/kg to about 40 mg/kg, from about 25 mg/kg to about 40 mg/kg, from about 30 mg/kg to about 40 mg/kg, from about 35 mg/kg to about 40 mg/kg, from about 10 mg/kg to about 35 mg/kg, from about 15 mg/kg to about 35 mg/kg, from about 20 mg/kg to about 35 mg/kg, from about 25 mg/kg to about 35 mg/kg, from about 30 mg/kg to about 35 mg/kg, from about 10 mg/kg to about 30 mg/kg, from about 15 mg/kg to about 30 mg/kg, from about 20 mg/kg to about 30 mg/kg, from about 25 mg/kg to about 30 mg/kg, from about 10 mg/kg to about 25 mg/kg, from about 15 mg/kg to about 25 mg/kg, from about 20 mg/kg to about 25 mg/kg, from about 10 mg/kg to about 20 mg/kg, from about 15 mg/kg to about 20 mg/kg, or from about 10 mg/kg to about 15 mg/kg). In other embodiments, the inhibitor of MOSPD2 is an antibody or antigen binding fragment of an antibody, and the therapeutically effective amount is about 10 mg/kg, about 15 mg/kg, about 20 mg/kg, about 25 mg/kg, about 30 mg/kg, about 35 mg/kg, or about 40 mg/kg.

In some embodiments, the subject is a mammal or a human. In other embodiments the MOSPD2 is a mammalian MOSPD2 or a human MOSPD2.

Diagnostic Methods

The inventors have discovered that MOSPD2 is expressed on the surface of different types of cancer cells and tumors, and on inflammatory cells that have infiltrated into inflamed tissues or that are associated with tumors. The inventors have also discovered that MOSPD2 expression is increased in correlation with tumor grade in various types of tumors. Therefore, in one aspect, the invention relates to a method for the prediction, diagnosis, or prognosis of cancer or cancer metastasis in a subject (e.g., breast cancer, colon cancer, liver cancer, melanoma, or other type of cancer described herein), which comprises determining the expression level of MOSPD2 in a sample of the subject. In another aspect, the invention relates to a method for the prediction, diagnosis, or prognosis of tumor progression or invasiveness in a subject, which comprises determining the expression level of MOSPD2 in a sample of the subject. In one embodiment of these methods, the expression level of MOSPD2 is the level of MOSPD2 gene expression. In another embodiment, the expression level of MOSPD2 is the level of MOSPD2 protein expression.

In one aspect, the invention relates to an in vitro method for the prediction, diagnosis or prognosis of cancer in a subject (e.g., breast cancer, colon cancer, liver cancer, melanoma, or other type of cancer described herein), which comprises determining or quantifying the expression level of MOSPD2 in a sample of the subject. In another aspect, the invention relates to an in vitro method for the prediction, diagnosis or prognosis of cancer in a subject (e.g., breast cancer, colon cancer, liver cancer, melanoma, or other type of cancer described herein), which comprises (i) determining or quantifying the expression level of MOSPD2 in a sample of the subject, and (ii) comparing the expression level obtained in step (i) with a control or reference value, wherein an increased expression level of MOSPD2 with respect to the control or reference value is indicative of cancer or an increased risk of developing cancer. In some embodiments, if MOSPD2 expression is present in the sample of the subject, then the subject has cancer or an increased risk of cancer. In other embodiments, if MOSPD2 expression is present in the sample of the subject in an amount greater than MOSPD2 expression of the control or reference value, then the subject has cancer or an increased risk of cancer.

In one aspect, the invention relates to an in vitro method for the prediction, diagnosis or prognosis of cancer metastasis in a subject (e.g., breast cancer, colon cancer, liver cancer, melanoma, or other type of cancer described herein), which comprises determining or quantifying the expression level of MOSPD2 in a sample of the subject. In another aspect, the invention relates to an in vitro method for the prediction, diagnosis or prognosis of cancer metastasis in a subject (e.g., breast cancer, colon cancer, liver cancer, melanoma, or other type of cancer described herein), which comprises (i) determining or quantifying the expression level of MOSPD2 in a sample of the subject, and (ii) comparing the expression level obtained in step (i) with a control or reference value, wherein an increased expression level of MOSPD2 with respect to the control or reference value is indicative of cancer metastasis or an increased risk of cancer metastasis. In some embodiments, if MOSPD2 expression is present in the sample of the subject, then the subject has cancer metastasis or an increased risk of cancer metastasis. In other embodiments, if MOSPD2 expression is present in the sample of the subject in an amount greater than MOSPD2 expression of the control or reference value, then the subject has cancer metastasis or an increased risk of cancer metastasis.

In one aspect, the invention relates to an in vitro method for the prediction, diagnosis or prognosis of tumor progression (e.g., increased tumor grade) or invasiveness in a subject, which comprises determining or quantifying the expression level of MOSPD2 in a sample of the subject. In another aspect, the invention relates to an in vitro method for the prediction, diagnosis or prognosis of tumor progression (e.g., increased tumor grade) or invasiveness in a subject, which comprises (i) determining or quantifying the expression level of MOSPD2 in a sample of the subject, and (ii) comparing the expression level obtained in step (i) with a control or reference value, wherein increased expression level of MOSPD2 with respect to the control or reference value is indicative of tumor progression (e.g., increased tumor grade) or invasiveness or an increased risk of tumor progression or invasiveness. In some embodiments, if MOSPD2 expression is present in the sample of the subject, then the subject has tumor progression or invasiveness or an increased risk of tumor progression or invasiveness. In other embodiments, if MOSPD2 expression is present in the sample of the subject in an amount greater than MOSPD2 expression of the control or reference value, then the subject has tumor progression or tumor invasiveness or an increased risk of tumor progression or invasiveness.

In some embodiments, the methods of the invention comprise one or more of the following additional steps: instructing a laboratory to quantify the expression level of MOSPD2 in the sample; obtaining a report of the expression level of MOSPD2 in the sample from the laboratory; and/or administering a therapeutically effective amount of an inhibitor of MOSPD2 (e.g., an anti-MOSPD2 antibody or antigen binding fragment thereof) to the subject.

In some embodiments, the sample is a tissue biopsy, tumor biopsy, or blood sample from a subject.

In some embodiments, the control or reference value is the expression level of MOSPD2 in normal tissue (e.g., normal adjacent tissue (NAT)). In other embodiments, the control or reference value is no detectable MOSDP2 expression or no significant MOSPD2 expression.

Methods for determining the expression level of MOSPD2 are known in the literature and described herein.

In some embodiments, the invention relates to a method for treating a cancer or cancer metastasis responsive to an inhibitor of MOSPD2 in a subject, comprising (i) determining the expression level of MOSPD2 in the subject, and when the expression level is determined to be greater than that of a control or reference value, (ii) administering, to the subject, a therapeutically effective amount of an inhibitor of MOSPD2 (e.g., an anti-MOSPD2 antibody or antigen binding fragment thereof).

In some embodiments, the invention relates to a method for treating a MOSPD2 expressing tumor in a subject, which comprises administering a therapeutically effective amount of an inhibitor of MOSPD2 (e.g., an anti-MOSPD2 antibody or antigen binding fragment thereof). In other embodiments, the invention relates to a method of treating a subject, which comprises administering a therapeutically effective amount of an inhibitor of MOSPD2 (e.g., an anti-MOSPD2 antibody or antigen binding fragment thereof), wherein the subject has a tumor expressing MOSPD2.

In some embodiments, the invention relates to an inhibitor of MOSPD2 (e.g., an anti-MOSPD2 antibody or antigen binding fragment thereof), for use in treating cancer or cancer metastasis in a patient having a cancer cell or tumor that expresses MOSPD2.

EXAMPLES

Reference is now made to the following examples, which together with the above descriptions illustrate some embodiments of the invention in a non-limiting fashion.

Materials and Methods

MOSPD2 Silencing

The human breast cancer cell line MDA-MB-231 (hereafter MDA-231) (HTB-26) and the human malignant melanoma cell line A2058 (CRL-11147) were purchased from the American Type Culture Collection (ATCC). The cells ($2\times10^6$ in 2 ml) were placed in a 15 ml tube. Lenti-virus particles expressing control short hairpin RNA (sh-RNA) ($2\times10^5$ viral particles) or human MOSPD2 sh-RNA ($2\times10^6$ viral particles) were applied to the cells, which were then spun for 60 min, 2000 rpm at room temperature in the presence of 8 µg/ml polybrene (Sigma, Israel). The cells were then seeded in a 6 well plate. After 72 hour, fresh medium containing puromycin (4 µg/ml Sigma, Israel) was added for the selection of transduced cells. For CRISPR-CAS9 mediated silencing, MDA-231 cells were transduced with CRISPR-CAS9 non-target control or CRISPR-CAS9 human MOSPD2 lenti-viral particles as described above. Single cell cloning was performed on transduced cells to isolate cells with silenced MOSPD2 protein expression and impaired migration.

Western Blotting sh-control or sh-MOSPD2 Lenti-virus transduced A2058 or MDA-231 cells, or control or MOSPD2 CRISPR-CAS9 lenti-viral particles transduced MDA-231 cells ($10^6$), were washed and resuspended in lysis buffer containing 1:100 dithiothreitol (DTT), phosphatase and protease inhibitors (Thermo Scientific). Samples were loaded onto a precast Criterion TGX gel (Bio-Rad, Hemel Hempstead, UK) and transferred onto a nitrocellulose membrane. Blots were blocked with 5% milk or bovine serum albumin (BSA) in Tris buffered saline and Tween 20 (TBST) for 1 hour, followed by incubation with primary and secondary antibodies. Membranes were developed using an ECL kit (Thermo Scientific). The following antibodies were used for immunoblotting:

Primary antibodies: Rabbit anti-MOSPD2 (1:5000) generated by Vascular Biogenics Ltd. Phospho extracellular-regulated kinase (p-ERK1/2) (Thr 183 and Tyr 185, 1:4000) was purchased from Sigma (Israel). Phospho-AKT (Ser 473, 1:1000) was purchased from Cell Signaling. Phospho-FAK (1:2000) was purchased from Abcam (Cambridge, UK). Heat shock protein (HSP) 90 (1:1000) was purchased from Santa Cruz biotechnology (Dallas, TX).

Secondary antibodies: Horseradish peroxidase (HRP) donkey anti-rabbit (1:5000) and HRP goat anti-mouse (1:5000) antibodies were purchased from Jackson ImmunoResearch (West Grove, PA).

Q-PCR

To determine silencing efficacy, RNA was extracted from sh-control and sh-MOSPD2 Lenti-virus transduced MDA-231 cells using RNeasy mini kit (Qiagen, ValenVBa, CA). For cDNA preparation, 2 µg of RNA was combined with qScript reaction mix and qScript reverse transcriptase (Quanta Bioscience, Gaithersburg, MD). The reaction was placed in a thermal cycler (BioRad, Hercules, CA) and a run program was set according to the manufacturer instructions. Real-time PCR reactions were performed on an Applied Biosystems 7300 real time PCR system (Grand Island, NY) using sets of primers for human MOSPD2, 28S to normalize RNA levels (BIOSEARCH TECHNOLOGIES, Petaluma, CA) and SYBR Green PCR Master Mix (Applied Biosystems, Warrington, UK).

Immunohistochemistry Staining

To assess the expression level of MOSPD2 in cancer tissues, Biomax arrays (US Biomax Rockville, MD) for breast cancer (T088B and BR2028a), for liver cancer (BC03116a), and for multiple organ tumor (MC6163) were stained with the rabbit anti-MOSPD2 antibody or control rabbit IgG (R&D Systems Cat #AB-105-C) followed by incubation with anti-Rabbit HRP (Cat #0399 DAKO, Denmark).

Example 1

Anti-MOSPD2 Antibodies

Anti-MOSPD2 polyclonal antibodies were generated according to the following methods.

Materials and Methods

Production and Purification of Hemagglutinin MA)-Tagged Recombinant Human Mospd2 (HA-rhMOSPD2)

Full length human MOSPD2 cDNA was inserted, using EcoRI and XbaI restriction sites, into the lentivirus plasmid vector pLVX-EF1α-IRES-Puro (Clonetech, CA). Oligonucleotide encoding the HA-tag (YPYDVPDYA; SEQ ID NO:15) was inserted into the N-terminal region of MOSPD2 with EcoRI restriction sites. For transduction, A2058 melanoma cells (ATCC CRL-11147, VA) were spun for 60 minutes at 2000 rpm at room temperature in the presence of 8 µg/ml polybrene (Sigma, Israel) and lentiviral particles containing HA-rhMOSPD2 expressing vector. The cells were then seeded in a 6 well plate. After 72 hours, fresh medium containing puromycin (4 µg/ml Sigma, Israel) was added for the selection of transduced cells. To purify HA-rhMOSPD2, A2058 transduced cells were lysed with M-PER mammalian protein extraction reagent (Thermo Scientific) and passed through anti-HA agarose beads (Thermo Scientific). Glycine or sodium thiocyanate was used for the elution of HA-rhMOSPD2 from the beads, followed by thorough dialysis against PBS.

Generation and Isolation of α-MOSPD2 Polyclonal Antibodies

Rabbits were immunized with approximately 0.5 mg of HA-rhMOSPD2 emulsified in complete freunds adjuvant followed by three boosts every three weeks with approximately 0.25 mg of HA-rhMOSPD2 emulsified in incomplete freunds adjuvant. Serum was collected one week after each boost to assess for antibody immunogenicity and titers. α-MOSPD2 antibodies were isolated from serum using protein A/G beads (SantaCruz, CA).

Results

Rabbit Polyclonal α-MOSPD2 Antibodies Detect and Precipitate Endogenous Human MOSPD2

Isolated α-MOSPD2 polyclonal antibodies were evaluated for their ability to detect and precipitate endogenous MOSPD2. Cell lysate was prepared from U937 cells transduced with control or sh-MOSPD2 Lenti-virus particles. Samples were analyzed by Western blot using the isolated α-MOSPD2 antibodies (diluted 1:5000). Expression of HSP90 was also determined as a loading control. Immunoprecipitation of U397 cell lysate was also performed using the isolated α-MOSPD2 antibodies or rabbit IgG (10 µg) as a control. The resulting precipitates were analyzed by immunoblot with the isolated α-MOSPD2 antibodies, followed by incubation with goat anti-rabbit antibody-HRP (1:5000). Results show that the isolated α-MOSPD2 antibodies readily detect and immunoprecipitate endogenously expressed MOSPD2 in U937 cells.

Example 2

MOSPD2 and Migration of Metastatic Cell Lines

In order to assess the role of MOSPD2 in cancer cell migration, MOSPD2 expression in two metastatic cell lines, A2058 melanoma and MDA-231 breast cancer, was silenced using sh-control or sh-MOSPD2 lenti-virus particles.

In particular, sh-control or sh-MOSPD2 transduced A2058 or MDA-231 cells ($3\times10^5$) previously starved for 3 hours in 0.5% FBS/RPMI-1640 were seeded in the upper chamber of a QCM 24-well, 5 μm pore, migration assay plate (Corning-Costar, Corning, NY), followed by incubation for 24 hours in the presence of 10% FBS/RPMI-1640 and EGF (200 ng/ml, Peprotech Israel) in the lower chamber. Subsequently, the cells which migrated to the lower compartment were stained with crystal violet before images were taken.

FIGS. 1A-1D demonstrate that sh-MOSPD2 lenti-virus particles have profoundly decreased protein expression and inhibited cancer cell migration in vitro.

Example 3

MOSPD2 and Cell Proliferation

To determine whether the inhibitory effect on cell migration subsequent to MOSPD2 silencing is secondary to fundamental cell function such as proliferation, sh-control or sh-MOSPD2 lenti-virus particle transduced MDA-231 breast cancer cells were tested for proliferation over a period of 3 days.

Specifically, sh-control or sh-MOSPD2 lenti-virus transduced MDA-231 cells were seeded in 6 well plates ($10^4$ per well). The cells were counted by FACS every 24 hours in triplicates for 3 consecutive days.

Figure 2:
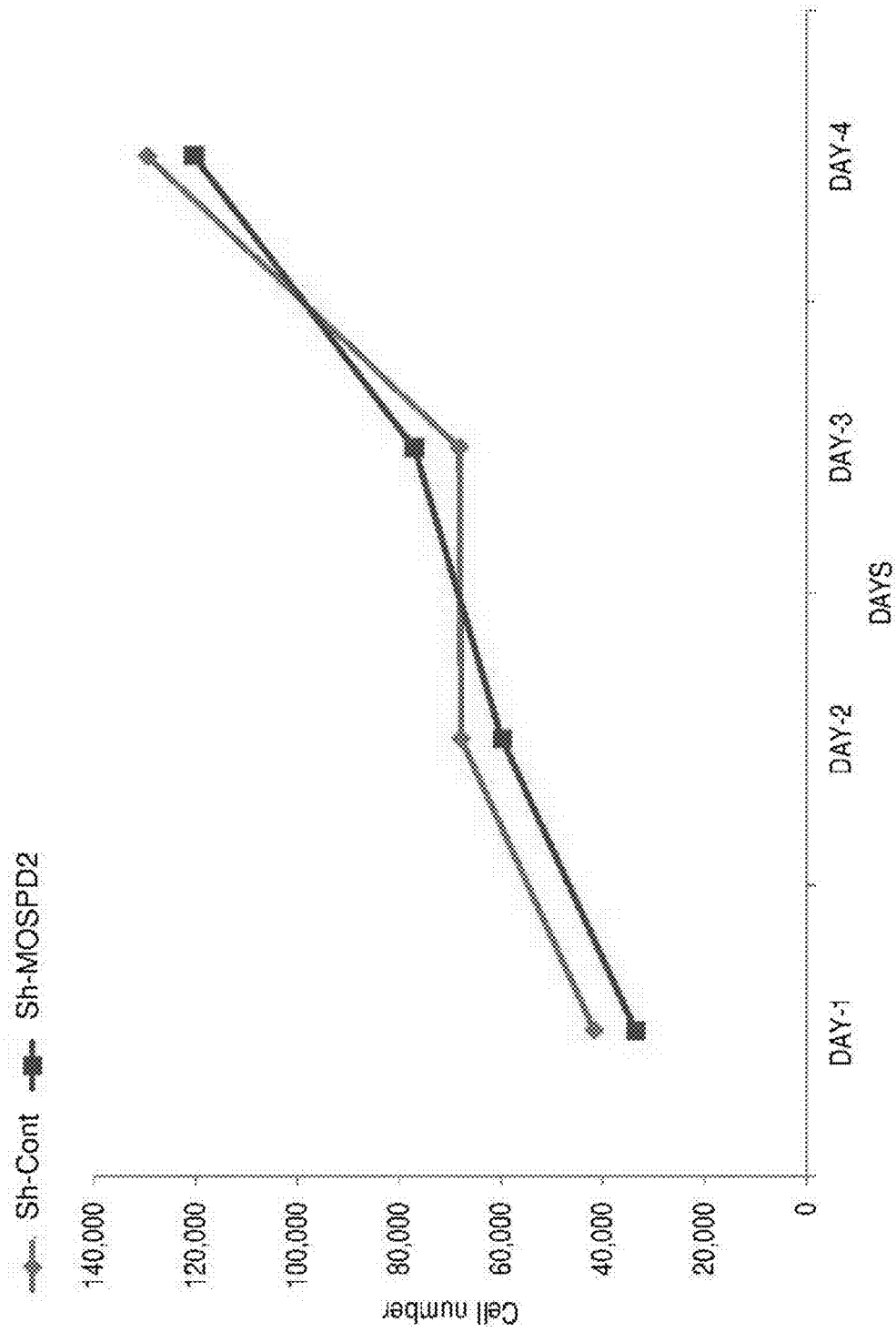
FIG. 2 presents a graph showing cell proliferation rates for MDA-231 breast cancer cells transduced with sh-control or sh-MOSPD2 lenti-virus particles. MDA-231 cells were seeded as described and collected and counted every 24 hours for three consecutive days. The results are expressed as mean±standard deviation of triplicates. These results demonstrate that silencing of MOSPD2 did not affect cell viability or proliferation of MDA-231 cells.

The data shown in FIG. 2 indicate that MOSPD2 is not essential for the proliferation of these cells, suggesting a regulatory role for MODPD2 specifically in migration.

Example 4

MOSPD2 and Cell Metastasis

To assess the role of MOSPD2 in disseminating cancer cells to organs beyond the original site of cancer, the extent of lung metastasis in sh-control or sh-MOSPD2 lenti-virus particle-transduced MDA-231 breast cancer cells were adoptively transferred into immune-deficient mice. In another model in which the site of inception occurs in the breast, immunodeficient mice were inoculated with sh-control or sh-MOSPD2 lenti-virus particle-transduced MDA-231 breast cancer cells in the mammary fat pad.

Pathological examination: Histology slides were stained with hematoxylin/eosin (H&E). Formalin-fixed tissue was dehydrated, embedded in paraffin, and sectioned at 4 μm thickness. The H&E staining was calibrated on a Leica staining module. The slides were warmed to 90° C. for 7 minutes and then processed according to a fully automated protocol. After sections were dewaxed and rehydrated, slides were stained for 7 minutes in Gill's Hematoxylin No. 3 (Surgipath), washed, dipped in acidic alcohol, and washed. After short dipping in 70% ethanol and 96% ethanol, slides were stained for 4 minutes in eosin (Sigma), and dehydrated in 96% ethanol and then twice in 100% ethanol for 1 minute each time. After a run on an automated stainer was completed, sections were cleared in xylene for 10 seconds and mounted with Entellan. Mean tumor area comprises the maximal lung tumor area measured for each mouse.

Systemic: $10^6$ sh-control or sh-MOSPD2 lenti-virus transduced MDA-231 cells were injected into the tail vein of 8 weeks old female SCID mice (C.B-17/IcrHsd-Prkdc$^{scid}$, Harlan Israel). Mice were sacrificed after 4 weeks. Lungs were excised for histopathologic examination. The results in FIG. 3A show that silencing MOSPD2 expression significantly (p=0.023) inhibits the presence of metastatic breast cancer cells in the lungs by more than 50% (metastasis area).

Figure 3B:
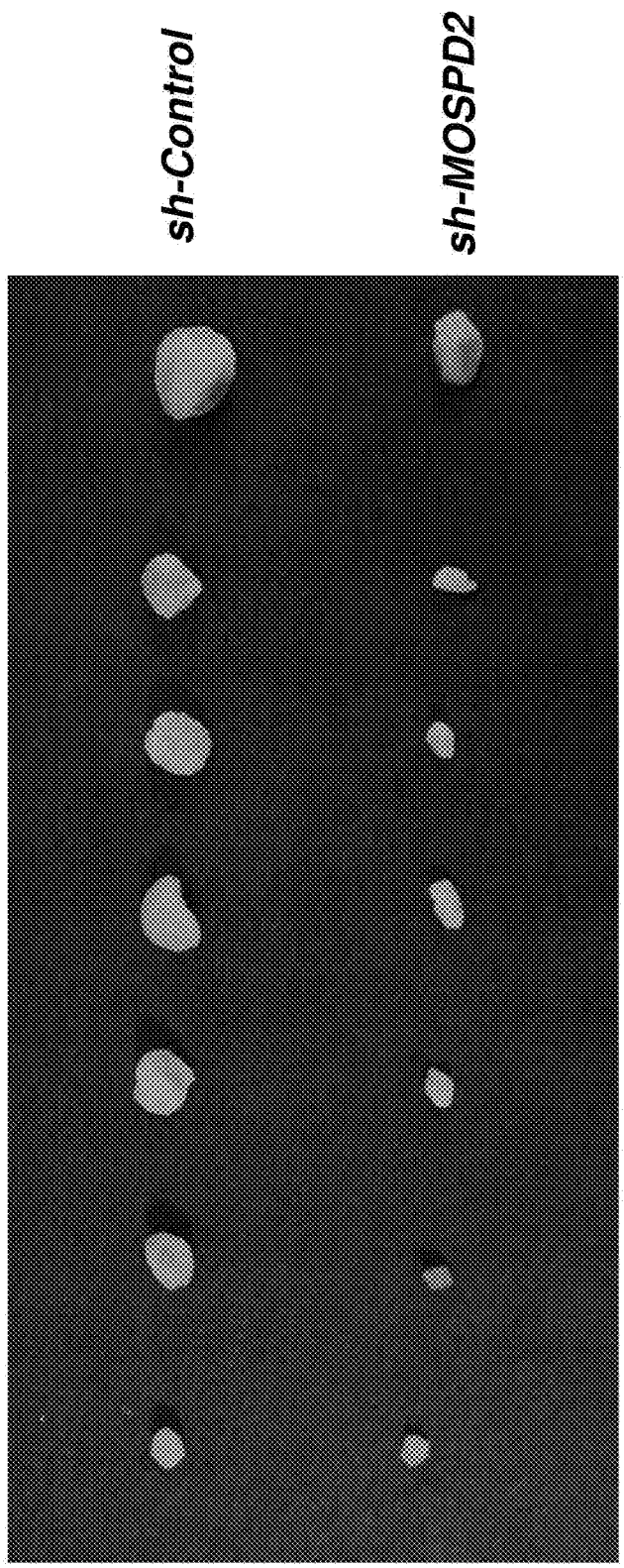

Orthotopic: $5\times10^6$ sh-control or sh-MOSPD2 lenti-virus transduced MDA-231 cells were injected into the mammary fat pad of 8 weeks old female SCID mice (C.B-17/IcrHsd-Prkdc$^{scid}$, Harlan Israel). Mice were sacrificed after 10 weeks. Ipsilateral inguinal lymph node and the lungs were excised for examination. Macroscopic examination showed that the vast majority of lymph nodes excised from mice transferred with sh-control cells were overwhelmingly bigger than those from mice transferred with sh-MOSPD2 treated cells (FIG. 3B). Moreover, the mean metastasis area measured in the lungs of mice transferred with sh-MOSPD2 treated cells was reduced by more than 50% compared to the control group (FIG. 3C).

The ratio of MOSPD2 mRNA silencing in sh-MOSPD2 injected cells was ~80%, as determined by Q-PCR as described in the Materials and Methods.

These results demonstrate that MOSPD2 plays a major role in breast cancer metastasis.

Example 5

MOSPD2 Expression in Various Types of Cancer

To determine whether MOSPD2 expression is associated with the transformation of cells from normal to cancerous, slides carrying normal and cancerous tissues were screened using anti-MOSPD2 antibody as described in the Materials and Methods section.

Figure 4A:
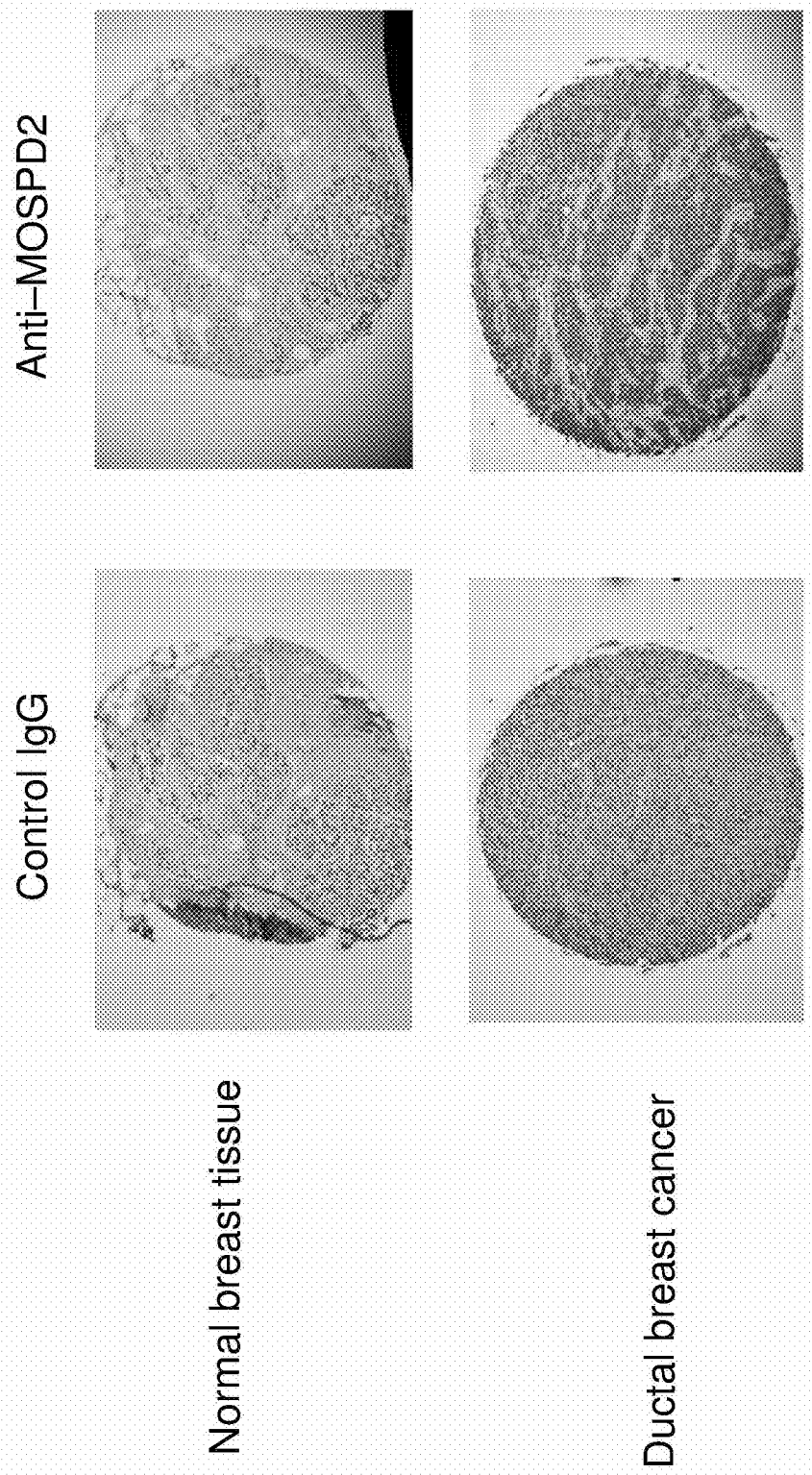
FIGS. 4A-4E show images comparing MOSPD2 expression levels of various human cancer tissues to those of their respective normal tissue counterparts. Slides containing various normal and cancerous human tissues were stained with control or anti-MOSPD2 antibody. Cancer tissues that stained positively for MOSPD2 are shown.
Figure 4B:
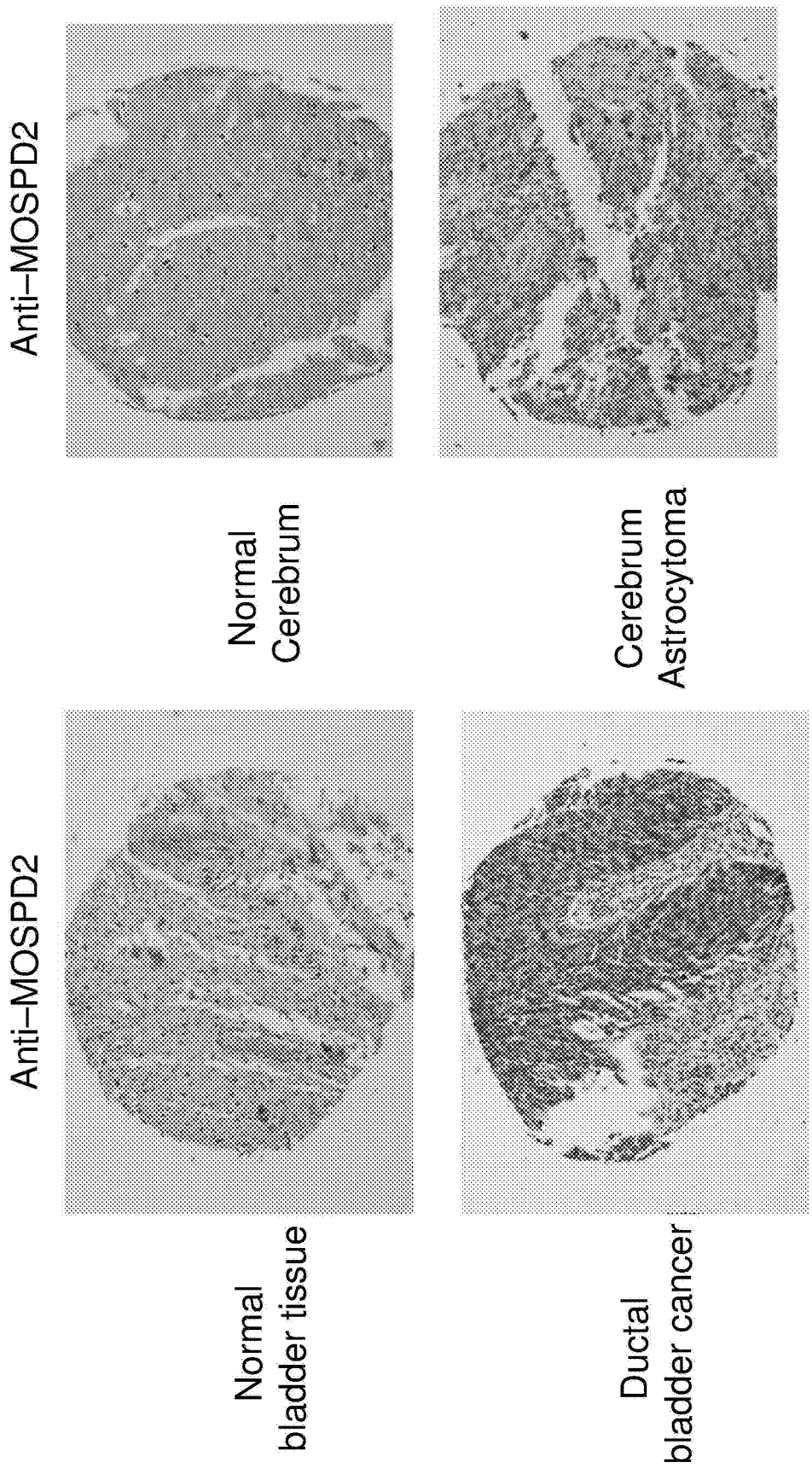
Figure 4C:
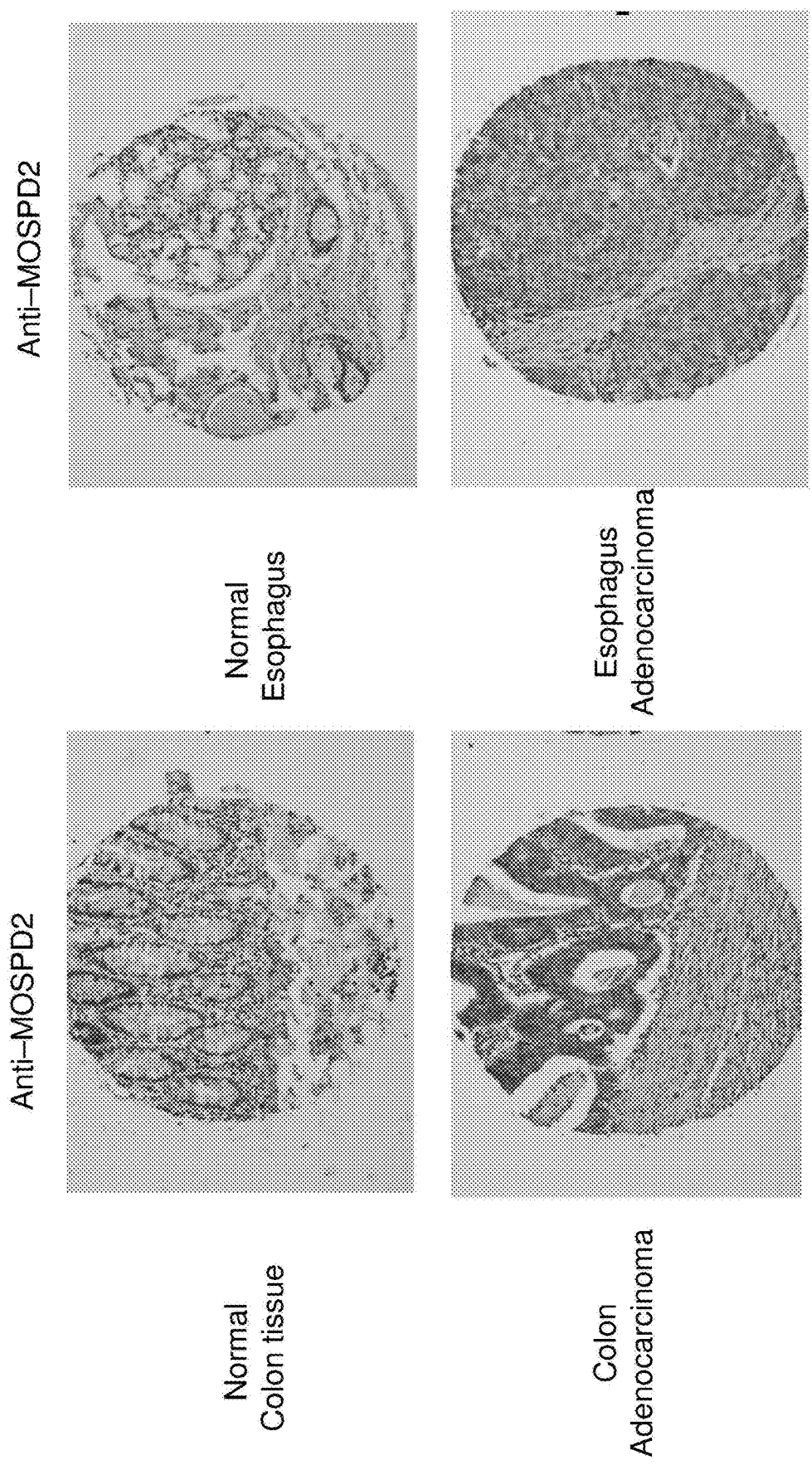
Figure 4D:
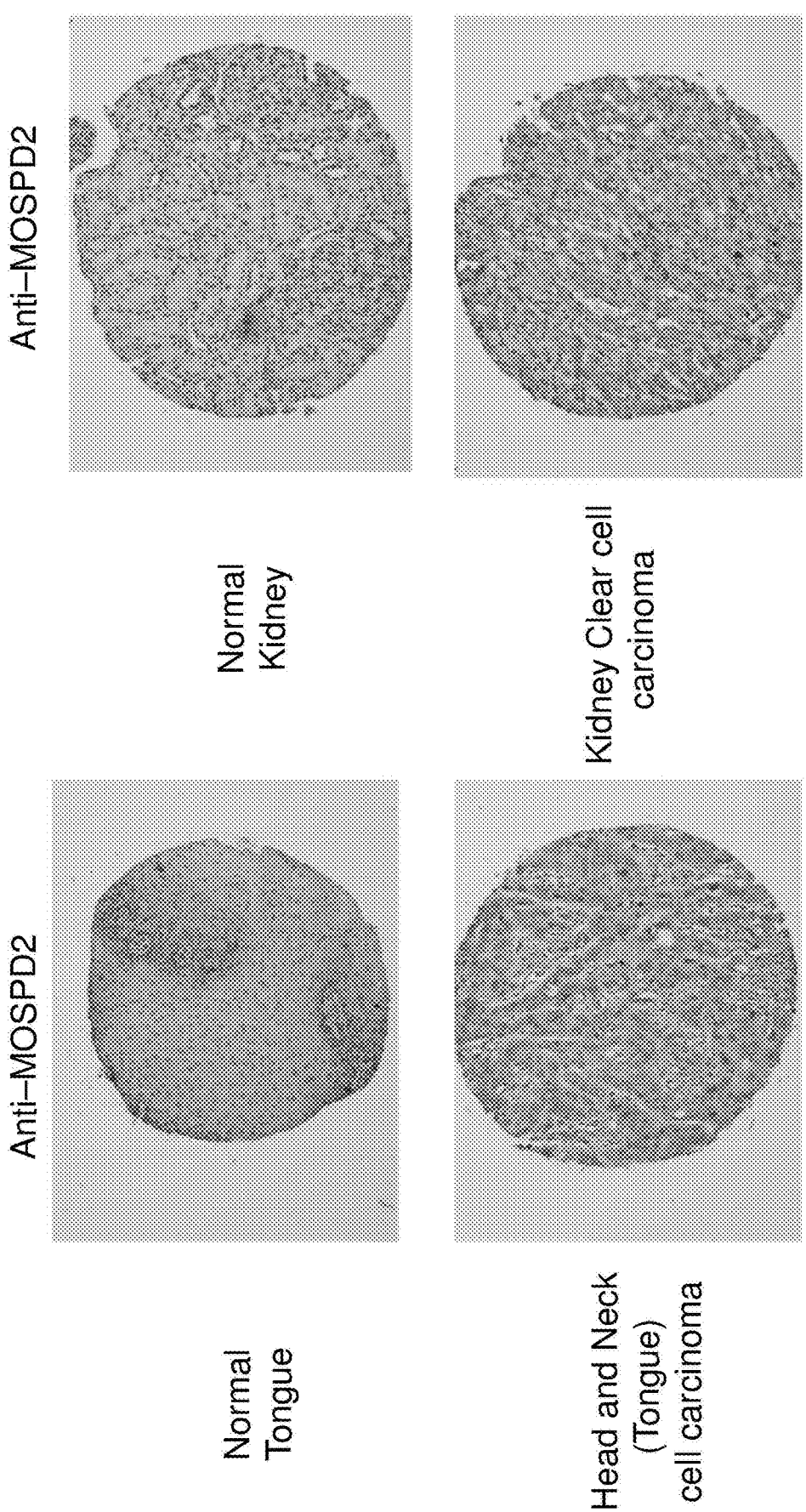
Figure 4E:
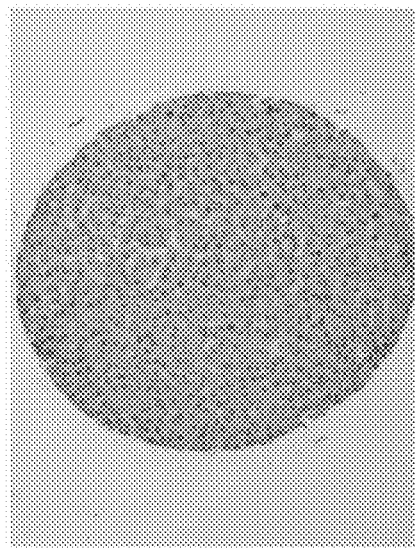
Figure 4E:
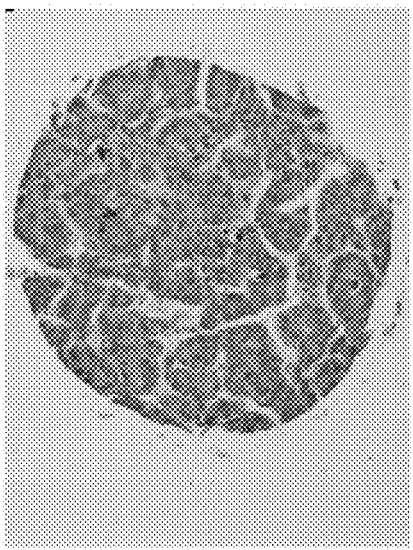

FIG. 4A shows representative staining of normal and cancerous breast tissue. While normal and cancerous breast tissues were negatively stained with control IgG antibody, anti-MOSPD2 antibody distinctively stained cancerous tissues only. Similarly, MOSPD2 is not expressed in normal bladder, brain, colon, esophagus, tongue, kidney and hepatic tissues, but is upregulated when these tissues turn cancerous (FIGS. 4B-4E). These results suggest that in various tissues, MOSPD2 expression is associated with transformation of normal tissue to cancerous tissue.

Example 6

MOSPD2 Gene Knockdown and Cancer Cell Migration

In vitro: To achieve sustainable knockdown of MOSPD2, MDA-231 breast cancer cells were transduced with lentiviral particles that contain the CRISPR-CAS9 gene editing system as described in the Materials and Methods section. Control or MOSPD2 CRISPR-CAS9 lenti-viral particles transduced MDA-231 cells were tested for migration similar to the method described in Example 2. Control or MOSPD2 CRISPR-CAS9 lenti-viral particles transduced MDA-231 cells ($3\times10^5$) were seeded in the upper chamber, followed by incubation for 2-4 hours. Subsequently, the number of cells which migrated to the lower compartment was determined by FACS.

Figure 5A:
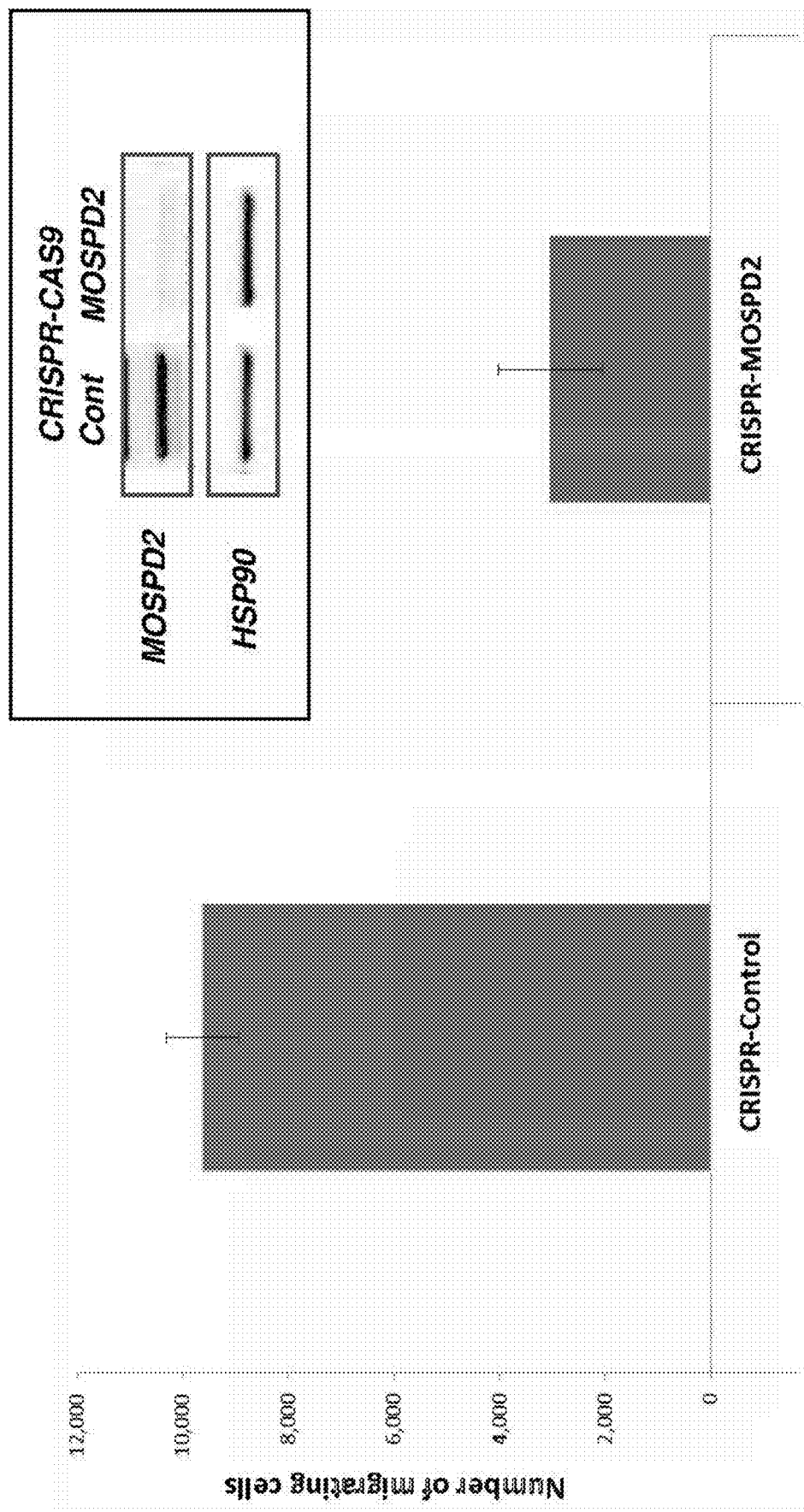
FIGS. 5A and 5B show the results of cancer cells transduced with control or MOSPD2 CRISPR-CAS9 lenti-virus particles, that were tested in a trans-well migration assay in which cells were seeded at the upper compartment and attracted to the lower compartment using medium supplemented with 10% FCS and EGF (200 ng/ml). The graph shown in FIG. 5A was determined by fluorescence-activated cell sorting (FACS) with results expressed as mean±standard deviation of triplicates. The images shown in FIG. 5B are from visual recordation.
Figure 5B:
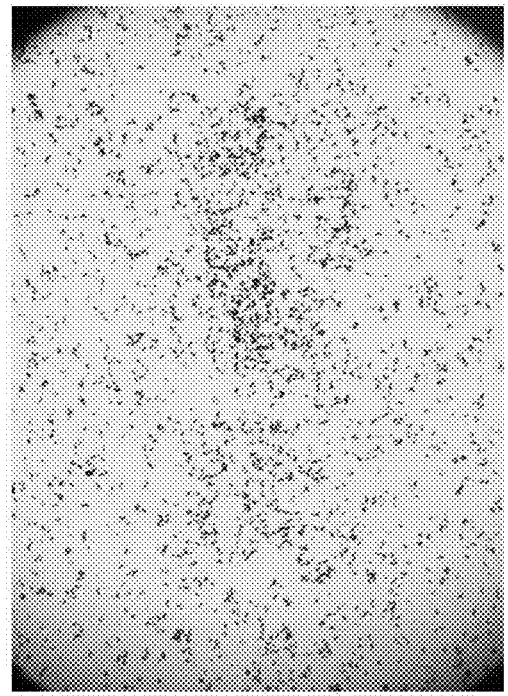
Figure 5B:
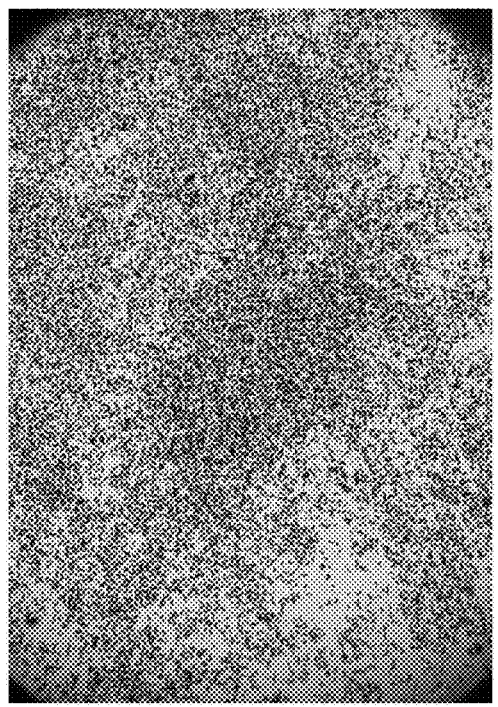

FIGS. 5A and 5B show that introducing the CRISPR-CAS9 system for MOSPD2 in MDA-231 cancer cells abolished protein expression and consequently profoundly inhibited migration of the cells in a trans-well assay.

To test the effects of MOSPD2 silencing by CRISPR-CAS9 on chemokine receptor-driven signaling events, phosphorylation levels of ERK, AKT and FAK were studied as described in the Materials and Methods. In accordance with the migration assay results, silencing MOSPD2 by the CRISPR-CAS9 system compared to control completely prevented phosphorylation of AKT and distinctly inhibited phosphorylation of ERK and FAK (see Western Blots in FIG. 5C) in cells exposed to EGF.

Figure 5D:
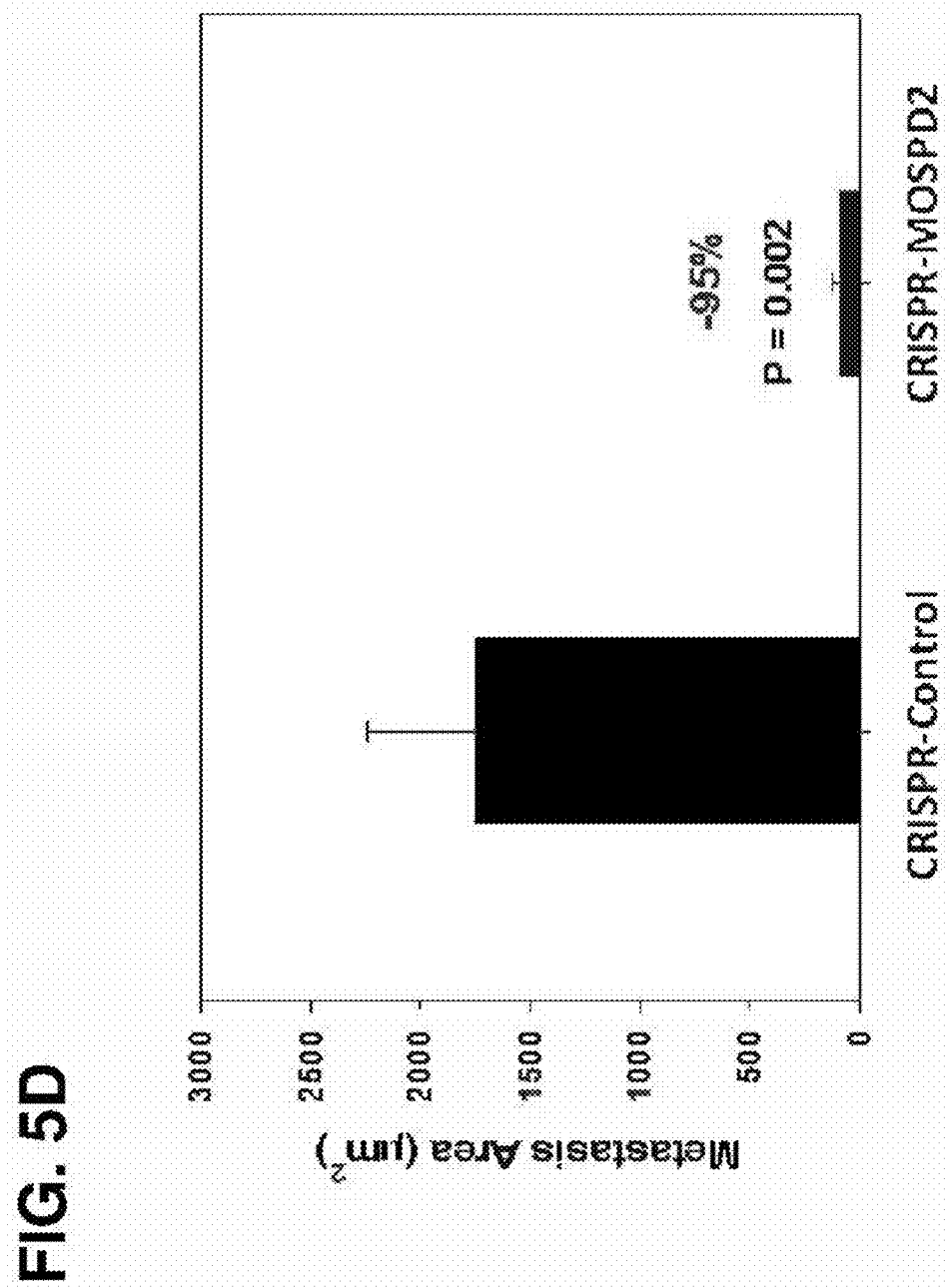
FIG. 5D shows in vivo test results of metastasis of MDA-231 breast cancer cells transduced with control or MOSPD2 CRISPR-CAS9 lenti-virus particles.

In vivo: $10^6$ CRISPR-control or CRISPR-MOSPD2 lentivirus transduced MDA-231 cells were injected into the tail vein of 8 weeks old female SCID mice (C.B-17/IcrHsd-Prkdcscid, Harlan Israel). Mice were then sacrificed after 3 weeks. Lungs were excised for histopathologic examination similar to the method described in Example 4. FIG. 5D shows that silencing MOSPD2 by the CRISPR-CAS9 system significantly inhibited the presence of metastatic breast cancer cells in the lungs by more than 95% (metastasis area).

Example 7

VB-201 and EGF Signaling Pathway

In vitro: To test the effect of VB-201 on epidermal growth factor (EGF)-induced phosphorylation, MDA-231 breast cancer cells ($10^6$) were starved for 3 hours in 0.5% FCS medium, followed by incubation with various concentrations of VB-201 (1 μg/ml, 5 μg/ml, and 10 μg/ml) or a solvent control for 20 minutes. The MDA-231 cells were then activated with EGF (200 ng/ml) for 10 min. Phosphorylation of AKT was then analyzed by Western Blot. HSP90 was used for a loading control.

Figure 6:
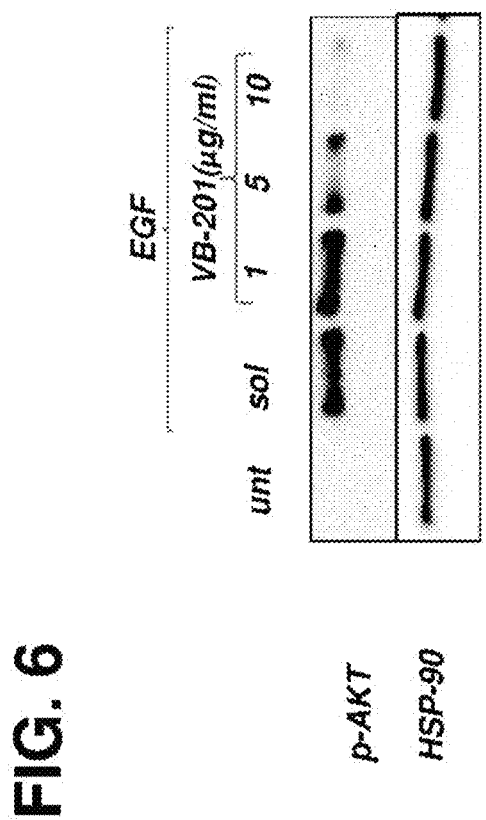
FIG. 6 presents an image of Western Blots showing the effect of VB-201 in inhibiting EGF induced phosphorylation of AKT in MDA-231 cancer cells.

As shown in FIG. 6, VB-201 at 10 μg/ml nearly completely inhibits EGF induced phosphorylation of AKT, with significant inhibition observed at 5 μg/ml.

Example 8

Generation of Anti-MOSPD2 (Fab)2 Monoclonal Antibodies

Anti-MOSPD2 $(Fab')_2$ monoclonal antibodies (mAb) were obtained using the HuCAL PLATINUM® Platform (Bio-Rad AbD Serotec, GmnH) which contains a selection of phage displayed human Fab.

Briefly, recombinant protein of the extracellular region of MOSPD2 fused to human Fc was immobilized on a solid support. The HuCAL® library presented on phage particles was incubated with the immobilized antigen. Nonspecific antibodies were removed by extensive washing and specific antibody phages were eluted by adding a reducing agent. Antibody DNA was isolated as a pool and subcloned into an *E. coli* expression vector to generate bivalent $F(ab')_2$ mAb. Colonies were picked and grown in a microtiter plate. The cultures ware lysed to release the antibody molecules and screened for specific antigen binding by ELISA and FACS. Unique antibodies were expressed and purified using one-step affinity chromatography, and then tested again by ELISA and FACS for specificity.

Figure 7:
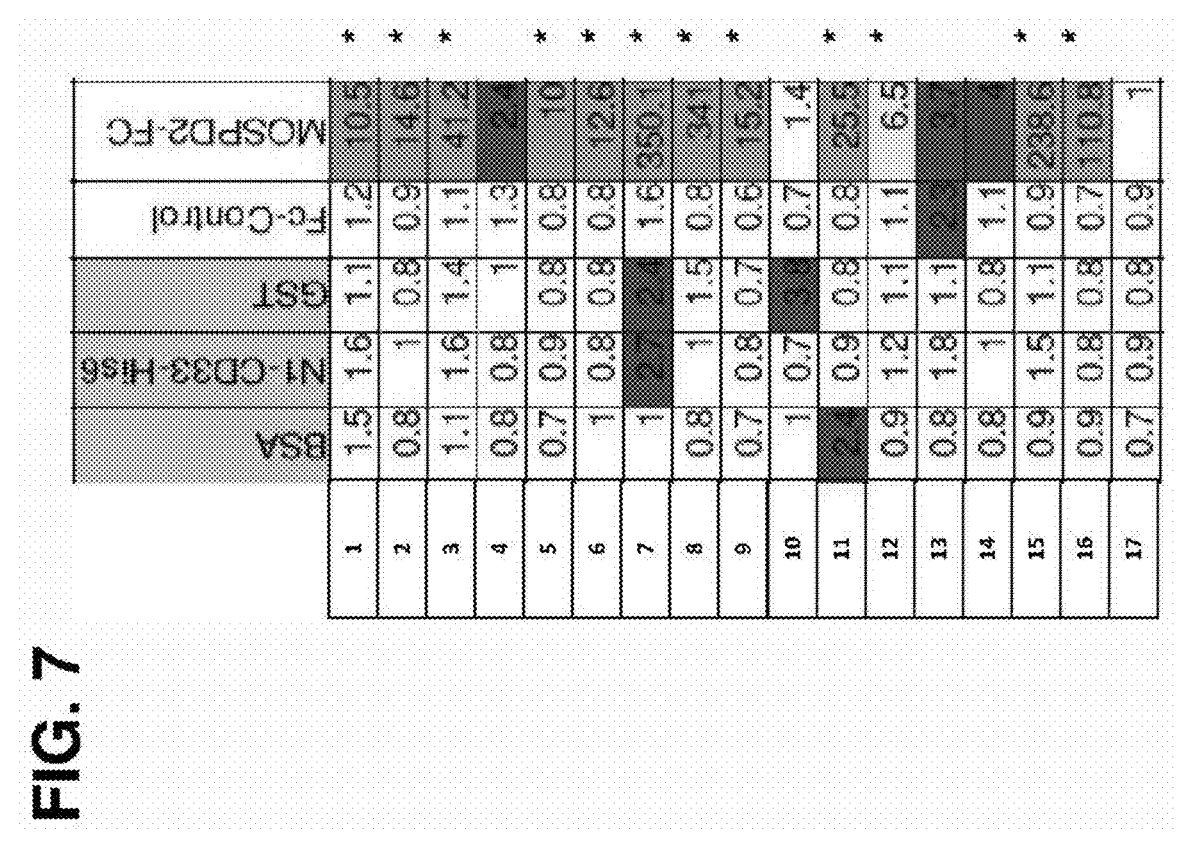

FIG. 7 lists 17 anti-MOSPD2 $F(ab')_2$ monoclonal antibody clones that were identified following a primary screen for binding to cells over-expressing MOSPD2. Further analysis of the clones for MOSPD2 binding with ELISA identified 12 clones having O.D. values greater than 5 times over background (* in FIG. 7).

Example 9

Anti-MOSPD2 F(Ab)2 mAb Bind Human MOSPD2 Overexpressed on Cells

A2058 melanoma cells were transfected with HA-tagged human MOSPD2 to generate cells overexpressing MOSPD2.

Binding of the 12 antibody clones identified in Example 8 to MOSPD2 was then tested using flow cytometry with these cells. Specifically, $10^5$ cells were incubated with 2.5 μg of $F(ab')_2$ mAb at 4° C. for 1 hr in 100 μl of FACS buffer (PBS+2% FCS+0.02% sodium azide). Cells were then washed, resuspended in FACS buffer and stained for 30 min at 4° C. with Alexa-Fluor 647-conugated $(Fab')_2$ goat anti-human IgG, $F(ab')_2$ 1:200 (Cat #109-606-097, Jackson Immunoresearch, PA). Cells were washed, resuspended in FACS buffer and analyzed on a FACS-Calibur device.

Figure 8A:
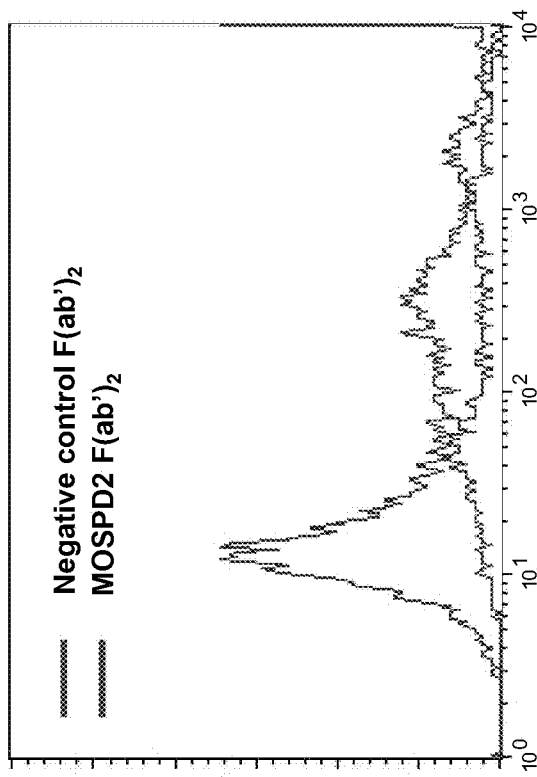
FIGS. 8A-8B show binding of two representative anti-MOSPD2 F(ab')$_2$ monoclonal antibody (mAb) clones to cells overexpressing MOSPD2.
Figure 8B:
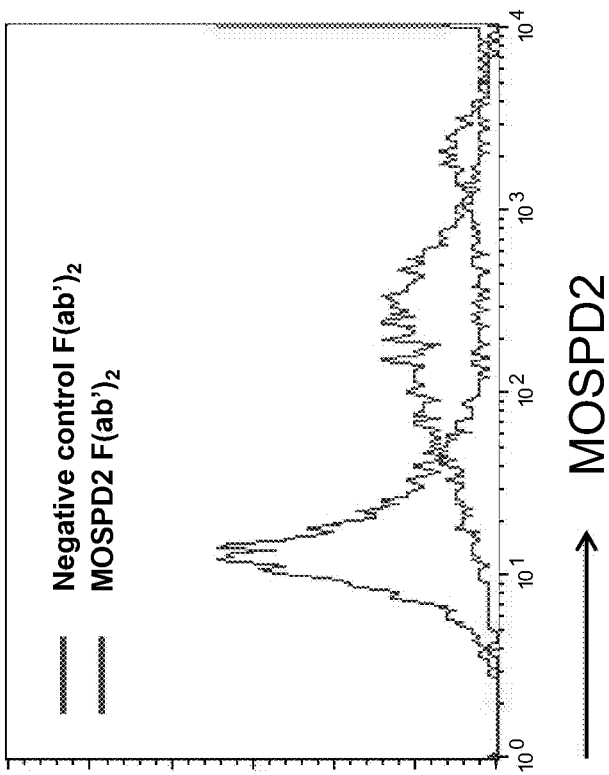

All clones positively stained the cells. Representative staining for 2 clones is shown in FIGS. 8A-8B. A clone that was not identified as a positive clone in Example 8 with ELISA was used as a negative control.

Example 10

Figure 9:
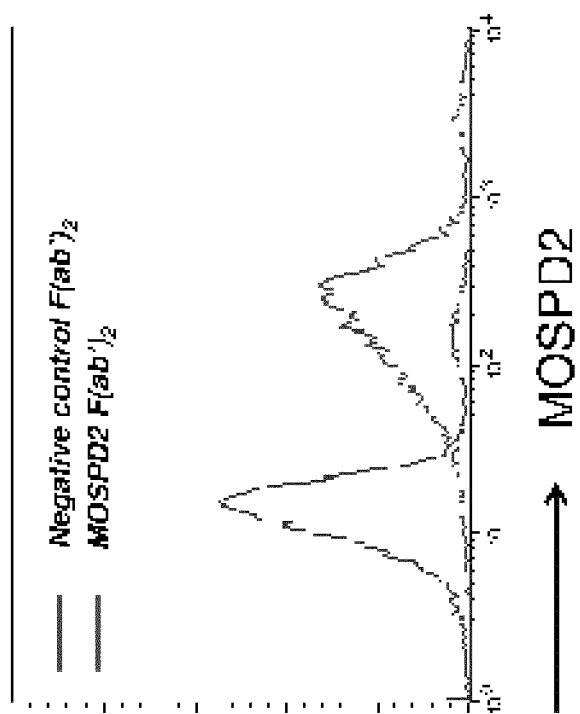
FIG. 9 shows binding of a representative anti-MOSPD2 F(ab')$_2$ mAb to MOSPD2 expressed by MDA-231 breast cancer cells.

Anti-MOSPD2 F(Ab)2 mAb Specifically Binds Endogenous MOSPD2 on Human Breast Cancer Cells Anti-MOSPD2 $F(ab')_2$ mAb was tested for binding to surface expressed endogenous MOSPD2 on MDA-231 breast cancer cells. Cells were stained with anti-MOSPD2 $F(ab')_2$ mAb as described in Example 9. Staining with 2 different clones is shown in FIG. 9. The ELISA negative clone described in Example 9 was used as negative control. FIG. 9 shows that anti-MOSPD2 $F(ab')_2$ mAb specifically binds endogenous MOSPD2 on human breast cancer cells.

Figure 10A:
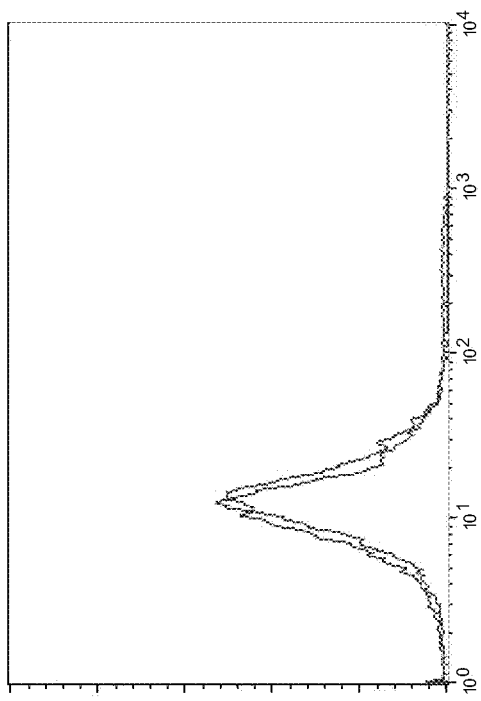
FIGS. 10A-10B show anti-MOSPD2 F(ab')$_2$ mAb binds to MDA-231 cells (FIG. 10A), but does not bind to MOSPD2-silenced MDA-231 cells (FIG. 10B).
Figure 10B:
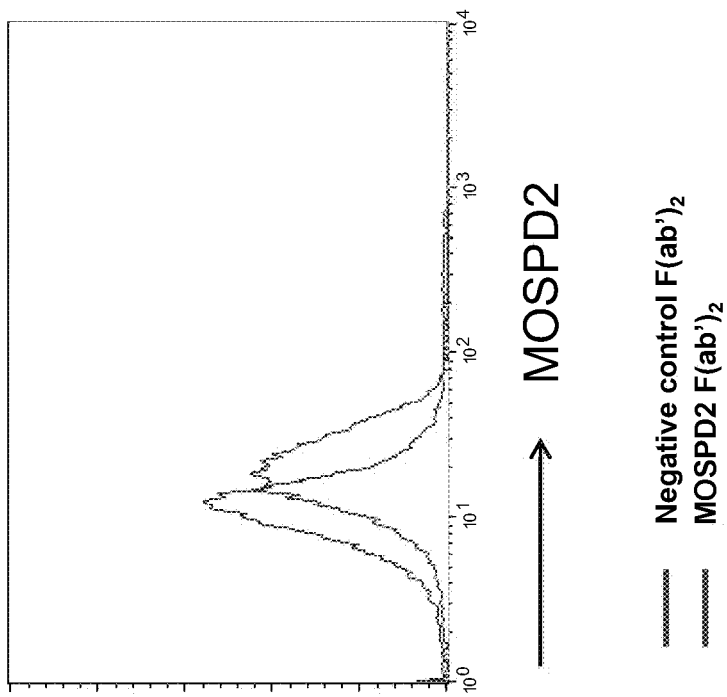

To further demonstrate antigen binding specificity, MOSPD2 gene expression was silenced in MDA-231 cells using CRISP-CAS9 lentiviral particles. MOSPD2-silenced cells and non-silenced cells were combined with anti-MOSPD2 $(Fab')_2$ mAb or a negative control and analyzed with FACS. FIGS. 10A-10B show anti-MOSPD2 $F(ab')_2$ mAb binds to MDA-231 cells (FIG. 10A), but does not bind to MOSPD2-silenced MDA-231 cells (FIG. 10B).

Example 11

Figure 11B:
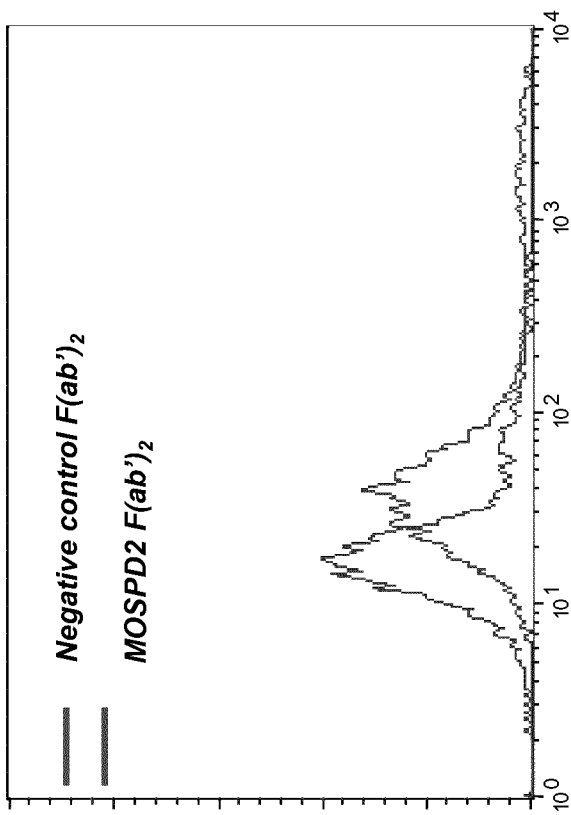
FIGS. 11A-11B show anti-MOSPD2 F(ab')$_2$ mAb binds to MOSPD2 on A2058 melanoma and HepG2 liver cancer cell lines.
Figure 11A:
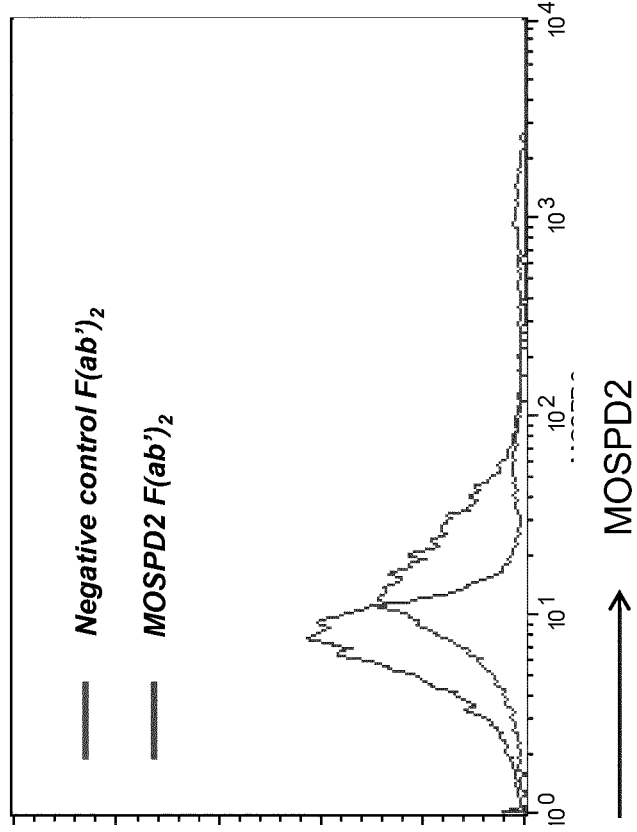

Anti-MOSPD2 F(Ab)2 mAb Binds Endogenous MOSPD2 on Melanoma and Liver Cancer Cells Anti-MOSPD2 $F(ab')_2$ mAb was tested for binding to surface expressed endogenous MOSPD2 on A2058 melanoma and HepG2 liver cancer cell lines. Cells were stained with anti-MOSPD2 $F(ab')_2$ mAb and tested for binding to MOSPD2 as described in Examples 9 and 10. FIGS. 11A-11B show that anti-MOSPD2 $F(ab')_2$ mAb specifically binds endogenous MOSPD2 on melanoma and liver cancer cells.

Example 12

Anti-MOSPD2 F(Ab)2 mAb Inhibits EGF-Induced Signaling in MDA-231 Cancer Cells

The effect of anti-MOSPD2 $F(ab')_2$ mAb on EGF-induced signaling in MDA-231 cancer cells was analyzed with Western blot. Specifically, MDA-231 cells were starved overnight with medium containing 0.5% FCS and then incubated for 1 hr with anti-MOSPD2 $(Fab')_2$ mAb before adding EGF (100 ng/ml) for 5 min. Cells were washed and resuspended in lysis buffer, loaded onto a precast Criterion TGX gel (Bio-Rad, Hemel Hempstead, UK) and transferred onto nitrocellulose membrane. The membranes were blocked with 5% milk or BSA in Tris buffered saline and Tween 20 (TBST) for 1 hr, and then incubated with primary and secondary antibodies. Membranes were developed using an ECL kit (Thermo Scientific). Cells that were not treated with anti-MOSPD2 $F(ab')_2$ mAb (unt) were analyzed as a negative control. Heat shock protein (HSP)-90 protein levels were also analyzed as a protein loading control.

The following antibodies were used:
Primary antibodies: p-ERK1/2 (cat. no. M8159; 1:10,000) from Sigma (Israel); phospho-AKT (cat no. 9271; Ser 473, 1:1000) and phospho-EGF Receptor (cat no. 2236 1:1000) from Cell Signaling; and HSP-90 (cat. no. 13119; 1:500) from Santa Cruz Biotechnology (Santa Cruz, CA).

Secondary antibodies: HRP donkey anti-rabbit (1:5000) and HRP goat anti-mouse (1:3000) from Jackson ImmunoResearch (West Grove, PA, USA).

Figure 12:
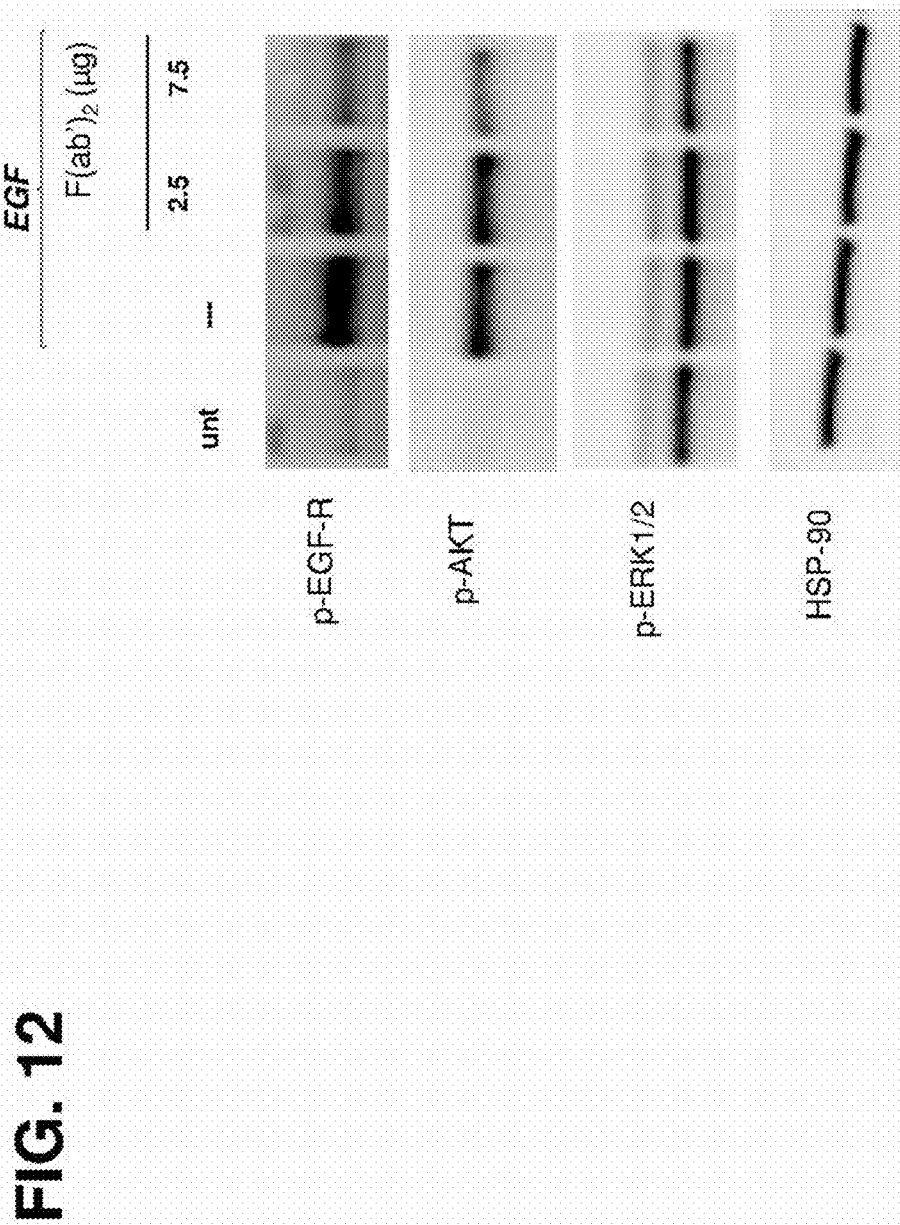
FIG. 12 shows that incubation of MDA-231 cells with anti-MOSPD2 F(ab')$_2$ mAb inhibited phosphorylation of EGF receptor (p-EGF-R), AKT (p-AKT) and ERK1/2 (p-ERK1/2).

As shown in FIG. 12, incubation of MDA-231 cells with anti-MOSPD2 (Fab)$_2$ mAb inhibited phosphorylation of the EGF Receptor (pEGF-R) as well as phosphorylation of AKT and ERK, which are mediators of the downstream signaling pathways associated with cell migration (p-AKT and p-ERK1/2, respectively).

Example 13

Anti-MOSPD2 F(ab)2 mAb Inhibits EGF-Induced Migration of MDA-231 Cancer Cells

The effect of anti-MOSPD2 F(ab')$_2$ mAb on EGF-induced migration of MDA-231 cancer cells was analyzed with trans-well migration as explained in Example 2. MDA-231 breast cancer cells ($3 \times 10^5$) were starved for 4-5 hr in RPMI medium containing 0.5% FCS and then incubated for 1 hr with anti-MOSPD2 F(ab')$_2$ mAb. EGF was dissolved and placed in the lower chamber (400 ng/ml) of a QCM 24-well migration assay plate (8 µm pores) (Corning-Costar, Corning, NY) which contained RPMI medium with 10% FCS. Cells were seeded in the upper chamber, followed by overnight incubation, after which the number of cells that migrated to the lower compartment was determined by FACS.

Figure 13:
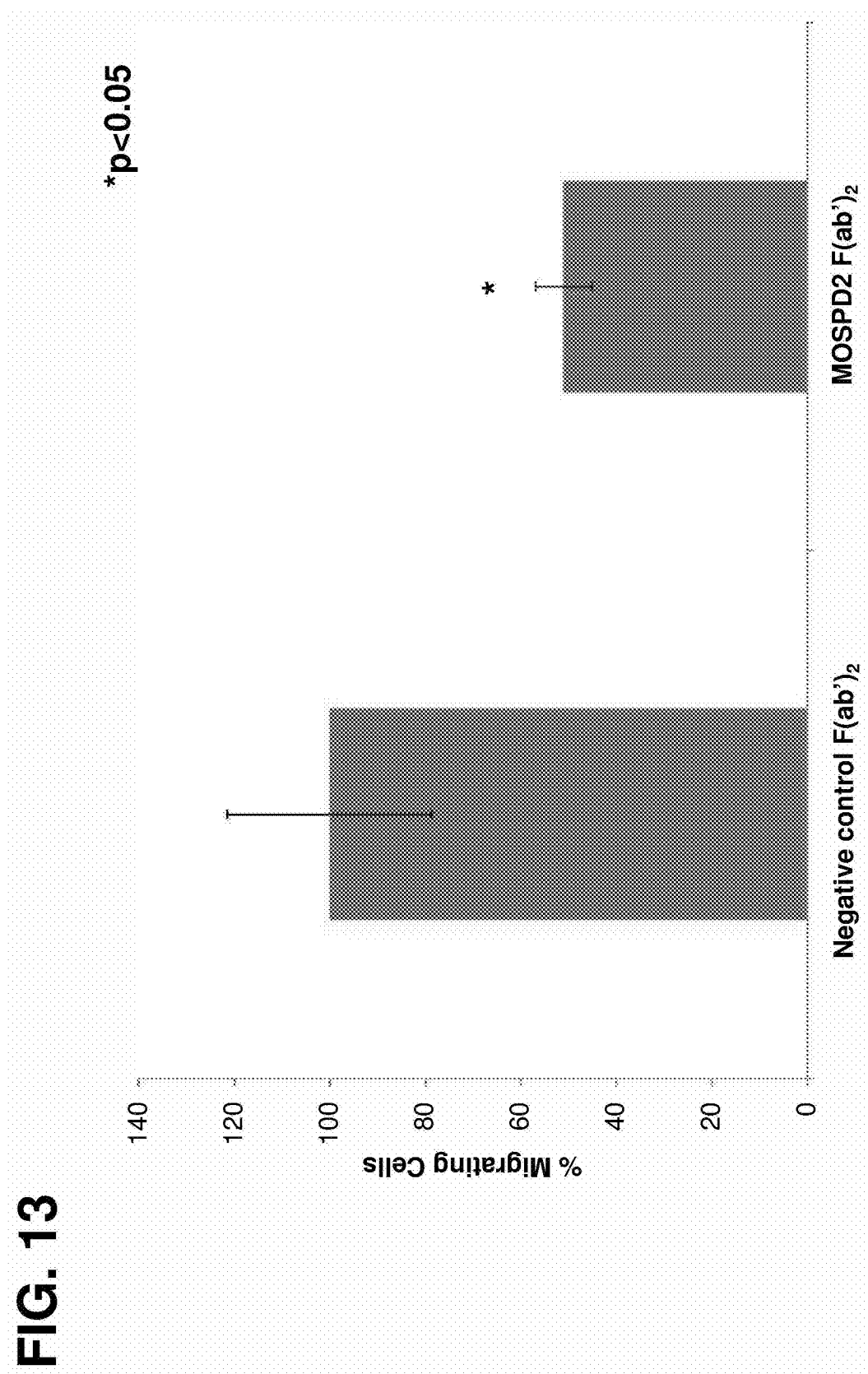
FIG. 13 shows anti-MOSPD2 F(ab')$_2$ mAb significantly inhibited EGF-induced trans-well migration of MDA-231 cells.

As shown in FIG. 13, F(ab')$_2$ mAb significantly inhibited EGF-induced trans-well migration of MDA-231 breast cancer cells.

Example 14

Defining Cellular Expression Specificity and Localization of MOSPD2

Figure 14A:
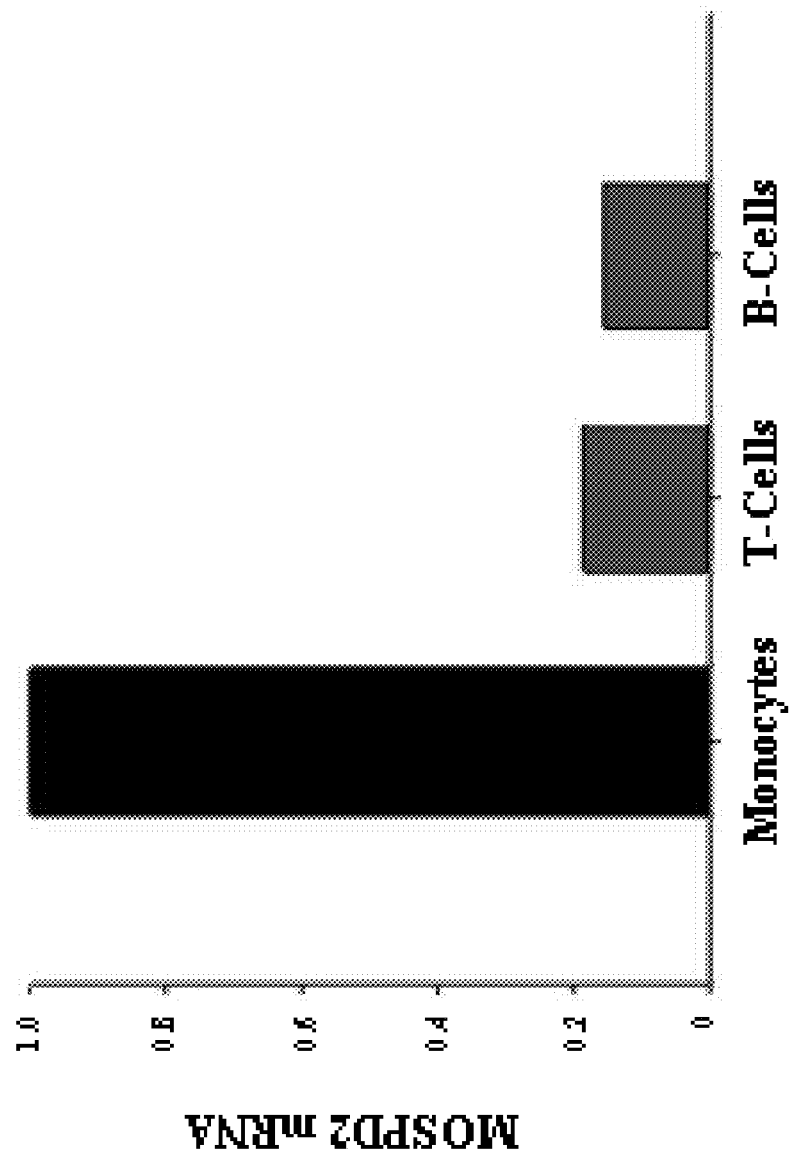

Analysis of different immune cell subpopulations indicated that MOSPD2 is expressed predominantly in CD14+ monocytes over T and B lymphocytes (FIG. 14A). To determine MOSPD2 mRNA expression level, RNA was extracted from cells using RNeasy mini kit (Qiagen, ValenVBa, CA). For cDNA preparation, 2 µg of RNA was combined with qScript reaction mix and qScript reverse transcriptase (Quanta Bioscience, Gaithersburg, MD). The reaction was placed in a thermal cycler (BioRad, Hercules, CA) and a run was programmed according to manufacturer's instructions. Real-time PCR reactions were performed on an Applied Biosystems 7300 real time PCR system (Grand Island, NY) using sets of primers for human MOSPD2, 28S to normalize RNA levels (BIOSEARCH TECHNOLOGIES, Petaluma, CA) and SYBR Green PCR Master Mix (Applied Biosystems, Warrington, UK).

Figure 14B:
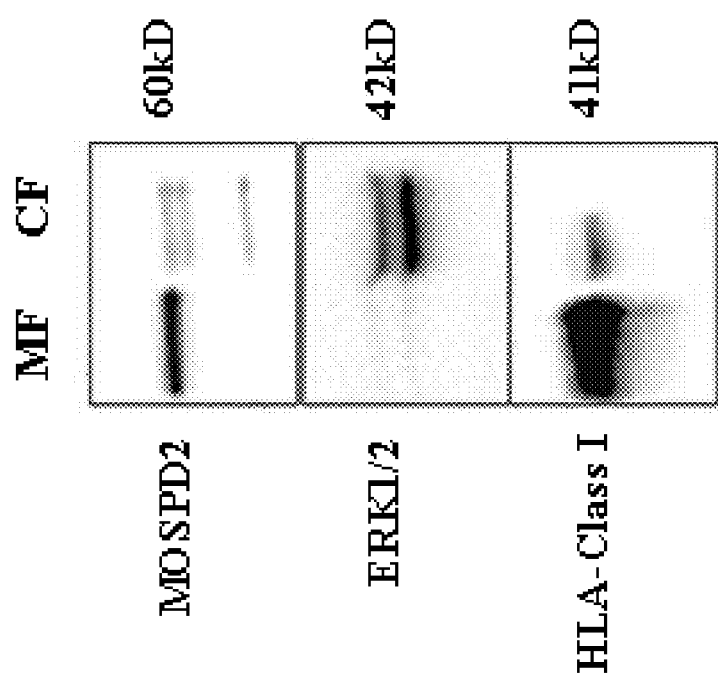
Figure 14C:
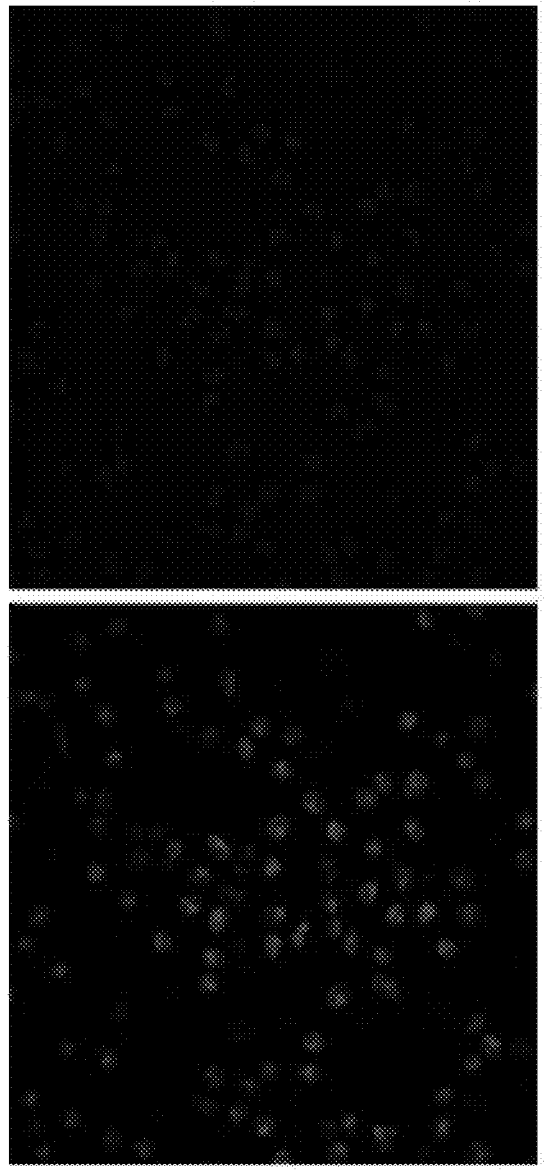

MOSPD2 is predicted to be a plasma membrane protein with one transmembrane region and one residue-long intracellular tail. Fractionation of cellular compartments, and immunofluorescence staining of human monocytes, and flow cytometry on HEK 293 cells transfected to overexpress HA-tagged MOSPD2 (performed according to the methods described above) revealed that MOSPD2 is a cell surface protein that is expressed on the plasma membrane of human monocytes (FIGS. 14B-14D, respectively).

Example 15

MOSPD2 is Expressed on Monocytes Infiltrated into Inflamed Tissues

Formalin-fixed tissues were dehydrated, embedded in paraffin, and sectioned at 4 µm. Immunostaining was fully calibrated on a Benchmark XT staining module (Ventana Medical Systems). After sections were dewaxed and rehydrated, anti-CD163 (Cell Marque, Rocklin, USA, MRQ-26) or anti-MOSPD2 diluted at 1:80 and 1:100, respectively, added rest for 40 minutes. Anti-CD163 staining was detected using UltraView universal Alkaline Phosphatase red detection kit (Ventana Medical Systems, 760-501) and anti-MOSPD2 staining was detected using UltraView universal DAB detection kit (Ventana Medical Systems, 760-500). When double staining was applied, MOSPD2 staining was performed first followed by CD163 staining. Slides were counterstained with hematoxylin (Ventana Medical Systems). After the run on the automated stainer was completed, slides were dehydrated consecutively in 70% ethanol, 95% ethanol and 100% ethanol for 10 sec each. Before cover slipping, sections were cleared in xylene for 10 sec and mounted with Entellan. MOSPD2 and CD163 stained slides were viewed using an Olympus BX51 microscope. Images were taken using a Nikon digital sight camera and NIS Elements Imaging Software.

Figure 15A:
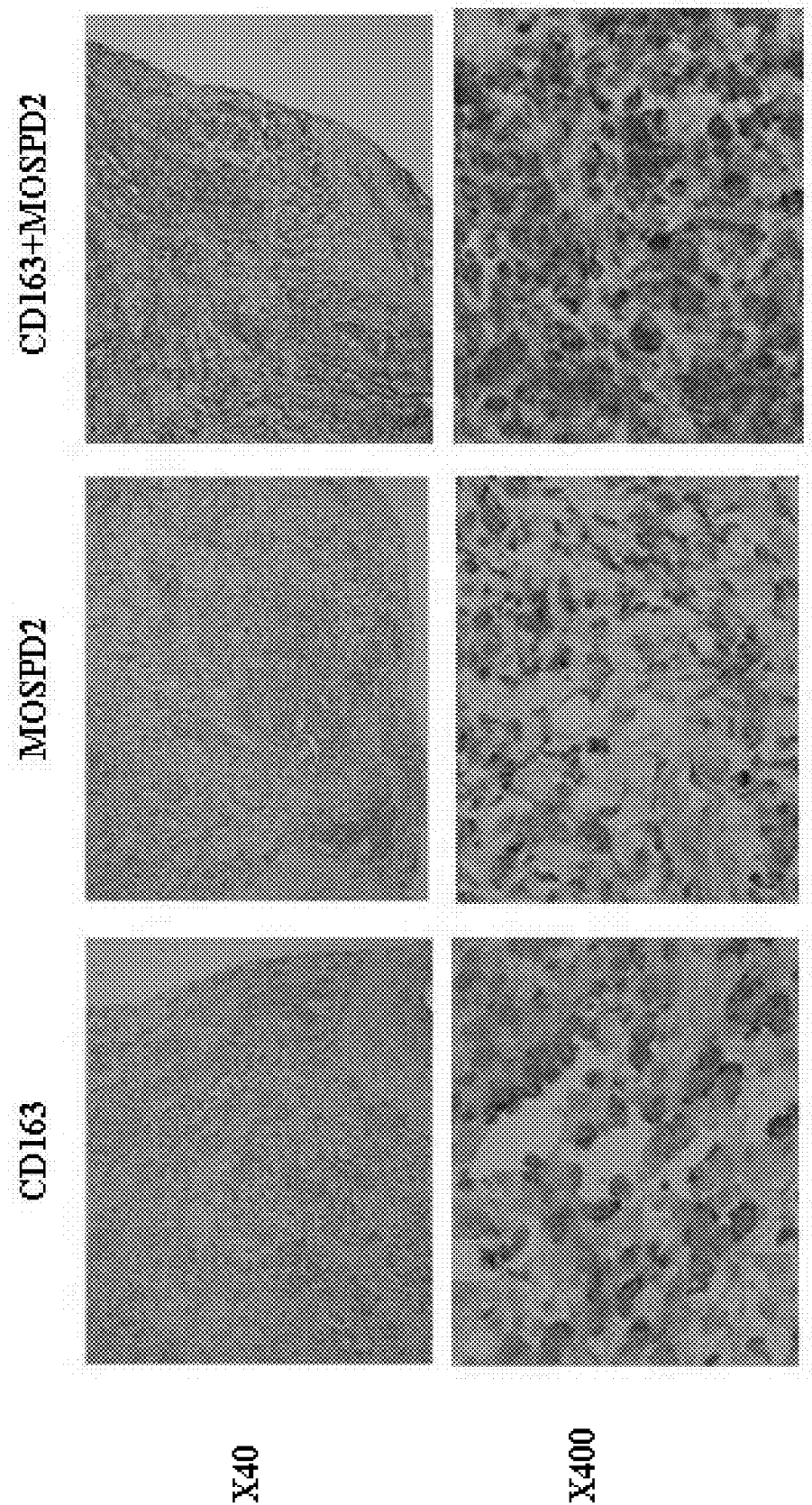
FIGS. 15A-15C show MOSPD2 is expressed on monocytes that have infiltrated into inflamed tissues.
Figure 15B:
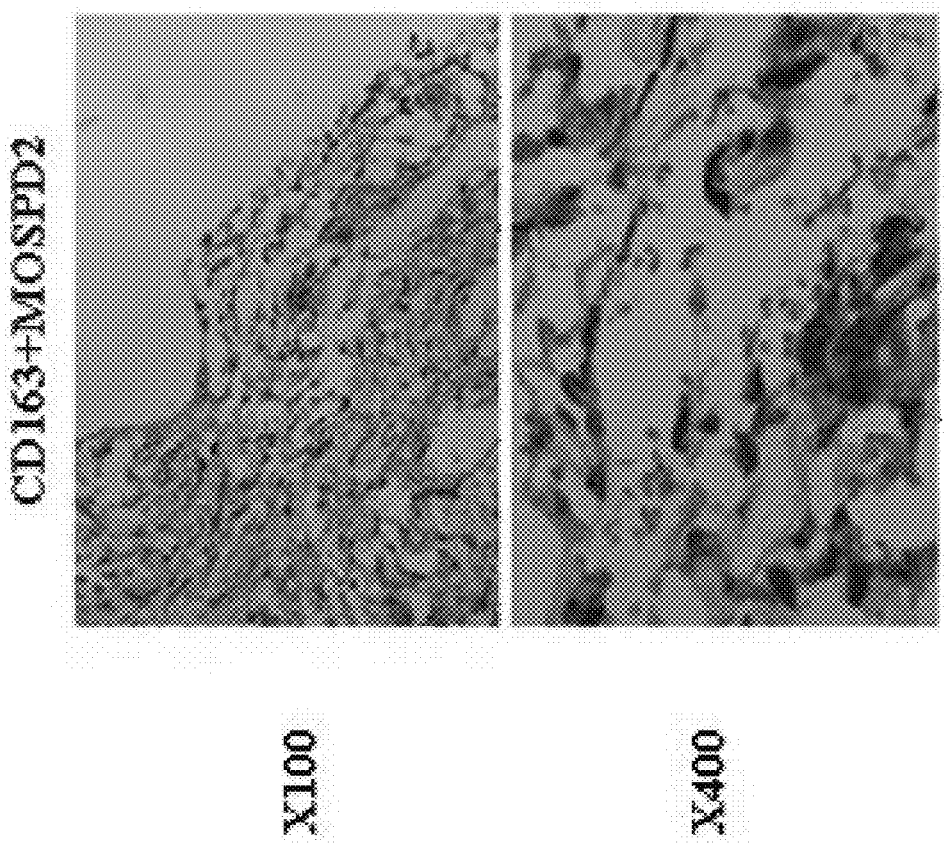
Figure 15C:
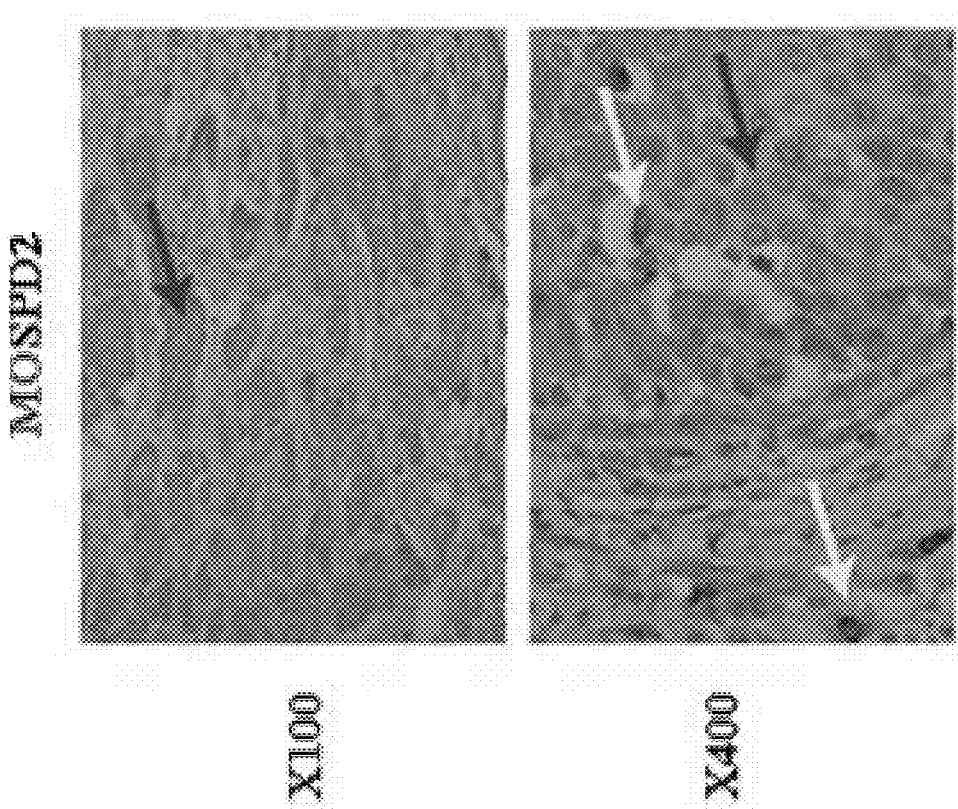

As shown in FIGS. 15A-15C, MOSPD2 is expressed on monocytes infiltrated into a variety of inflamed tissues. FIG. 15A shows the staining of synovial membrane from a rheumatoid arthritis patient for CD163, MOSPD2, or both CD163 and MOSPD2. FIG. 15B shows the staining of atherosclerotic carotid tissue for CD163, MOSPD2, or both CD163 and MOSPD2. FIG. 15C shows the staining of infiltrating ductal carcinoma breast tissue for MOSPD2. Dark arrows indicate positive staining for tumor cells. Light arrows indicate staining of infiltrating monocytes.

Example 16

MOSPD2 Promotes Monocyte Migration

Figure 16A:
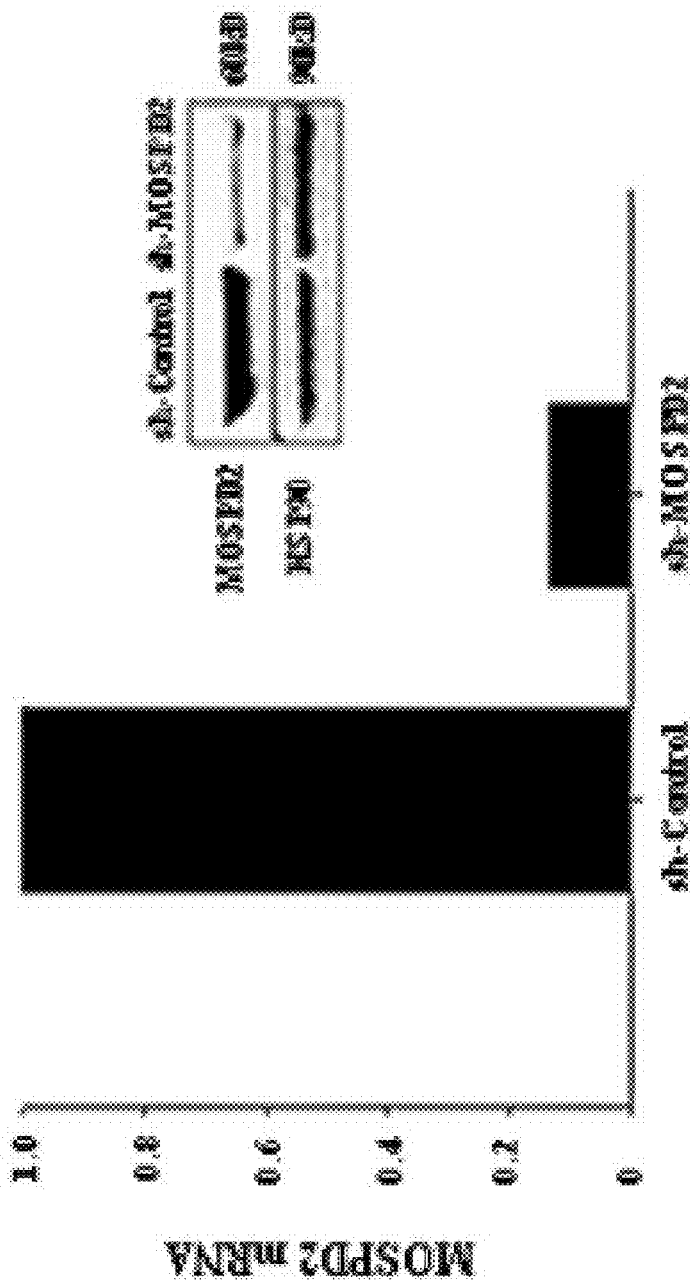
Figure 16B:
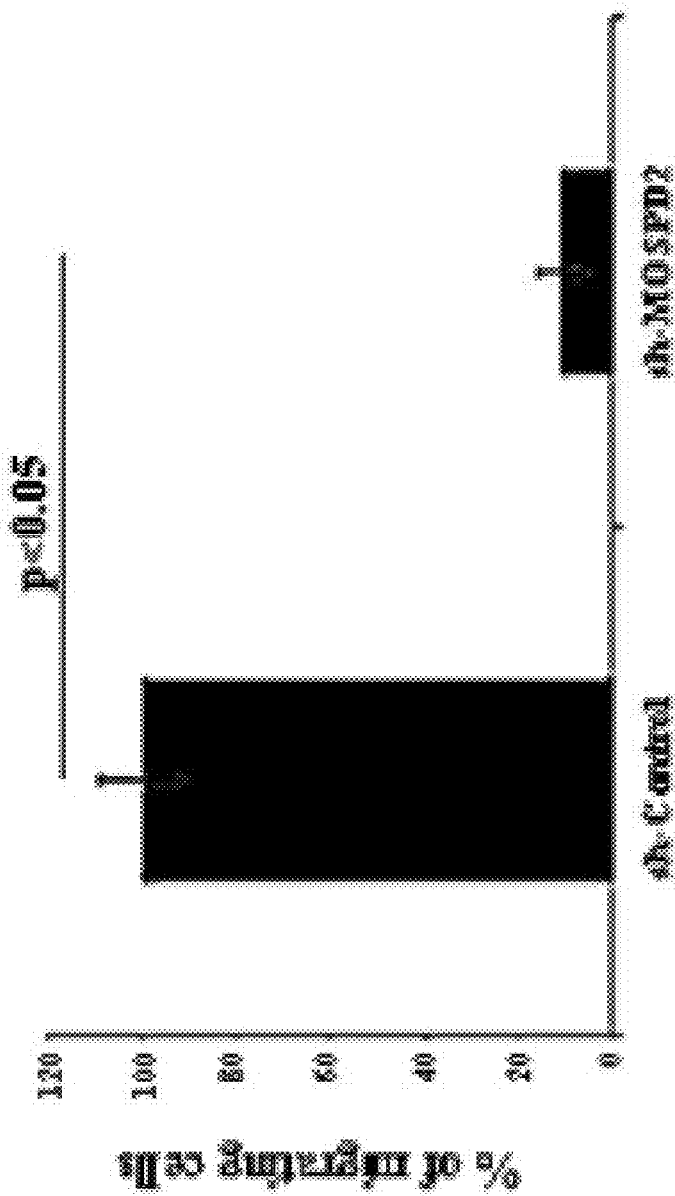
Figure 16C:
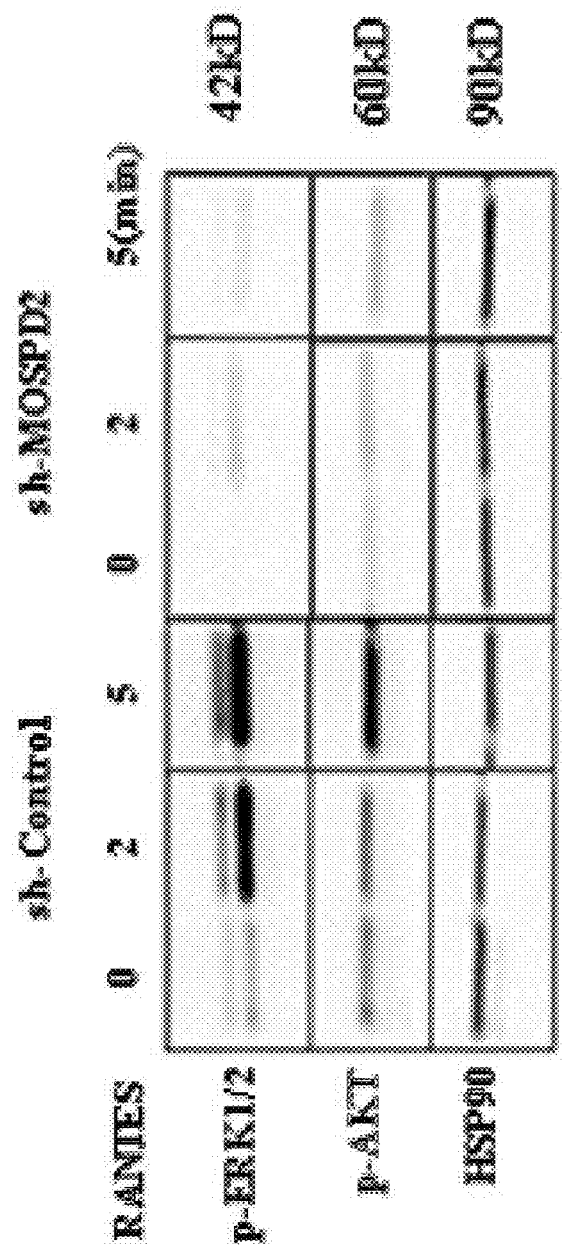

U937 monocytic line cells were transduced with sh-lenti control or sh-lenti MOSPD2 viral particles as described above. FIG. 16A shows the silencing efficacy of sh-lenti MOSPD2 as assessed by Q-PCR and western blot. When tested for migration, MOSPD2-silenced cells were severely impaired in their ability to migrate in vitro towards RANTES (CCL5) (FIG. 16B). Two major signaling pathways recognized as crucial for monocyte migration are the MEK-ERK and PI3K-AKT pathways (Di Lorenzo et al., 2009; Wain et al., 2002). FIG. 16C shows that phosphorylation of ERK and AKT in the presence of RANTES is completely suppressed in MOSPD2-silenced cells.

Figure 16D:
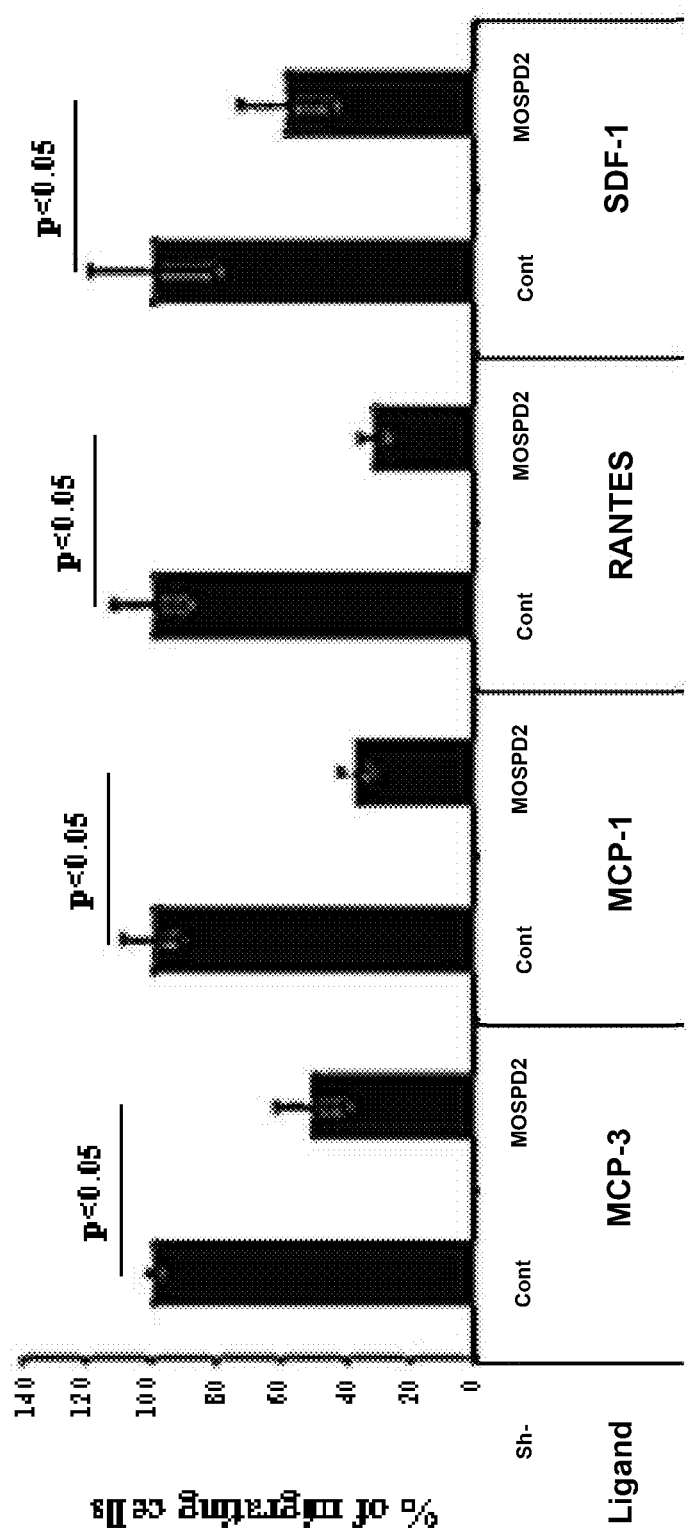
Figure 16E:
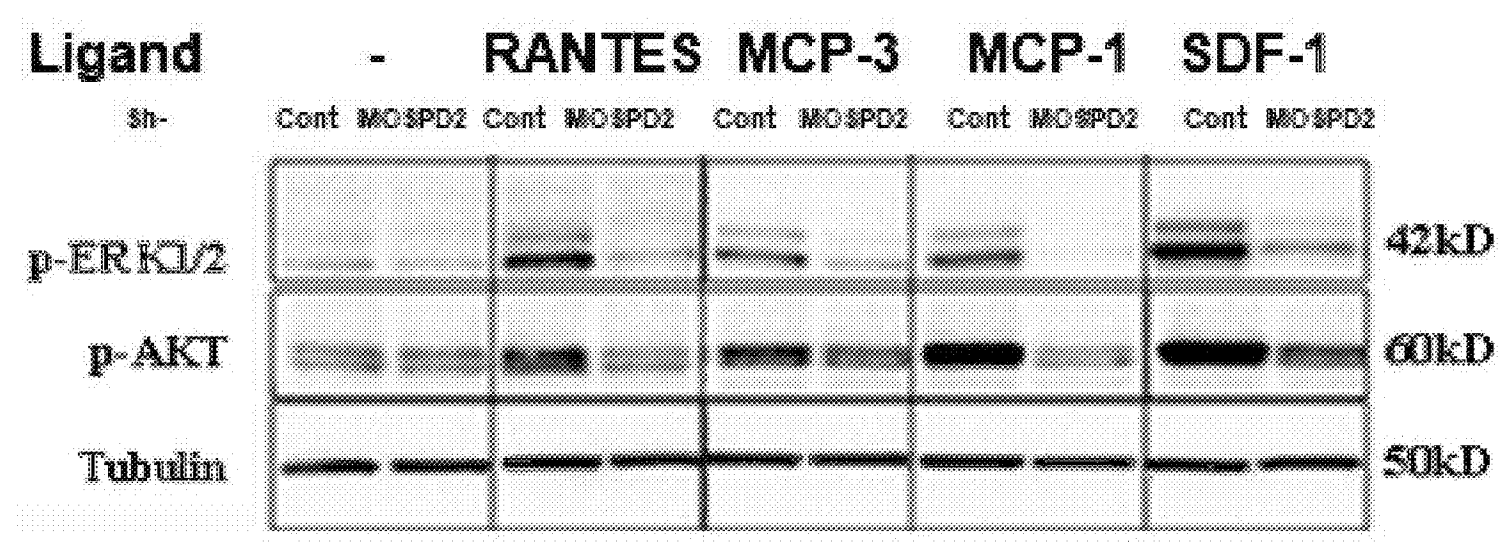

To ascertain whether the effect observed is restricted to only one chemokine, sh-control and sh-MOSPD2 silenced U937 cells were activated with ligands that induce migration and phosphorylation via different chemokine receptors. Silencing MOSPD2 impaired monocyte migration and ERK and AKT phosphorylation regardless of the chemokine used (FIGS. 16D and 16E, respectively).

Example 17

MOSPD2 does not Affect IFN-Gamma-Induced Activation or PKC-Mediated Activation

Figure 17A:
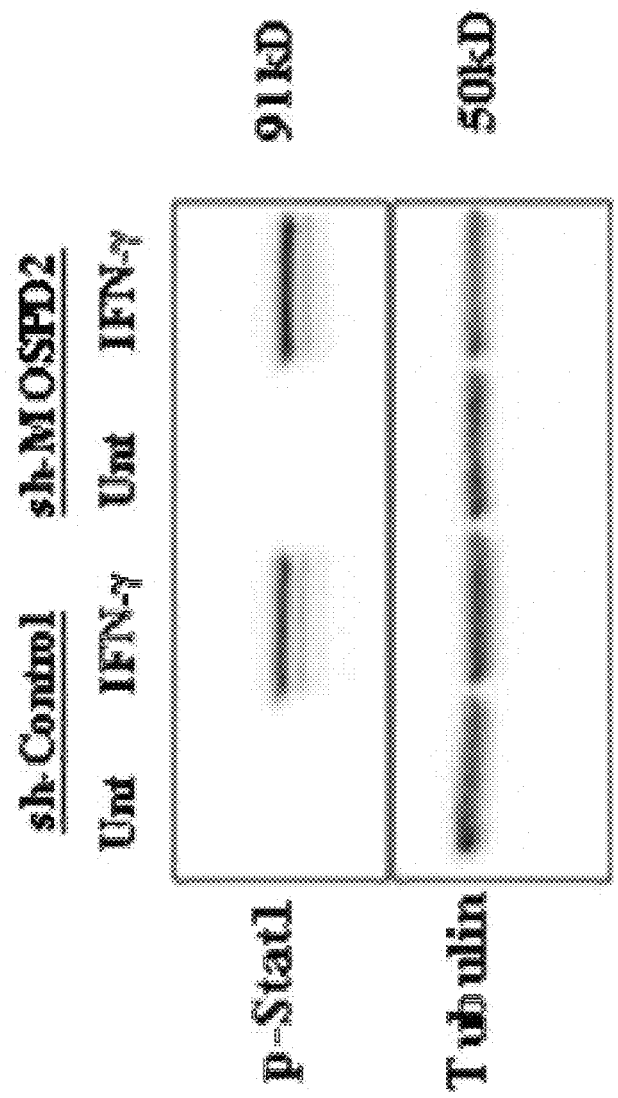
FIGS. 17A-17B show that MOSPD2 does not affect IFN-gamma-induced phosphorylation of STAT1 (p-Stat1) or PMA-mediated phosphorylation of ERK1/2 (p-ERK1/2), respectively, supporting the specificity of the aforementioned MOSPD2 activities.
Figure 17B:
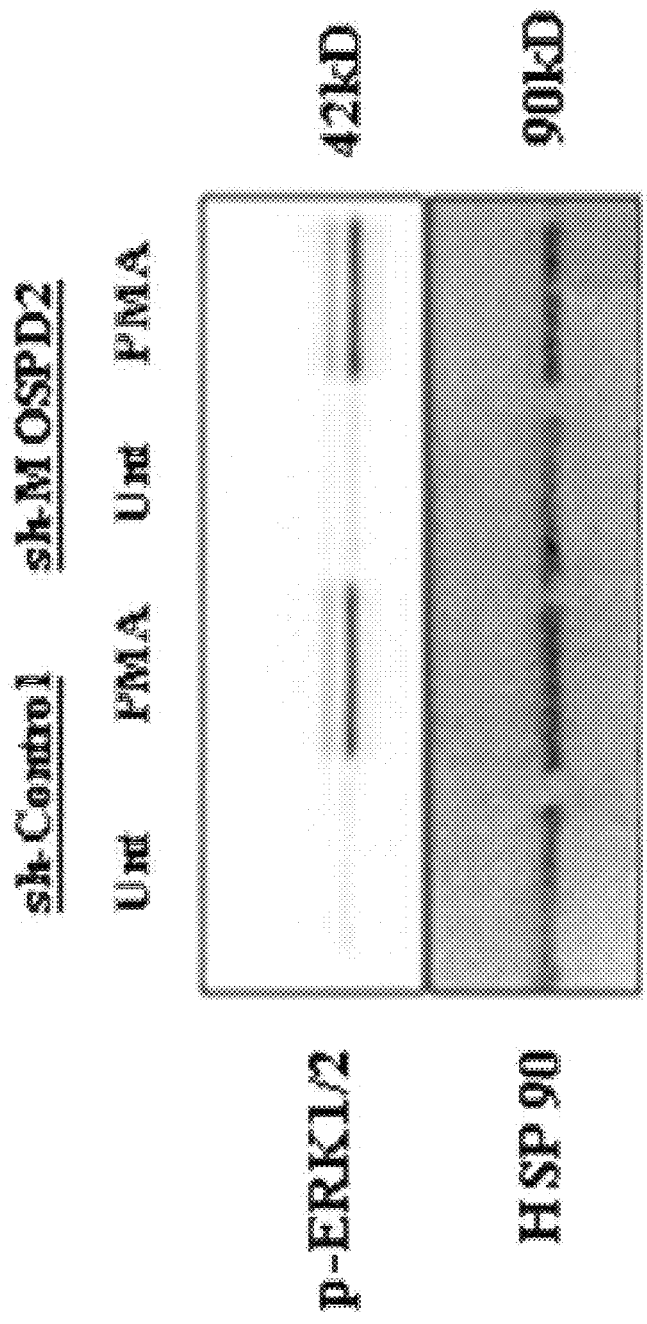
Figure 18D:
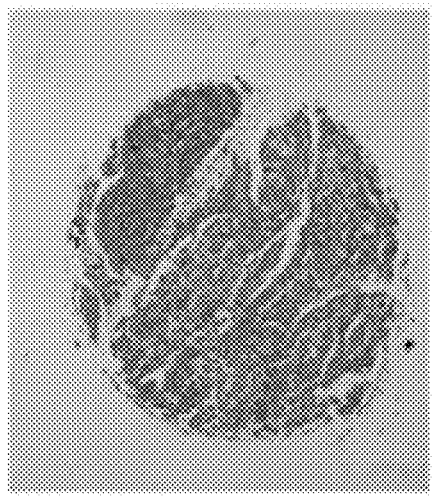
Figure 18E:
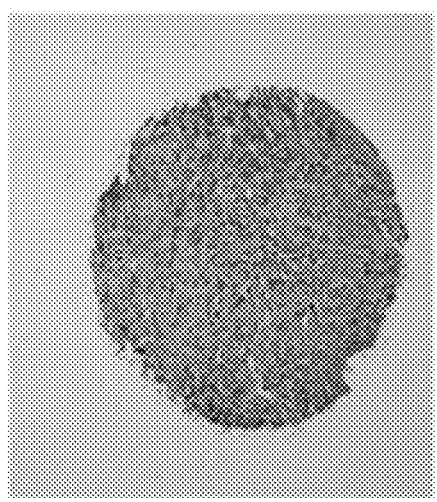
Figure 18F:
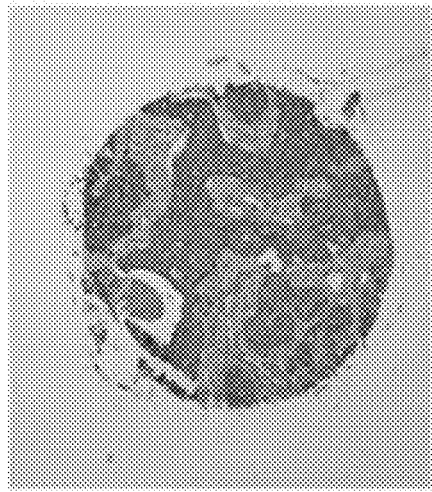

Targeting MOSPD2 did not compromise biological functions of monocytes other than migration. U937 monocytic line cells were transduced with sh-lenti control or sh-lenti MOSPD2 viral particles as described above and treated with IFN-gamma or with PMA. Western blot analysis of treated cells showed that silencing of MOSPD2 did not alter phosphorylation of downstream signaling markers by IFN-gamma or PMA (FIGS. 17A and 17B, respectively). These results suggest that MOSPD2 specifically promotes monocyte migration.

Example 18

Epitope Mapping of Anti-MOSPD2 Antibodies

To determine the epitope(s) that anti-MOSPD2 antibodies may specifically bind on human MOSPD2, binding affinities to various human MOSPD2 fragments are measured, as described herein, by capturing N-terminally biotinylated MOSPD2 fragments via a pre-immobilized streptavidin (SA) on a SA chip and measuring binding kinetics of anti-MOSPD2 antibodies titrated across the MOSPD2 surface (the BIAcore® 3000™ surface plasmon resonance (SPR) system, Biacore, Inc., Piscataway NJ). BIAcore assays are conducted in HBS-EP running buffer (10 mM HEPES pH 7.4, 150 mM NaCl, 3 mM EDTA, 0.005% v/v polysorbate P20). MOSPD2 surfaces are prepared by diluting the N-biotinylated MOSPD2 to a concentration of less than 0.001 mg/mL into HBS-EP buffer and injecting it across the SA sensor chip using variable contact times. Low capacity surfaces, corresponding to capture levels <50 response units (RU) are used for high-resolution kinetic studies, whereas high capacity surfaces (about 800 RU of captured MOSPD2) are used for concentration studies, screening, and solution affinity determinations.

Kinetic data is obtained by diluting antibody G1 Fab serially in two- or three-fold increments to concentrations spanning 1 μM-0.1 nM (aimed at 0.1-10 times estimated $K_D$). Samples are typically injected for 1 minute at 100 μL/min and dissociation times of at least 10 minutes are allowed. After each binding cycle, surfaces are regenerated with 25 mM NaOH in 25% v/v ethanol, which is tolerated over hundreds of cycles. An entire titration series (typically generated in duplicate) is fit globally to a 1:1 Langmuir binding model using the BIAevaluation program. This returns a unique pair of association and dissociation kinetic rate constants (respectively, $K_{on}$ and $K_{off}$) for each binding interaction, whose ratio gives the equilibrium dissociation constant ($K_D=K_{off}/K_{on}$).

Anti-MOSPD2 antibodies may bind to one or more of the following amino acid regions of human MOSPD2, numbered according to SEQ ID NO:1 (amino acid residues 1-518): 508-517, 501-514, 233-241, 509-517, 212-221, 13-24, 505-517, 505-514, 89-100, 506-517, 233-245, 504-514, 128-136, 218-226, 15-24, 83-96, 42-50, 462-474, 340-351, 504-517, 462-470, 327-337, 21-32, 217-226, 510-517, 178-190, 497-509, 504-516, 64-77, 504-515, 147-159, 503-315, 88-97, 208-218, 178-191, 502-515, 503-516, 497-505, 500-509, 189-202, 189-197, 505-516, 1-63, 82-239, 93-234, 327-445, 327-431, and 497-517.

Example 19

Additional Anti-MOSPD2 Antibodies

Additional anti-MOSPD2 antibodies are generated that recognize one or more MOSPD2 epitopes, following the methodology described in Example 1 (polyclonal antibodies) or Example 8 (monoclonal antibodies).

Briefly, portions of MOSPD2 identified in Example 18 as MOSPD2 epitopes are fused to human Fc and immobilized on a solid support. A HuCAL® library (HuCAL PLATINUM® Platform; Bio-Rad AbD Serotec, GmnH) presented on phage particles is incubated with the immobilized antigen. Nonspecific antibodies are removed by extensive washing and specific antibody phages are eluted by adding a reducing agent. Antibody DNA is isolated as a pool and subcloned into an *E. coli* expression vector to generate bivalent F(ab')$_2$ mAb. Colonies are picked and grown in a microtiter plate. The cultures are lysed to release the antibody molecules and screened for specific antigen binding by ELISA and FACS. Unique antibodies are expressed and purified using one-step affinity chromatography, and then tested again by ELISA and FACS for specificity.

Example 20

MOSPD2 Expression is Increased in Correlation with Tumor Grade in Various Types of Cancer To determine whether MOSPD2 expression was associated with tumor progression, slides carrying normal and cancerous tissues in different tumor grades were screened using anti-MOSPD2 antibody as described in the Materials and Methods section. MOSPD2 abundance was scored according to the staining intensity on a scale from 0 to 3. In cases where intra-heterogeneity staining within a single core was observed, the score of the area with the highest coverage was assigned.

FIGS. 18A-18F show representative MOSPD2 staining in Breast cancer and control tissue. Normal adjacent tissue (NAT) served as a negative control, and the escalating tumor stages included lobular carcinoma in situ (LCIS), intraductal carcinoma in situ (IDIS), invasive ductal carcinoma (IDC), invasive lobular carcinoma (ILC) and Metastatic invasive ductal carcinoma (MIDC). While representative NAT, LCIS and IDIS staining were negatively stained for MOSPD2, IDC, ILC and MIDC representative staining demonstrated intense positive MOSPD2 staining.

Figure 19:
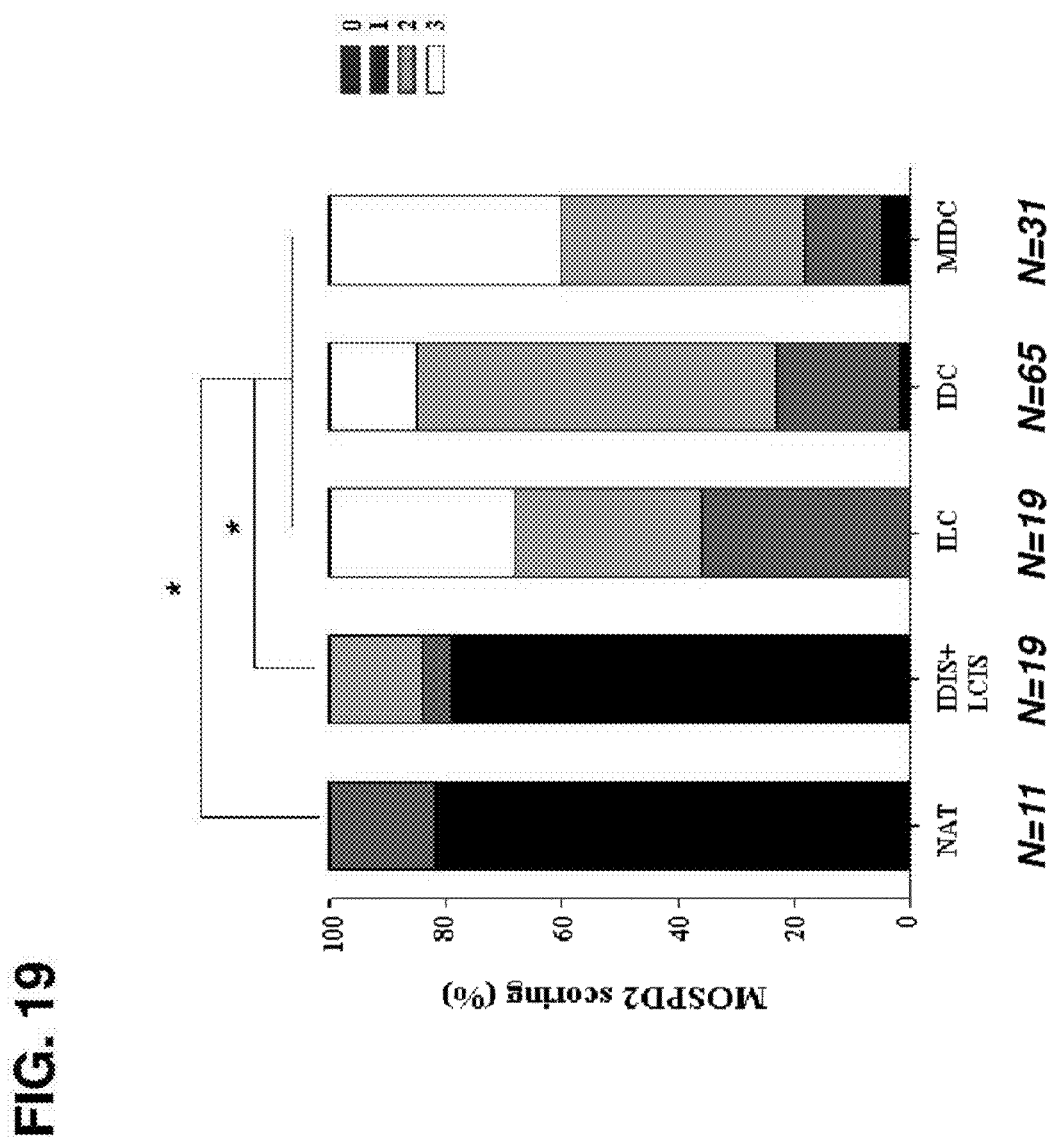
FIG. 19 shows scoring of MOSPD2 expression intensity (in a scale of 0-3, where 0 is no expression and 3 is very high expression) in samples from different stages of breast cancer or normal adjacent tissue (NAT) (* $p<0.001$).
Figures 20A, 20B:
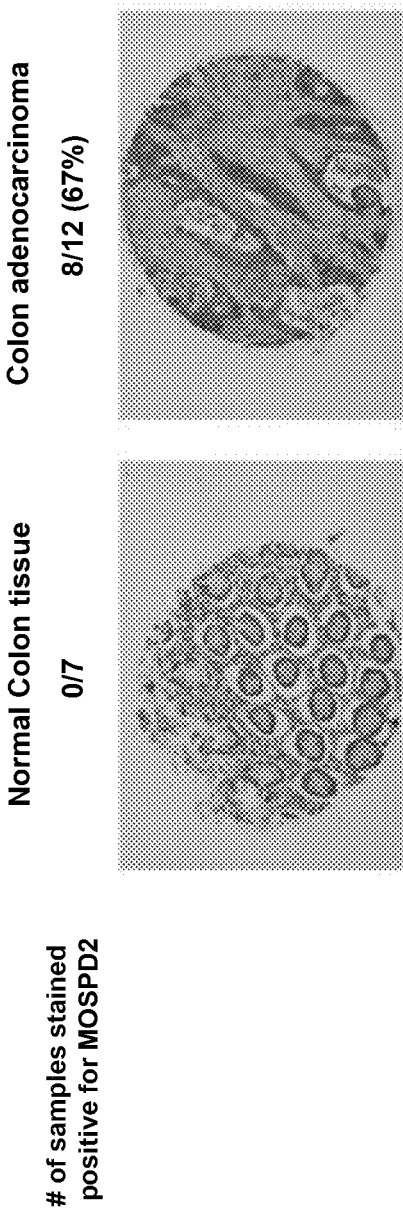
Figure 21C:
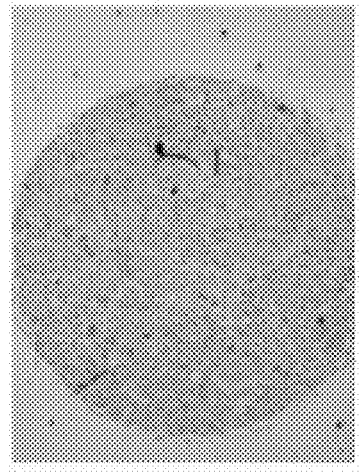
Figure 21B:
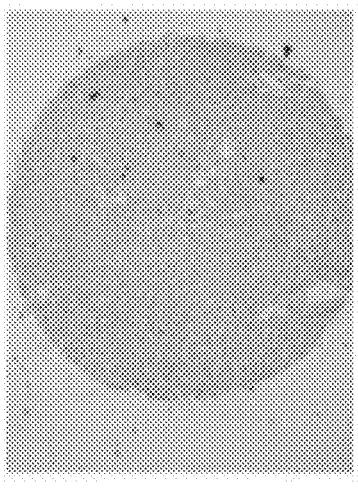
Figure 21A:
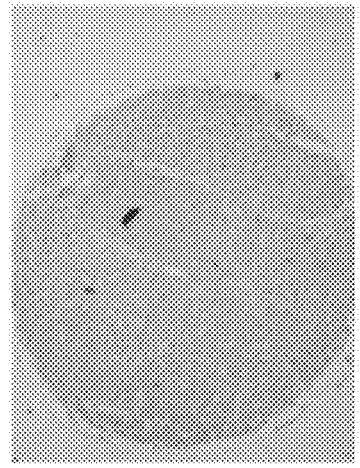

FIG. 19 demonstrates increased MOSPD2 staining intensity in invasive and metastatic breast cancer. Within NAT, only 18% percent ($2/11$) of samples showed a staining intensity of 1, while 21% ($4/19$) of in situ carcinoma samples (IDIS+LCIS) were scored 1 or 2. However, analysis of invasive and metastatic tissues demonstrated higher frequency in score of 2 and increased staining intensity up to score of 3, compared to NAT and in situ carcinoma (IDIS+LCIS). Thus, the percent of combined scores 2 and 3 for ILC, IDC and MIDC were 63% ($12/19$), 77% ($50/65$) and 81% ($25/31$), respectively.

MOSPD2 expression correlated with the transformation of cells from normal to cancerous in colon and in hepatic tissues as well. FIGS. 20A-20D demonstrate that in 67% of colon cancer samples and in 45% of hepatocellular carcinoma samples tested, there was a positive MOSPD2 staining. No MOSPD2 staining (0%) was detected in the normal colon or liver tissues tested.

MOSPD2 expression also correlated with malignancy. FIGS. 21A-21E show intense MOSPD2 staining in hepatocellular carcinoma that increased with tumor grade, while normal and NAT samples were negative for MOSPD2 staining.

Figure 22B:
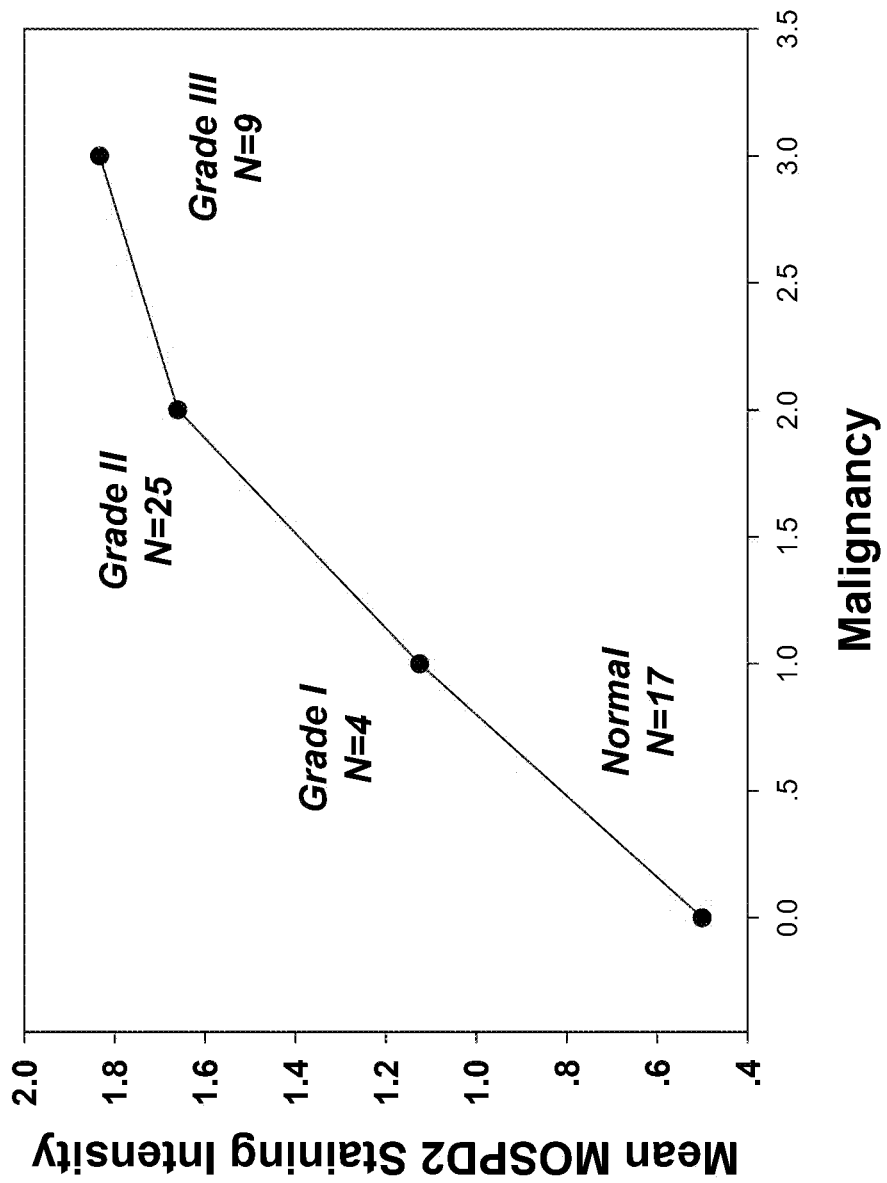

FIGS. 22A-22B summarize the intensity of MOSPD2 staining in malignant liver tissues or controls from FIGS. 21A-21E. MOSPD2 staining intensity was significantly increased by 3.2 or 4 fold in malignant samples in comparison to normal and NAT, respectively (p≤0.001). FIG. 22B shows the increase in MOSPD2 staining intensity in different stages of hepatocellular carcinoma.

Example 21

VB-201 Inhibits MOSPD2

Labeling of VB-201 and VB-221

VB-201 and VB-221 were labeled with biotin as follows. VB-201, VB-221 and ovalbumin (OVA, Sigma, Israel) were dissolved in 0.1 M MES buffer (Thermo Scientific, Rockford, IL) and conjugated using EDC [1-ethyl-3-(dimethyl-aminopropyl) carbodiimide HCL] (Thermo Scientific) at a molar ratio of 100 (VB-201/VB-221):1 (OVA):240 (EDC) for 2-3 hr at room temperature. After which, samples were transferred to 10 kDa dialysis cassettes (Thermo Scientific) and dialyzed overnight against PBS. The ovalbumin bound VB-201 (OB201) and VB-221 (OB221) were then conjugated with amine-PEG2-biotin (in 0.1 M MES buffer) using EDC at a molar ratio of 1 (OB201/OB221):100 (amine-PEG2-biotin):700 (EDC). The reaction was allowed to proceed for 2-3 hours at room temperature after which samples were again transferred to a 10 kDa dialysis cassette and dialyzed overnight against PBS.

Precipitation

Cells were lysed using a 1% NP-40 lysis buffer containing 1:100 protease and phosphatase inhibitors, followed by 20 min incubation on ice and 15 min centrifugation at maximum speed. Samples were incubated overnight at 4° C. with solvent, OB201 or OB221 in a rotator. Streptavidin agarose beads (Sigma, Israel) were added for 2 hours. Protein elution was performed with lysis buffer without DTT for 10 min at room temperature. Sample loading, transfer and immunoblotting were performed as described above.

Results

VB-201 Binds MOSPD2

It was previously shown that VB-201 inhibits migration of monocytes in vitro and in vivo. However, VB-221, a derivative of VB-201, did not inhibit chemokine-induced signaling and migration in human monocytes. Using labeled VB-201 and VB-221, proteins from human monocytes were precipitated and differential display by Mass-Spectrometry, was studied. The Mass-Spectrometry results revealed that MOSPD2 has a strong binding to VB-201 but not VB-221.

Figure 23:
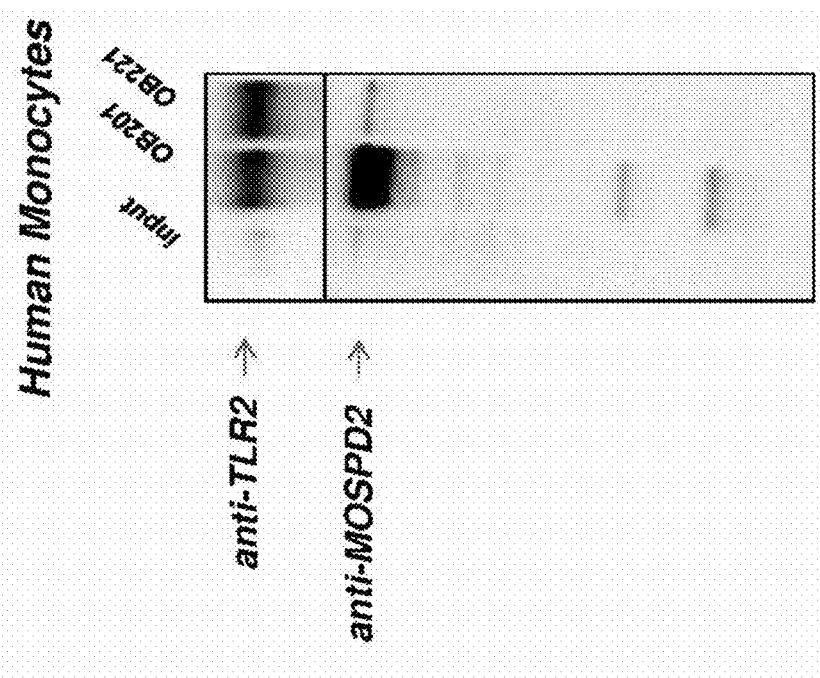
FIG. 23 presents images of Western blots showing that VB-201 binds to MOSPD2 from cell lysate of human CD14 monocytes. Labelled VB-201 or VB-221 (OB201 or OB221) was added to the cell lysate and proteins were precipitated. Samples were run on a gel and blotted against TLR2 and MOSPD2.

To further validate these results, labelled VB-201 and VB-221 were employed on cell lysates from human CD14 monocytes. Samples were then probed with anti MOSPD2 and TLR2. Whereas VB-201 and VB-221 precipitated TLR2 in a comparable intensity, VB-201 precipitated MOSPD2 markedly more intense than VB-221 (FIG. 23). These results also indicate that VB-201 binds MOSPD2.

Example 22

MOSPD2 Promotes EGF-Induced Signaling Events in Breast Cancer Cells

MOSPD2 Silencing in MDA-231 Breast Cancer Cells

EGF ligation to the EGF Receptor (EGF-R) induces a cascade of signaling that involves phosphorylation downstream to the receptor. We investigated whether MOSPD2 is affecting signaling cascades induced by EGF. The human breast cancer cell line MDA-MB-231 (hereafter MDA-231) (HTB-26) was purchased from ATCC. The cells ($2\times10^6$ in 2 ml) were placed in a 15 ml tube. Lentiviral particles expressing CRISPR non-target control (CRISPR-Control) or CRISPR human MOSPD2 (CRISPR-MOSPD2) were applied on the cells which were then spun for 60 min, 2000 rpm in room temperature in the presence of 8 µg/ml polybrene (Sigma, Israel). The cells were then seeded in a 6 well plate. After 72 hours, fresh medium containing puromycin (4 µg/ml Sigma, Israel) was added for the selection of transduced cells. Single cell cloning was performed on CRISPR transduced cells to isolate cells with silenced MOSPD2 protein expression and impaired migration.

Figure 24:
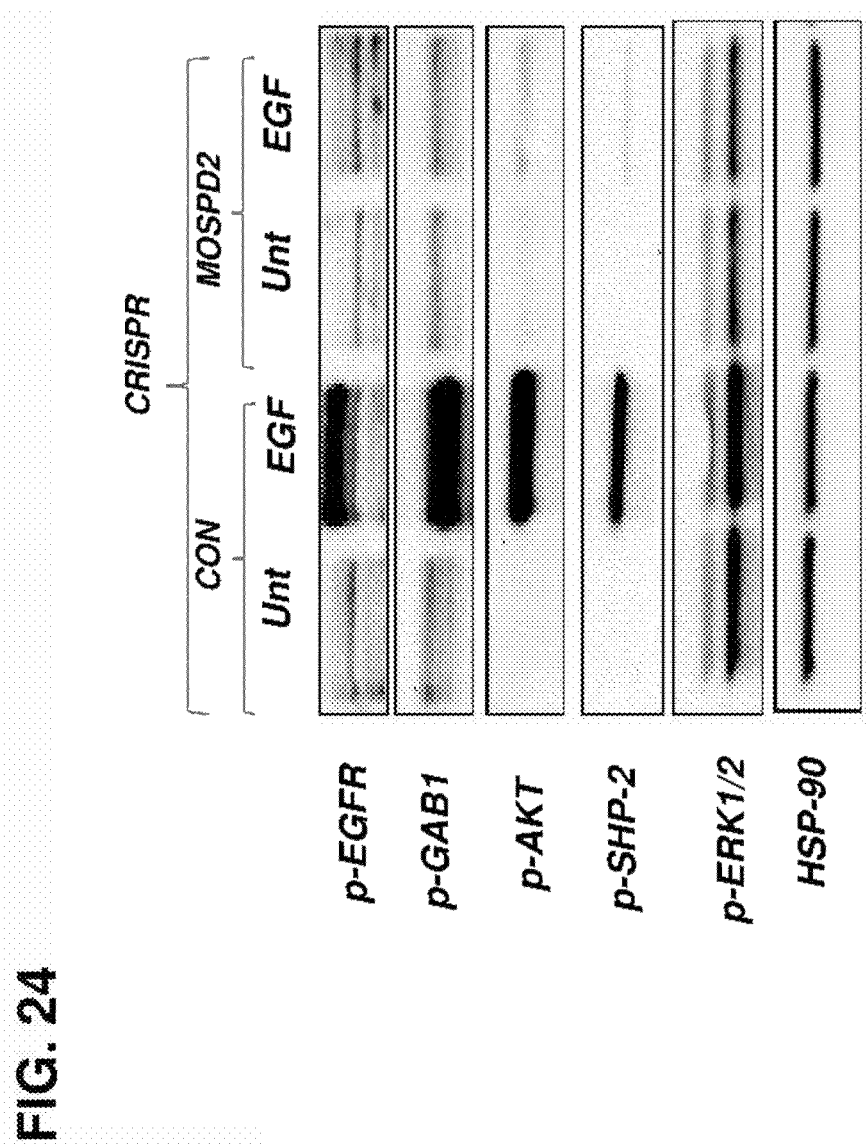
FIG. 24 presents images of Western blots showing that MOSPD2 promoted EGF-induced signaling events in breast cancer cells.

When CRISPR-Control MDA-231 cells were activated with EGF, the EGF-R and downstream signaling molecules became phosphorylated. However, in CRISPR-MOSPD2 silenced cells, a remarkable inhibition in EGF-R phosphorylation and the downstream molecules was observed (FIG. 24). These results indicate that MOSPD2 regulates EGF-induced signaling pathways in breast cancer cells.

All publications, patents and patent applications mentioned in this application are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

---

What is claimed is:

1. A method of treating cancer or metastasis of cancer in a subject, comprising administering to the subject an inhibitor of MOSPD2, wherein the inhibitor is a DNA or RNA inhibitor, and wherein the cancer comprises cells that express MOSPD2.

2. The method of claim 1, wherein the inhibitor is an antisense DNA, decoy DNA, double-stranded DNA, single-stranded DNA, complexed DNA, encapsulated DNA, viral DNA, plasmid DNA, RNAi, miRNA, siRNA, shRNA, antisense RNA, naked RNA, encapsulated RNA, viral RNA, double-stranded RNA, or a molecule capable of generating RNA interference.

3. The method of claim 2, wherein the inhibitor is shRNA.

4. The method of claim 1, wherein the cancer is bladder cancer, brain cancer, breast cancer, colon cancer, rectal cancer, kidney cancer, liver cancer, lung cancer, esophageal cancer, gallbladder cancer, ovarian cancer, pancreatic cancer, stomach cancer, cervical cancer, thyroid cancer, prostate cancer, skin cancer, hematopoietic cancer, cancer of mesenchymal origin, cancer of central or peripheral nervous system, endometrial cancer, head and neck cancer, glioblastoma, or malignant ascites.

5. The method of claim 4, wherein the lung cancer is a non small cell lung cancer.

6. The method of claim 4, wherein the hematopoietic cancer is a hematopoietic cancer of lymphoid lineage.

7. The method of claim 6, wherein the hematopoietic cancer of lymphoid lineage is leukemia, acute lymphocytic leukemia, chronic lymphocytic leukemia, acute lymphoblastic leukemia, B-cell lymphoma, T-cell lymphoma, Hodgkin's lymphoma, non-Hodgkin's lymphoma, hairy cell lymphoma, or Burkitt's lymphoma.

8. The method of claim 4, wherein the hematopoietic cancer is a hematopoietic cancer of myeloid lineage.

9. The method of claim 8, wherein the hematopoietic cancer of myeloid lineage is acute myelogenous leukemia, chronic myelogenous leukemia, myelodysplastic syndrome, or promyelocytic leukemia.

10. The method of claim 4, wherein the cancer of mesenchymal origin is fibrosarcoma, rhabdomyosarcoma, soft tissue sarcoma, or bone sarcoma.

11. The method of claim 4, wherein the cancer of central or peripheral nervous system is astrocytoma, neuroblastoma, glioma, or schwannomas.

12. The method of claim 1, wherein the cancer is anal cancer, bone cancer, gastrointestinal stomal cancer, gestational trophoblastic disease, keratoacanthoma, malignant mesothelioma, multicentric castleman disease, multiple myeloma and other plasma cell neoplasms, myeloproliferative neoplasms, osteosarcoma, ovarian cancer, fallopian tube cancer, primary peritoneal cancer, penile cancer, retinoblastoma, rhabdomyosarcoma, seminoma, soft tissue sarcoma, stomach cancer, testicular cancer, teratocarcinoma, thyroid follicular cancer, vaginal cancer, vulvar cancer, Wilms tumor and other childhood kidney cancers, or xeroderma pigmentosum.

13. The method of claim 1, wherein the number of circulating monocytes or tumor associated macrophages near or within a mass of the cancer is reduced.

14. The method of claim 1, wherein the migration of circulating monocytes or tumor associated macrophages near or within a mass of the cancer is reduced.

15. The method of claim 1, wherein the subject is a human.

16. The method of claim 1, wherein the method is treating cancer in the subject.

17. The method of claim 1, wherein the method is treating metastasis of cancer in the subject.

\* \* \* \* \*